US006133317A

United States Patent [19]
Hart

[11] Patent Number: 6,133,317
[45] Date of Patent: *Oct. 17, 2000

[54] OXALIC ACID OR OXALATE COMPOSITION AND METHOD OF TREATMENT

[76] Inventor: Francis J. Hart, 390 Ryan Rd., Pea Ridge, Ark. 72751

[ * ] Notice: This patent is subject to a terminal disclaimer.

[21] Appl. No.: 08/629,538

[22] Filed: Apr. 9, 1996

Related U.S. Application Data

[60] Provisional application No. 60/006,785, Nov. 15, 1995.

[51] Int. Cl.$^7$ ........................ A61K 31/194; A61K 31/225
[52] U.S. Cl. ............................ 514/574; 514/547; 424/49
[58] Field of Search .................................... 514/574, 547

[56] References Cited

U.S. PATENT DOCUMENTS

| | | | |
|---|---|---|---|
| 3,542,573 | 11/1970 | Biland et al. | 106/186 |
| 3,787,589 | 1/1974 | Stephens et al. | 426/325 |
| 4,156,067 | 5/1979 | Gould | 528/73 |
| 4,285,972 | 8/1981 | Chou et al. | 424/326 |
| 4,340,609 | 7/1982 | Chou | 424/322 |
| 4,760,157 | 7/1988 | Child et al. | 556/137 |
| 4,900,746 | 2/1990 | Hanson et al. | 514/400 |
| 5,137,722 | 8/1992 | Costello | 424/195 |
| 5,151,274 | 9/1992 | Saltman et al. | 424/630 |
| 5,175,144 | 12/1992 | Walser | 514/2 |
| 5,183,674 | 2/1993 | Olin | 426/2 |
| 5,227,248 | 7/1993 | Wullschleger et al. | 426/549 |
| 5,245,095 | 9/1993 | Graves et al. | 585/351 |
| 5,292,511 | 3/1994 | Kim et al. | 424/195.1 |
| 5,292,773 | 3/1994 | Hirsch et al. | 514/554 |
| 5,310,554 | 5/1994 | Haigh | 424/439 |
| 5,314,686 | 5/1994 | Todd, Jr. | 424/401 |
| 5,324,443 | 6/1994 | Arif et al. | 252/142 |
| 5,330,972 | 7/1994 | Cope | 514/2 |
| 5,346,707 | 9/1994 | Olin | 426/69 |
| 5,376,361 | 12/1994 | Perricone | 424/59 |
| 5,401,325 | 3/1995 | Meielic et al. | 134/39 |
| 5,455,372 | 10/1995 | Hirai et al. | 560/179 |
| 5,470,874 | 11/1995 | Lerner | 514/474 |

OTHER PUBLICATIONS

The Merck Index, 11th ed, Merck & co., Inc., Rahway, N.J., p. 1093, 1989.

Houpis, I., Molina, A., Reamer, R., Lynch, J., Volante, R.P., and Reider, P. Towards the Synthesis of HIV–Protease Inhibitors. Synthesis of Optically Pure 3–Carboxyl–decahydroisoquinolines. Tetrahedron Letters, vol. 34, No. 16, pp. 2593–2596, 1993.

Dyer, An Index of Tumor Chemotherapy, NIH, Mar., 1949, pp. 10–12 and 72 (No. 2015).

Hodgkinson, A. Oxalic Acid in Biology and Medicine, Academic Press, 1977—pp. 1–3, 16–17, 18–21, 23, 37–38, 49–51, 69–80, 84–88, 100–103, 110–111, 122–124, 130, 133–135, 153–156, 159–164, 168–174, 180–182, 196–207, 216–228, 238.

Davis, Adelle, Lets Get Well, Penguin Group, 1972—pp. 195, 204–205, 213, 299.

Cowdry, E. Croninger, A. Solaric, S. Suntzeff, V. Cancer, Journal of the American Cancer Society, Combined Action of Cigarette Tar & Beta Radiation of Mice—1961, vol. 14—pp. 344–352.

Bock, F. Moore, G. Journal of the National Cancer Institute, Carcinogenic Activity of Cigarette Smoke Condensate. I. Effect of Trauma & Remote X–Irritation. vol. 22 No. 2—1959—pp. 401–411.

Lundin, Jr., F. Lloyd, J & Smith, E. and Archer, V. & Holaday, d. Health Physics. Mortality of Uranium in Relation to Radiation Exposure, Hard–Rock Mining and Cigarette Smoke 1950 through Sep. 1967. pp. 571–578.

Svendsen, L. Rattan, Surech I.S. Clark, Brian F.C. Journal of Ethnopharmacology—1994 Testing Garlic for Possible Anti–Ageing Effects on Long–term Growth Charactistics, Morphology and Macro Molecular Synthesis of Human Fibroblasts in Culture—pp. 125–133.

Ney, D.M. The Low Oxalate Diet Book for the Prevention of the Oxalate Kidney Stones—pp. 944–945 & Appendix Table 13, University of California, San Diego 1981.

U.S. Department of Health & Human Services Public Health Service National Institutes of Health, NIH Publication, Eat More Fruits & Vegetables, Oct. 1991.

Chem One Corporation. Product Data Sheet, 1995.

Occupational Health Services. msds on oxalic acid, 1994.

The Merck Manual, Diagnosis and Therapy, 1987 pp. 2465–2466, Oncology pp. 1206–1228.

(List continued on next page.)

Primary Examiner—Richard L. Raymond
Attorney, Agent, or Firm—Head, Johnson & Kachigian

[57] ABSTRACT

An oxalic acid or oxalate composition and method of treatment of warm blooded animals including humans and pets is provided which includes at least one therapeutically effective form of oxalic acid or oxalate selected, for example, from oxalic acid in a free acid, ester, lactone or salt form, oxalates including sodium oxalate, a nutritional supplement containing oxalic acid or oxalate, oxalic acid dihydrate, anhydrous oxalic acid, oxamide, oxalate salts, natural or processed foods including molds, plants or vegetables containing oxalic acid or oxalate, beverages, liquids or juices containing oxalic acid or oxalate, additives containing oxalic acid or oxalate, and combinations thereof. The composition may also contain a pharmaceutically acceptable carrier or diluent for the therapeutically effective form of oxalic acid or oxalate. A method is provided including the steps of periodically administering a therapeutically effective dosage of a composition including at least one therapeutically effective form of oxalic acid or oxalate and reducing the intake of oxalic acid or oxalate blockers such as citric acid, ascorbic acid (vitamin C), pyridoxine hydrochloride (vitamin B6), calcium, alcohol, resins, clays, dairy products containing calcium, fruits, coconut, beverages containing alcohol, ascorbic acid or citric acid, red meat or white meat of fowl containing pyridoxine hydrochloride, or other foods, nutritional supplements or beverages containing alcohol, citric acid, ascorbic acid, pyridoxine hydrochloride, or combinations thereof.

104 Claims, 1 Drawing Sheet

OTHER PUBLICATIONS

NIH Specification 11-133 Open Formula Rat and Mouse Ration 9NIH)0-07) Nov. 1, 1986.

NIH Specification 11-137 Crude Protein Autoclavable (NIH-31)) Nov., 1986.

Organic Gardening Articles, Rodale Press, Inc. Hurley, J.B. Calcium From the Garden Apr. 1986, pp. 96-98 Duke, L.A. Weeds? or Wonder Drugs? Jul. 1994 pp. 38-39 Duke, J.A. Eat Your Weedies Jul. 1993 pp. 31-35 Mattern, V. Don't Weed 'em, Eat 'em Apr. 1994 pp. 71-74.

Better Nutrition—Veggie Corner—Broccoli and Watercress Are Rich Cancer Fighters, Aug. 1994 p. 22 Editors Desk—Novel Cancer Therapies Deserve a Fair Hearing, Aug. 1994 p. 6.

Parade Magazine Special Intelligence Report, men Should Think Twice Before Eating Steak, Oct. 1994, p. 16.

Journal National Cancer Institute, No. 85, Explanation For Link Between Alcohol and Breast-Cancer risk 1993, abstract.

Readers Digest, News From the World of Medicine, Device Spots Colon Cancer & Indoor Tanning? Don't Do It. Mar. 1994. Sunscreen: Slather It On, Do Fats Fuel Prostate Cancer? May 1994. Folic Acid, Superstar, Jun. 1994.

Letters, Natural Health. Beta-Carotene Debate Continues, Nov. 1994.

Microsoft Internet Explorer/NECX From Gopher://gopher.nih. gov/00/clin/cdcs/67. kidney-Prevention and Treatment of Kidney Stones national Institute of Health Consensus Development Conference Statement, Mar. 1988 pp. 1-14.

Microsoft Internet Explorer/Open Text Index From:http://www/mcs/net/-joyce/new,html Essiac Tea From Canada Comes A Remedy Called Essiac, Or Ojibwa Tea 1995, pp. 1-7 From: gopher://wiretap/spies/com/oo/lLibrary/Fringe/Pharm/essiac.txt Essiac: a natural herbal alternative cancer treatment. Glum, G.L. Calling of An Angel, Apr. 1993 pp. 1-15.

From:http://www/envirolink/org/arrs/VRG/calcium.html Mangels, R. Calcium in the Vegan Diet 1991 pp. 1-6.

Weil, Andrew Natural Health, Natural Medicine, How Not to Get Cancer, Houghton Mifflin Company 1990 pp. 169-189.

Robbins, J. Diet for a New America. Losing A War We Could Prevent, Stillpoint Publishing 1987, pp. 248-273, 403-409.

Berkely, B. Nutritional Protocol for HIV, Project Inform San Francisco 1994.

Nau, Jean-Yves Preventing Spread of BSE, The Lancet Sep. 1994 vol. 344, p. 808.

Carper, Jean, Foods That Fight Cancer, Reader's Digest, Jan. 1994, pp. 119-122.

OXALIC ACID OR OXALATE COMPOSITION AND METHOD OF TREATMENT

CROSS REFERENCE TO RELATED APPLICATIONS

This application claims benefit of U.S. Provisional Patent Application Ser. No. 60/006,785, filed Nov. 15, 1995.

BACKGROUND OF THE INVENTION

This invention relates to oxalic acid or oxalate compounds, nutritional supplements, natural or processed foods, beverages, and methods of treatment utilizing oxalic acid or oxalate compounds, vitamin B6, vitamin C, alcohol, calcium, and/or foods, nutritional supplements, beverages, and the like containing one or more of these compounds.

The story begins with two toy poodles, Turk and Taka. These animals lived a normal house life. Except for the occasional trip or walk to the nearby reservoir, their territory was the house and backyard. As young pups they were full of energy and, of course, very spoiled. Habits, mostly bad ones, were easily formed, such as eating people food, some of which, according to a veterinarian, would not hurt them. Turk became fond of SNICKERS® brand candy bars, especially the small bite-size kind, and also carrots and beets, both of which are appearing in some commercial dog foods today.

During this time, Turk's owner, the present applicant and inventor, was doing a great deal of traveling, averaging one trip a week, and he always kept a small SNICKERS® bar near the front door in case he returned home without one. Another one of Turk's favorite treats was the small soybean crackers in oriental cocktail mix, which Turk's owner ate constantly when he was home.

When Turk was about a year and six or seven months old, Turk began to slow down. Turk's eagerness to play left him, and his appetite diminished except for the little treats mentioned above. Turk was drinking much more water and had frequent accidents in the house, especially at night. Turk's color changed from a parfait tinge to a solid white, and just before his death, to a dull grayish-white.

When Turk began to vomit occasionally after eating or drinking, Turk's owner became concerned and took Turk to the veterinarian. The examination revealed nothing, and the veterinarian diagnosed Turk as having indigestion and gave Turk some medicine. Turk's condition worsened, and so Turk was returned to the veterinarian. Blood and urine samples were taken, and test results revealed that Turk's urine was watery, but otherwise all right. The blood however, showed a high white cell count, and the veterinarian thought there might be an infection and prescribed pills. One single pill brought on violent vomiting. Turk's owner stopped giving Turk the pills and started Turk on amoxicillin.

Turk's condition worsened, so Turk was taken to the animal hospital center where they determined Turk's kidneys were failing. Turk was put on an IV due to severe dehydration. The doctors stated that they could not treat Turk unless Turk's owner could tell them what poison or chemical Turk had ingested. For the next several days Turk's owner went on a frantic search for answers. Turk's owner contacted a number of agencies for possible clues to the poisoning: Tri-County Health Department; two toxicologists with the EPA; the U.S. Corps of Engineers, who assured him that they test the reservoir daily for contaminants; and UCLA and University of Illinois poison centers. Heavy rains would bring standing water into the backyard, so Turk's owner tracked down the owners of a stable and a nursery that used to operate in the area before the houses were built, to see if they had used any type of toxic sprays. Turk's owner contacted nurseries from which he had recently bought plants. Turk's owner even contacted the 3M Company, since new carpeting with SCOTCHGARD® had been installed. Turk's owner asked all neighbors who had pets to find out if their pets had become sick.

Turk's owner also called veterinary clinics to find out if they had diagnosed similar cases recently. He also searched every square foot of the house, garage, and storage building looking for chemicals, especially antifreeze. Out of desperation, Turk's owner pleaded with the veterinarians to list poisons that had the same fingerprint, and he would then choose one so veterinarians could begin treatment. The veterinarians declined. When blood began to appear in Turk's stool and vomit, and the kidneys had shut down, Turk was put to sleep. Turk's owner vowed that with God's help he would find out what had destroyed Turk.

The attending veterinarian at the veterinary hospital was an organ specialist and professor at Colorado State University. The veterinarian extended his sympathy and after a few other exchanges he informed Turk's owner that there is one substance very damaging to renal tissue—oxalates. The owner drove directly to his company's quality control department lab where he cornered a chemist and questioned him about oxalates. The chemist said that an oxalate is a compound found in trees, mainly oaks. The owner's curiosity was running high, and as soon as he could break away from work, he went straight for a dictionary. Oxalate is defined as a salt or ester of oxalic acid, and the acid definition refers back to the oak tree. Oxalic acid is further defined as an industrial chemical used in textile and dye manufacturing as a bleaching agent. From the dictionary, he went to the chemical books, found oxalic acid and got promptly lost in a maze of formulae and equations. The owner eliminated oxalates or oxalic acid from his mind as a cause of Turk's death. What did stay in his mind was Turk's death, and again he renewed his vow to find the answer. He could not get Turk out of his thoughts, because every time he looked at Taka, Turk's brother, he wondered why Turk had died and not Taka?

One outside activity of Turk's owner was, and still is, gardening. Naturally, he had a subscription for the organic gardening magazine, and perused through every article. In the April 1986 edition he came across an article by Judith Benn Hurley, "Calcium From Your Garden," and up popped the word oxalate. Imagine his surprise, an industrial chemical, a poison, in a magazine on organic gardening.

Once again the search was on. The owner wrote a letter to Ms. Hurley describing his research, the reason for it, and asked if she had anymore information on oxalates she could share. The reply he received provided him with more information than he could have hoped for. Her reply sent him to the library, to the section containing books on nutrition. He read many volumes and was amazed by the amount of information available on plant life and the effects of plant vitamins on maintaining human life. His effort was rewarded when he found a volume *Let's Get Well* by Adelle Davis, 1965. It contains the perfect finger print of Turk's death. Chapter 19, page 239 states the following:

> When both vitamin B6 and magnesium are undersupplied, the kidneys are further damaged by sharp crystals of oxalic acid combined with calcium, and as much as three-quarters of the kidney may be replaced by scar tissue. Children with oxalic acid kidney stones frequently have high blood pressure and kidneys so damaged that they become progressively worse, causing death from kidney failure early in life.

The owner's mind went back to information he had gathered concerning the use of beagles in testing because their organs are more like those of a child than any other animal. How true the statements, "love them to death" and also "kill them with kindness." The owner believed that he had inadvertently killed Turk by feeding him candy bars, soybean crackers, beets, carrots, and who-knows-what-else that might have been very high in oxalate, oxalic acid or both. He believed that these snacks saturated Turk's system to a point where Turk's kidneys could no longer function. When that happened, the acid began to destroy renal tissue. As the tissue was being destroyed, Turk's condition worsened until other vital functions were affected. Turk's owner also believed that since oxalates and oxalic acid suppress calcium, no healthy red blood cells were being produced. The blood in Turk's system had to have been totally saturated with oxalic acid. When all the renal tissue was destroyed, the kidneys shut down and swelling began due to edema. There was no hope for recovery.

Taka was not affected because he did not crave or eat soybean crackers, beets or carrots, nor the SNICKERS® brand candy bars with peanuts. When the owner realized what caused Turk's death, he put Taka on an oxalate/oxalic acid-free diet. Some weeks after putting Taka on the diet, the color of Taka's coat, which had faded, began returning to normal. Knowing that a human could suffer from an excess of oxalates and oxalic acid, the owner put himself on a similar diet as well.

Several significant events occurred beginning with the return of the color of Taka's coat while on the oxalate-free diet. The owner began to watch for signs in his own hair and noticed that his graying seemed to have at least slowed down. Since the owner was due for a physical, he checked into a clinic and stated he had some minor pain in his chest on the left side where he had muscles torn in a car accident many years earlier. During the exam, the doctor decided to be safe and ordered an EKG. In prepping for the EKG, the nurse shaved his chest where the transducer cups would be placed, and then with a small orbital sander removed some of the dead skin for better contact. Weeks after the exam when the hair began growing out, it was black instead of gray or white.

Many mornings before starting the oxalate-free diet, the owner would get out of bed with a dull backache, and occasionally it would really spasm when he would lean over the wash basin while brushing his teeth. He complained and swore he would get a new mattress, believing it to be the cause of the backaches. By the end of the day the ache would be gone and out of mind. When the backaches stopped, he realized it was his kidneys and knew it was the soybean crackers and nuts in the oriental mix and other related items that had raised his oxalate level to the point it began bothering his kidneys.

After retirement, Turk's owner was planning to move and some friends stopped by to visit. One evening while having cocktails with the friends, they began talking about health and age, etc. One of the ladies mentioned she needed bypass surgery, but it could not be scheduled because her red blood cell count was low, and the doctors could not get it to rise, even though she was on a third medication. Turk's owner's research had paid off. He gave his organic gardening magazine to the lady and urged her to read the article by Judith Benn Hurley. He explained to her that the reason her red cell count was low was because of her diet. She ate very little meat, a primary source of pyridoxine (vitamin B6), did not drink much soda pop, orange or pineapple juice (all high in citric acid), and only consumed alcohol in moderate quantities. Her diet contained items high in oxalic acid, like spinach, her favorite salad. The owner mentioned that in his research he had discovered there were three chemicals that would counteract the oxalic acid—pyridoxine hydrochloride (vitamin B6), citric acid, and alcohol. He gave her a handful of 50 mg vitamin B6 pills and suggested she take one immediately and then one a day for the first week, and then one every other day. Three weeks later she told him that the doctor had just scheduled her operation.

Turk's owner had also noticed that he did not have the recurring attacks of heart burn he had prior to changing his diet and taking vitamin B6. He thought it a great discovery.

Then, Turk's owner moved to Arkansas. His stepdaughter who is married and was living nearby, worked at a local hospital. One day she began running a high fever in the range of 104°–106°, went home, and went straight to bed. The fever fell, and the next couple of days she returned to work only to have the fever return after a couple of hours. She went home and the cycle repeated. She mentioned this to a doctor in the emergency room and a series of tests were ordered looking for a virus, an infection, even a tubular conception. Turk's owner became involved, because after listening to long, sometimes whispered conversations between his wife and stepdaughter, he asked what the trouble was. His wife explained what had happened and that the doctor was looking for some type of urinary tract or vaginal infection, but there were no positive cultures. When he heard that the stepdaughter experienced burning and irritation when urinating, he asked his wife why they did not think about diet. His stepdaughter was eating primarily salad bar meals loaded with oxalic acid. He had his wife immediately take a bottle of vitamin B6 pills to his stepdaughter with instructions to take two pills immediately, another one after twelve hours, and one a day after that for the next week. In two days her fever was gone, and she went back to work. After the third day all symptoms were gone and she was back to normal as best they could ascertain. Other people who complained of back pain without having muscle or spine problems found relief after Turk's owner advised taking vitamin B6.

One day while drying off after a shower, Turk's owner noticed a mole-type growth on the inside of his right thigh. He had not noticed it before, and shortly after that, a growth began at the end of his right eyebrow near the bridge of his nose. As the growth on the thigh became bigger, so did his curiosity. He picked at the growth until some of it came off and it bled. Now curiosity turned to concern. A month later the growth on the thigh reappeared and the growth on the eyebrow grew larger. He would check both growths every day and they were always on his mind. He believes it was his obsession with Turk that guided his thoughts to oxalic acid. This acid is readily available in foods people eat, so why would God put a substance in food He provided to sustain life, if that same substance by assaulting the kidneys can kill life? It just did not make sense. That question constantly ran through his mind begging to be answered. Night after night, hours were spent turning and tossing in restless sleep, searching and searching for an answer. He had read every article in every magazine he could get his hands on about foods thought to help in the fight against cancer, antioxidants, free radicals, and anti-rust in the blood. One night his mind stopped on one particular item. It was a sentence he had read about foods, and the importance they play in health and healing. "The acid in strawberries is thought to help prevent prostate cancer." Acid—there it was, that is the word that halted his mental computer. When he woke up, questions began running through his mind. If oxalic acid would destroy healthy renal tissue, could it possibly destroy sick tissue first? Is cancer not considered to be sick cells? Are these free radicals sick cells? What about antioxidants? Are there really different types of cancer, or are they a similar type of sick cell just in different parts of the body? Why are there different types of chemotherapies?

There were just too many questions. He had to go back and start with his initial question. He asked a dear friend, a devout Christian, whether the Bible states that God put everything on earth that man needs? At the same time he went on a very high oxalic acid diet and avoided citric acid and reduced his intake of pyridoxines and alcohol to a minimum. His dear friend came back and said she told her Bible class of his request. They searched the Bible and noted three places that mention God providing for all of man's needs. What is significant is that articles describing food groups for cancer prevention, especially the vegetable groups, name those that have significant amounts of oxalic acid as per USDA Bulletin #11 (Table I). At this time he became convinced it was not the beta carotene, the vitamin C, or anything else that was the cancer fighter—it was oxalic acid. Once again he started asking himself questions. Would oxalic acid destroy sick cells before healthy cells? The only answer he could come up with is the affirmative.

Hence, there is a need for an oxalic acid or oxalate composition and method of treatment for warm blooded animals including humans and pets.

SUMMARY OF THE INVENTION

In accordance with the present invention, an oxalic acid or oxalate composition and method of treatment of warm blooded animals including humans and pets is provided which includes at least one therapeutically effective form of oxalic acid or oxalate for controlling, treating, or managing neoplasia, tumors, brain tumors, cancer, growths, and the like, for preventing the new growth of different or abnormal tissues, or for otherwise therapeutically treating warm blooded animals including humans and pets. The therapeutically effective form of oxalic acid or oxalate is any oxalic acid or oxalate which provides the beneficial effect and is selected, for example, from the group of oxalic acid in a free acid, ester, lactone or salt form, oxalates including sodium oxalate, a nutritional supplement containing at least one form of oxalic acid or oxalate, oxalic acid dihydrate, anhydrous oxalic acid, oxamide, oxalate salts, natural or processed foods including molds, plants or vegetables such as parsley, chives, garlic, beets, carrots, spinach and the like containing at least one form of oxalic acid or oxalate, beverages, liquids or juices containing at least one form of oxalic acid or oxalate, additives containing at least one form of oxalic acid or oxalate, and combinations thereof. The composition may also contain a pharmaceutically acceptable carrier or diluent for the therapeutically effective form of oxalic acid or oxalate.

Also in accordance with the present invention a method is provided for controlling, treating or managing neoplasia, tumors, growths, cancers, abnormal tissues and the like in warm blooded animals including humans and pets including the steps of periodically administering a therapeutically effective dosage of a composition including at least one therapeutically effective form of oxalic acid or oxalate. The method may include the further step of reducing the intake of oxalic acid or oxalate blockers such as citric acid, ascorbic acid (vitamin C), pyridoxine hydrochloride (vitamin B6), calcium, alcohol, resins, clays, and combinations thereof. Oxalic acid or oxalate blockers also include dairy products containing calcium, fruits, coconut, beverages containing alcohol, ascorbic acid or citric acid, red meat or white meat of fowl containing pyridoxine hydrochloride, or other foods, nutritional supplements or beverages containing alcohol, citric acid, ascorbic acid, pyridoxine hydrochloride, and combinations thereof.

In accordance with the present invention, an "oxalic acid or oxalate blocker" is any mineral, chemical, compound, material, plant, food, beverage, additive, supplement or the like which blocks, inhibits, reduces, or binds with or otherwise reduces or eliminates the beneficial effect of oxalic acid or oxalate. For example, calcium from dairy products tends to bind with oxalic acid in the intestine and prevents the oxalic acid from being absorbed into the blood stream.

In accordance with another embodiment of the present invention, a composition is provided for controlling, treating or managing hyperplasia including swollen or enlarged prostate and the like for preventing new swelling or enlargement of tissues, or for otherwise therapeutically treating warm blooded animals including pets and humans and which includes at least one therapeutically effective form of oxalic acid or oxalate. Also, a method is provided for controlling, treating or managing hyperplasia including swollen or enlarged prostate, and the like, for preventing new swelling or enlargement of tissues, or for otherwise therapeutically treating warm blooded animals including pets and humans including the steps of periodically administering a therapeutically effective dosage of a composition of at least one therapeutically effective form of oxalic acid or oxalate. This method may further include the step of reducing the intake of oxalic acid or oxalate blockers.

In accordance with yet another embodiment of the present invention, a diet is provided for treating, controlling, and preventing cancer, tumors, neoplasia, and the like in warm blooded animals including pets and humans. The diet includes adding to the regular diet a dietary supplement of at least one therapeutically effective form of oxalic acid or oxalate. Further, the diet may include reducing the intake of oxalic acid or oxalate blockers.

In accordance with still yet another embodiment of the present invention, a veterinary composition is provided for controlling, treating or managing neoplasia, tumors, brain tumors, cancer, growths and the like, for preventing the new growth of different or abnormal tissues, or for otherwise therapeutically treating warm blooded animals including dogs and cats and includes a composition having at least one therapeutically effective form of oxalic acid or oxalate. The composition may further include a pharmaceutically acceptable carrier or diluent for the therapeutically effective form of oxalic acid or oxalate. A method is also provided for controlling, treating or managing neoplasia, tumors, growths, cancers or abnormal tissues in warm blooded animals including dogs and cats and includes the steps of periodically administering a therapeutically effective dosage of a veterinary composition containing at least one therapeutically effective form of oxalic acid or oxalate. The method may also include the further step of reducing the intake of oxalic acid or oxalate blockers.

In accordance with a further embodiment of the present invention, a composition for treating auto-immune related diseases such as HIV, SLE, AIDS, BSE, CFS and the like includes a therapeutically effective amount of at least one therapeutically effective form of oxalic acid or oxalate. Also, a method of treating, preventing or controlling auto-immune related diseases, preventing, lessening or controlling the destruction of the bodies immune system, or purifying the blood is provided which includes the steps of periodically administering a therapeutically effective amount of at least one therapeutically effective form of oxalic acid or oxalate.

In accordance with another embodiment of the present invention, a composition for counteracting the decomposition or reduction of oxalic acid or oxalate caused by radiation exposure, radiation treatment, X-rays, strong electromagnetic waves or fields, and the like, or for returning the bodies oxalic acid or oxalate level to at least a normal level following radiation treatment, X-rays, CAT-scans, MRI-scans, and the like is provided which includes a therapeutically effective amount of at least one therapeutically effective form of oxalic acid or oxalate. Also, a method for counteracting the decomposition or reduction of oxalic acid or oxalate caused by radiation exposure, radiation treatment, X-rays, strong electromagnetic waves or fields, and the like or for returning the bodies oxalic acid or oxalate level to at least a normal level following radiation treatment, X-rays, CAT-scans, MRI-scans, and the like is provided which includes the steps of administering a therapeutically effective amount of a composition including a therapeutically effective form of oxalic acid or oxalate following the treatment or exposure. The method may further include the steps of administering a therapeutically effective amount of at least one therapeutically effective form of oxalic acid or oxalate prior to the treatment or exposure. Further, the method may include the steps of decreasing or eliminating the ingestion or administration of one or more of oxalic acid or oxalate blockers.

In accordance with still yet another embodiment of the present invention, a treatment regimen for treating tumors, cancers, growths, neoplasia and the like including brain tumors, breast cancer, cervical cancer, and others is provided which includes the steps of reducing or eliminating the ingestion or administration of oxalic acid or oxalate blockers, administering or ingesting high dosages of at least one form of oxalic acid or oxalate to raise the blood or urine oxalic acid or oxalate level above normal levels, and after cleansing the blood of tumor, cancer, abnormal cells or the like, administering or ingesting a more moderate level of oxalic acid or oxalate to maintain a normal blood or urine oxalic acid or oxalate level. This regimen may further include the steps of administering or ingesting a moderate level of oxalic acid or oxalate blockers following the cleansing of the blood and without reducing the blood or urine oxalic acid or oxalate levels below normal.

In accordance with still another embodiment of the present invention, a therapeutic composition in cream or ointment form for topical administration of oxalic acid or oxalate is provided which includes at least one therapeutically effective form of oxalic acid or oxalate, a solvent, and a cream or ointment base.

In accordance with another embodiment of the invention, an improved pet food includes at least one therapeutically effective form of oxalic acid or oxalate in addition to conventional pet food ingredients. Another improved pet food of the present invention includes conventional pet food ingredients except for the elimination or reduction of oxalic acid or oxalate blockers. Yet another improved pet food of the present invention includes conventional pet food ingredients except for the elimination or reduction of oxalic acid or oxalate blockers and the addition of a therapeutically effective quantity of at least one therapeutically effective form of oxalic acid or oxalate.

A still further embodiment of the present invention includes a method of treating osteoporosis including the steps of increasing calcium intake while at the same time decreasing or eliminating oxalic acid or oxalate intake.

In accordance with still another embodiment of the present invention, a therapeutic composition for purifying the blood, treating BSE, HIV, CFS, AIDS, Hodgkin's disease, Parkinson's disease, multiple sclerosis, and the like, controlling, treating or eradicating abnormal cells, controlling, treating or effecting cholesterol, plaque and fat buildup in the cardiovascular system or the brain, maintaining good cardiovascular health and operation, or the like is provided which includes a therapeutically effective amount of at least one therapeutically effective form of oxalic acid or oxalate.

In accordance with yet another embodiment of the present invention, an oral rinse or mouthwash for smokers or snuff users for controlling, treating or managing neoplasia, tumors, cancers, growths and the like, for preventing the new growth of different or abnormal tissues, or for otherwise therapeutically treating the mouth area is provided which includes a dilute solution of at least one therapeutically effective form of oxalic acid or oxalate.

Also in accordance with the present invention, a method of manufacturing a dry processed dog food containing at least one form of oxalic acid or oxalate is provided which includes the steps of mixing a first slurry of conventional dog food ingredients together with a dilute solution of oxalic acid or oxalate to form an oxalic acid or oxalate containing second slurry, forming the second slurry into pellets, and then drying the pellets.

In accordance with yet another embodiment of the present invention, a composition for treating parvo virus in animals including canines is provided which includes a therapeutically effective amount of at least one therapeutically effective form of oxalic acid or oxalate.

In accordance with another embodiment of the present invention, a pharmaceutical composition to be administered orally to humans is provided which includes a mixture of a nontoxic ingestible carrier and a therapeutically effective form of oxalic acid or oxalate.

In accordance with still yet another embodiment of the present invention, an improved human or pet treat includes the addition of microgram amounts of at least one therapeutically effective form of oxalic acid or oxalate.

In accordance with another embodiment of the present invention, a composition for improving and maintaining good health in warm blooded animals includes a composition containing at least one therapeutically effective form of oxalic acid or oxalate.

In accordance with another aspect of the present invention, at least one form of oxalic acid or oxalate is used as a flavor enhancer, a preservative, a food additive, or a substitute for citric acid or ascorbic acid.

In accordance with another embodiment of the present invention, a method of enhancing or promoting the growth or the spread of tumors, growths, neoplasia and the like in warm blooded animals including test animals such as mice, rats, and the like is provided which includes the steps of reducing the intake of oxalic acid or oxalate, destroying or decomposing the oxalic acid or oxalate in the animal, and/or increasing the intake of oxalic acid or oxalate blockers.

In accordance with yet another embodiment of the present invention, a diet for promoting and maintaining good health in warm blooded animals including humans is provided which includes increasing the intake of foods containing oxalic acid or oxalate and reducing the intake of oxalic acid or oxalate blockers.

In accordance with yet another embodiment of the present invention, a method of inhibiting the therapeutic effect of oxalic acid or oxalate in warm blooded animals including test animals such as mice, rats, and the like is provided which includes the steps of increasing the ingestion or administration of oxalic acid or oxalate blockers such as calcium, alcohol, vitamin C, vitamin B6, citric acid, and destroying or decomposing some or all of the oxalic acid or oxalate in the animal.

In accordance with still another embodiment of the present invention, a method for inhibiting, preventing, treating, controlling or reversing the deleterious effects of high levels of oxalic acid or oxalate is provided which includes the steps of reducing the ingestion or administration of oxalic acid or oxalate, increasing the ingestion or administration of oxalic acid or oxalate blockers, monitoring the levels of oxalic acid or oxalate in the blood or urine, and adjusting the ingestion or administration of oxalic acid, oxalate and blockers thereof to achieve the desired oxalic acid or oxalate blood or urine levels.

Also in accordance with the present invention, a method of counteracting, inhibiting, treating, controlling, or reducing the deleterious effects of high levels of oxalic acid or oxalate is provided which includes the steps of administering or ingesting a therapeutically effective amount of vitamin B6.

In accordance with another embodiment of the present invention, a method of treating a warm blooded animal is provided including the steps of determining the oxalic acid or oxalate blood and/or urine levels of the animal, comparing the determined blood and/or urine level with a scale indicating below normal, normal, and above normal levels, increasing the administration or ingestion of oxalic acid or oxalate if the blood and/or urine level is below normal, reducing the ingestion or administration of oxalic acid or oxalate blockers if the blood and/or urine level is below normal, maintaining current ingestion or administration levels of oxalic acid, oxalate, or blockers thereof if the blood and/or urine oxalic acid or oxalate levels are normal, reducing the ingestion or administration of oxalic acid or oxalate if the blood and/or urine levels are above normal, and increasing the ingestion or administration of oxalic acid or oxalate blockers if the blood and/or urine level is above normal. This method also includes the adjustment of the below normal, normal and above normal scale levels or categories for differing health conditions.

In accordance with still another embodiment of the present invention, a multi-vitamin includes the addition of at least one therapeutically effective form of oxalic acid or oxalate in addition to conventional components. Also, a multi-vitamin and mineral supplement of the present invention includes the addition of at least one therapeutically effective form of oxalic acid or oxalate in addition to conventional components. An alternative multi-vitamin or multi-vitamin and mineral supplement of the present invention includes not only an addition of at least one therapeutically effective form of oxalic acid or oxalate but also the reduction or elimination of oxalic acid or oxalate blockers from the conventional components thereof.

In accordance with still another embodiment of the present invention, a therapeutic composition is provided which is made up of a conventional process food item such as bread, cereal or other prepared food including the addition of a therapeutically effective amount of at least one therapeutically effective form of oxalic acid or oxalate. Another therapeutic composition of the present invention is a sourdough bread made from flour, water, yeast, sourdough starter, and at least one therapeutically effective form of oxalic acid or oxalate.

In accordance with another embodiment of the present invention, a method of delaying, preventing, controlling or treating the onset of Alzheimer's Disease, Hodgkin's Disease, Parkinson's Disease, Multiple Sclerosis, Creutzfeldt-Jakob Disease, and the like, lessening the effects of the disease, or improving the quality of life of a person suffering from the disease is provided which includes the steps of periodically administering a therapeutically effective amount of at least one therapeutically effective form of oxalic acid or oxalate.

In accordance with still another embodiment of the present invention, a canine and feline urine oxalate level scales include below normal, normal, and above normal level categories depending on the weight and physical condition of the animal and provide a quick-ready reference for a veterinarian or pet owner to test urine oxalate levels and adjust the oxalic acid or oxalate intake in the diet, food or treatment of the canine or feline accordingly.

In accordance with another embodiment of the present invention, a method for causing the sloughing off of the inner surface of the intestinal membrane in a warm blooded animal including humans is provided which includes the steps of administering daily doses of a therapeutically effective amount of at least one therapeutically effective form of oxalic acid or oxalate for a sufficient period to cause the sloughing off of the interior surface of the intestinal membrane and thereby removing old bacteria, food, waste, intestinal cells, membrane, and the like.

In accordance with another aspect of the present invention, a method of treating or preventing oxalate nephrosis in animals including dogs, goats, humans, cattle and the like is provided which includes the steps of periodically administering a therapeutically effective amount of at least one therapeutically effective oxalic acid or oxalate blocker.

In accordance with another embodiment of the present invention, a dilute solution of oxalic acid is used as a composition for cleaning oral or dental bridgework, a composition for cleaning a toothbrush, a composition for cleaning and rinsing the interior surfaces of the mouth and teeth, a mouthwash, a tartar control rinse, an antibacterial rinse, or combinations thereof.

In accordance with still yet another embodiment of the present invention, a test kit for detecting the oxalate level in urine of warm blooded animals including humans is provided which includes a sample holder and a liquid reagent which upon addition of a selected quantity of reagent to a sample of urine in the sample holder provides a colormetric indication of the presence or absence of oxalate.

In accordance with another embodiment of the present invention, a dilute solution of oxalic acid is used as a meat tenderizer.

In accordance with another embodiment of the present invention, a dietary supplement for everyday optimum nutritional balance is provided which includes between 0.5 micrograms to 1.5 grams of oxalic acid or oxalate.

In accordance with still another embodiment of the present invention, a test kit for detecting the presence and quantity of oxalic acid in a blood sample of a warm blooded animal including humans is provided which includes a sample support surface, a reagent, and a mixing container for mixing together a blood sample and reagent to allow the reagent to undergo a color change and provide a colormetric determination of the presence and quantity of oxalic acid in the sample.

In accordance with another embodiment of the present invention, a method of treating warm blooded animals including humans and pets is provided which includes the steps of testing the animal to determine the blood or urine oxalic acid or oxalate levels, administering oxalic acid, oxalate, or blockers thereof depending on the tested levels, and periodically monitoring the blood or urine oxalic acid or oxalate levels and adjusting the administration of oxalic acid, oxalate, or blockers thereof.

In accordance with an exemplary embodiment of the present invention, at least one form of oxalic acid or oxalate is used as a nutritional supplement to aid in the control, treatment or management of neoplasia.

In accordance with another exemplary embodiment of the present invention, at least one form of oxalic acid dihydrate is used to treat tumors in warm blooded animals.

In accordance with another aspect of the present invention, at least one form of oxalic acid or oxalate is used to prevent the new growth of different or abnormal cells or tissue.

In accordance with another embodiment of the present invention, oxalic acid or oxalate is used to increase energy and add to the quality of life in animals including humans.

In accordance with another embodiment of the present invention, at least one form of oxalic acid or oxalate is administered orally, by direct injection, intravenously, or topically.

In accordance with another embodiment of the present invention, oxalic acid dihydrate is administered as a food additive.

One object of the present invention is the provision of a novel therapeutic composition including a pharmaceutically acceptable carrier or diluent containing a therapeutically effective amount of at least one therapeutically effective form of oxalic acid or oxalate. Another object of the present invention is the provision of a method of therapeutically treating warm-blooded animals with such a therapeutic composition.

A further object of the present invention is the provision of an oxalic acid or oxalate pharmaceutical.

Another object of the invention is the use of oxalic acid in lieu of citric acid as a flavor enhancer and/or preservative in shelf/prepared food products.

Another object of the present invention is the provision of a method of treating animals including humans with at least one form of oxalic acid or oxalate.

Still another object of the present invention is the provision of a method of treating warm-blooded animals with selected levels of oxalic acid or oxalate, vitamin B6, citric acid, vitamin C, calcium, alcohol, and/or combinations thereof.

Another object of the present invention is the provision of a method of treating cancer in humans or other animals with an oxalic acid or oxalate.

Yet another object of the present invention is the provision of a veterinary composition of oxalic acid dihydrate.

Another object of the present invention is the provision of a method of treating neoplasia with at least one form of oxalic acid or oxalate.

Another object of the present invention is the provision of a method of treating a warm-blooded animal afflicted with tumor cells sensitive to an oxalic acid or oxalate compound including administering to the animal an oncolytic amount of the oxalic acid or oxalate compound.

A more particular object of the present invention is the provision of a novel anti-tumor agent, processes for its preparation, compositions containing it, and methods of treating tumors with it.

Another object of the present invention is an oxalic acid or oxalate composition and method for treating autoimmune related diseases such as AIDS, HIV, SLE, BSE, CFS, and the like.

Another object of the present invention is the provision of an oxalic acid or oxalate composition and method for counteracting the destruction of oxalic acid by radiation treatment, X-rays, and the like.

Another object of the present invention is the provision of a composition for improving and maintaining good health in warm blooded animals and including at least one therapeutically effective form of oxalic acid or oxalate.

Still another object of the present invention is the provision of a flavor enhancer, preservative, food additive, citric acid substitute and the like made up of at least one form of oxalic acid or oxalate.

Yet another object of the present invention is the provision of a method of enhancing or promoting the growth or the spread of tumors, growths, cancers, and the like in warm blooded animals such as test animals by reducing the intake of oxalic acid or oxalate, destroying or decomposing the oxalic acid or oxalate in the animal, and/or increasing the intake of oxalic acid or oxalate blockers.

A further object of the present invention is the provision of a diet for promoting good health in warm blooded animals including increased quantities of oxalic acid or oxalate, and/or reducing or eliminating the intake of oxalic acid or oxalate blockers.

Another object of the present invention is the provision of a method of inhibiting the therapeutic effect of oxalic acid or oxalate in warm blooded animals such as test animals by increasing the ingestion of oxalic acid or oxalate blockers, and/or destroying or decomposing some or all of the oxalic acid or oxalate in the animal.

Still another object of the present invention is the provision of a method for inhibiting, preventing, treating, controlling or reversing the deleterious effects of high levels of oxalic acid.

A more particular object of the present invention is the provision of a method of counteracting, inhibiting, treating, controlling or reducing the deleterious effects of high levels of oxalic acid by administering or ingesting a therapeutically effective amount of vitamin B6.

Yet another object of the present invention is the provision of a method of treating warm blooded animals including the steps of determining the oxalic acid or oxalate blood and/or urine levels of the animal, comparing this determined level with a scale indicating below normal, normal, and above normal oxalic acid or oxalate levels, and increasing or decreasing the administration or ingestion of oxalic acid, oxalate, or blockers thereof depending on the determined oxalic acid or oxalate levels.

A further object of the present invention is the provision of a multi-vitamin or multi-vitamin and mineral supplement including at least one therapeutically effective form of oxalic acid or oxalate.

Still another object of the present invention is the provision of a processed food item including a therapeutically effective amount of at least one therapeutically effective form of oxalic acid or oxalate.

Yet another object of the present invention is the provision of a method of delaying, preventing, controlling, or treating Alzheimer's Disease, Hodgkin's Disease, Parkinson's Disease, and the like lessening the effects of the disease, or improving the quality of life of a person suffering from the disease.

A more particular object of the present invention is the provision of a canine and/or feline urine oxalate level scale providing a quick-ready reference for below normal, normal, and above normal oxalate levels based on the weight and/or condition of the animal.

Another object of the present invention is the provision of a method for causing the sloughing off of the inner surface of the intestinal membrane in warm blooded animals.

Still another object of the present invention is a method of treating or preventing oxalate nephrosis in animals.

Yet another object of the present invention is the provision of a composition for cleaning oral or dental bridgework, toothbrushes, the interior surfaces of the mouth and teeth, and the like.

A further object of the present invention is the provision of a mouthwash, tartar control rinse, or antibacterial rinse including a small amount of oxalic acid.

Another object of the present invention is the provision of a test kit for detecting and/or quantifying the oxalic acid or oxalate level in the blood and/or urine of a warm blooded animal.

Still another object of the present invention is the provision of a meat tenderizer made up of a dilute solution or concentration of oxalic acid.

Yet another object of the present invention is a dietary supplement for every day optimum nutritional balance including oxalic acid or oxalate.

A more particular object of the present invention is the provision of a composition for controlling, treating or managing neoplasia, tumors, cancers, growths and the like, for preventing the new growth of different or abnormal cells or tissues, or for otherwise therapeutically treating warm blooded animals including pets and humans utilizing a composition and method including at least one therapeutically effective form of oxalic acid or oxalate.

A further object of the present invention is the provision of a composition and method for controlling, treating or managing hyperplasia and the like, for preventing new swelling or enlargement of tissues, or for otherwise therapeutically treating warm blooded animals including pets and humans using a composition including at least one therapeutically effective form of oxalic acid or oxalate.

Another object of the present invention is the provision of a diet for treating, controlling and preventing cancer, tumors, neoplasia, growths and the like in warm blooded animals including the addition of a dietary supplement of at least one therapeutically effective form of oxalic acid or oxalate. The diet may also include the reduction in the intake of oxalate acid or oxalate blockers.

Still another object of the present invention is the provision of a veterinary composition and method for controlling, treating or managing neoplasia, tumors, cancers, growths and the like, for preventing the new growth of different or abnormal cells or tissues or for otherwise therapeutically treating warm blooded animals including dogs and cats utilizing a composition including at least one therapeutically effective form of oxalic acid or oxalate.

Yet another object of the present invention is the process for preparing an anti-tumor agent including the steps of mixing at least one therapeutically effective form of oxalic acid or oxalate with a pharmaceutically acceptable carrier or diluent.

A further object of the present invention is a composition and method for treating autoimmune related diseases such as HIV, SLE, AIDS, BSE, CFS, and the like by administering a therapeutically effective amount of at least one therapeutically effective form of oxalic acid or oxalate.

Another object of the present invention is the provision of a composition and method for counteracting the decomposition or reduction of oxalic acid or oxalate caused by radiation exposure, radiation treatment, X-rays, strong electromagnetic waves or fields, and the like using a therapeutically effective amount of at least one therapeutically effective form of oxalic acid or oxalate.

Still another object of the present invention is the provision of a treatment regimen including the steps of reducing or eliminating the intake of oxalic acid or oxalate blockers, administering high dosages of oxalic acid or oxalate until the blood is cleansed of tumor, cancer or abnormal cells, and thereafter administering a moderate level of oxalic acid or oxalate to maintain a normal blood or urine oxalic acid or oxalate level.

Yet another object of the present invention is an improved pet food including a therapeutically effective quantity of at least one therapeutically effective form of oxalic acid or oxalate and/or the elimination or reduction of oxalic acid or oxalate blockers.

A more particular object of the present invention is a composition and method for treating a person suffering from osteoporosis and tumors, cancers, growths, neoplasia and the like.

A further object of the present invention is the provision of an oral rinse or wash for smokers or snuff users including a dilute solution of at least one therapeutically effective form of oxalic acid or oxalate.

Another object of the present invention is a method of manufacturing dog food containing at least one form of oxalic acid or oxalate.

Still another object of the present invention is the provision of a composition and method for treating parvo virus in animals.

Yet another object of the present invention is a pharmaceutical composition to be administered orally to humans including a mixture of a non-toxic ingestible carrier and a therapeutically effective form of oxalic acid or oxalate.

Other objects and further scope of the applicability of the present invention will become apparent from the detailed description to follow.

DETAILED DESCRIPTION OF THE PREFERRED EMBODIMENTS

Figure 1:
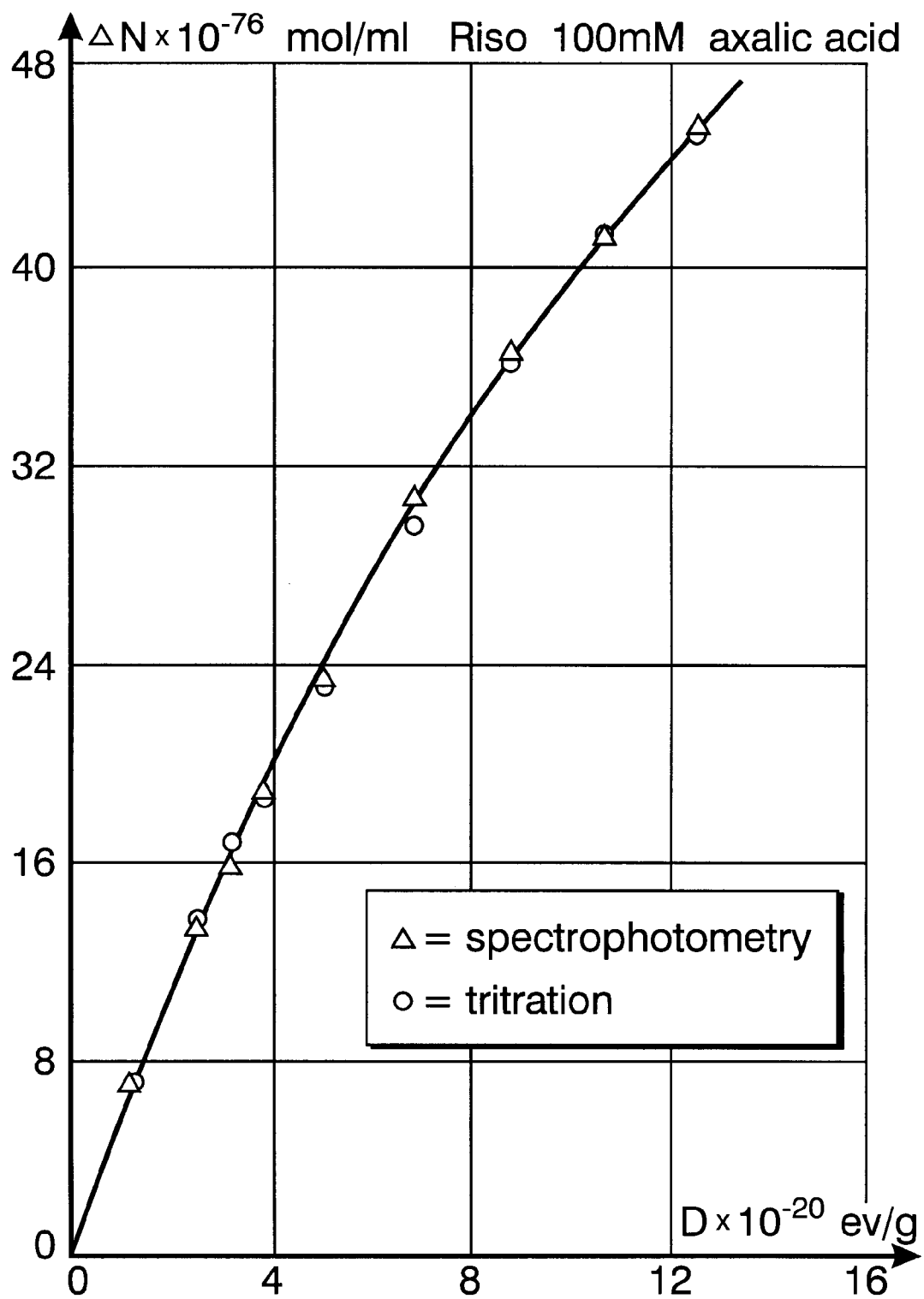
FIG. 1 is a graphical illustration of a decomposition curve for a 100 mM oxalic acid solution by $^{60}$Co.

After placing himself on a high oxalic acid or oxalate diet, the growth on Turk's owner's thigh began to disappear and shortly thereafter the growth on his eyebrow as well. Eventually both growths were completely gone. Another sign of the result of the high oxalic acid diet was the disappearance of a couple of polyps around the anal orifice. These had appeared when he went on the low oxalate/low oxalic acid diet, and now when he reversed the diet these growths disappeared.

Later, his own daughter informed him that her mother was having a lot of stomach or digestive problems and was due for exploratory surgery. During the operation they discovered cancer in the abdominal cavity and removed all possible, estimated at 80w. There was cancer in the bladder, and they planned an extensive chemotherapy program. However, a specialty lab in California which received the tissue sample, determined it was a rare type of cancer, with no known treatment. His daughter, who was at her mother's side constantly, agreed to try his oxalic acid procedure. With his instruction and the help of a juicer, she prepared a mixture of carrots, spinach, parsley, and chives. He suggested she try to get her mother to drink six to eight ounces of the mixture at least three times a day. At the start, her mother complained of the taste, so he suggested she mix some V8® juice with the mixture to enhance the flavor. This worked, and her mother began to drink the mixture. He felt that by having it in liquid form, more oxalic acid would enter her system more rapidly and begin to attack the sick cells. On the third day after her mother began drinking the mixture, his daughter talked with the nurse who said, "In the morning when she took the patient's vital signs they were the best since the patient had come to the hospital. Her temperature was down, blood pressure was down, and pulse rate was near normal." In addition, the yellowish skin color began to change. Then, for reasons unknown, her mother stopped drinking the mixture. Shortly after that her mother passed away.

Later, Turk's owner learned of a close friend who had prostate cancer, initially treated with a radiation implant which failed to keep the growth in check, and now would be undergoing chemotherapy. He urged his friend with prostate cancer to try his oxalic acid dietary treatment. He sent an explanatory letter with copies of articles about the vegetables along with a list of items containing oxalates and oxalic acid. Later, he talked with his friend who gave him some revealing data. Prior to starting the oxalic acid dietary treatment, his friend had been to an oncologist because the cancer was spreading into the pelvic area and his PSA count was 350. When his friend returned to his primary care physician months later after being on the oxalic acid diet, he was feeling better, his PSA was down to 246, and the doctor was surprised because he did not think his patient would survive long enough to see him again. It seemed the doctor knew the chemotherapy would not work and it may have been given just so his friend would not despair. Turk's owner sent a copy of the Judith Been Hurley article to his friend and believed that low calcium in the bone marrow was probably the reason his friend with prostate cancer was tired and felt pain in the thigh and pelvic area.

A research associate joined Turk's owner, the Applicant, in trying to better establish the relationship between oxalic acid and pyridoxine hydrochloride (vitamin B6) and oxalic acid treatment for the reduction of tumors. The research associate volunteered his Irish Setter, a 70–75 lb., 14 year-old specimen which had a very noticeable tumor on the mouth and had been diagnosed with multiple tumors which a biopsy confirmed to be melanoma (skin cancer). The oral tumor was in an area easily examined. The oral tumor had been removed several years ago, when it was confirmed as malignant, but it had grown back. The question was posed if a high oxalic acid or oxalate diet supposedly works on humans, would it not also work on this dog? They felt confident, since *The Merck Manual* does state that 90% of cancers are due to environment and nutrition. And so, they embarked on taking the Setter off canned dog food (high in pyridoxines) and feeding a regular dry high protein dog food mixed with three or four boiled carrots and topped with chopped parsley. The canine was started on a diet of three or four medium sized boiled carrots, mixed with approximately 1½ pounds of dry dog food. Three to five days after starting on the diet, the canine showed an improvement in appetite and energy. After three weeks of being on this diet, there was a noticeable reduction in size and appearance of the tumor on the canine's mouth. Almost a month after starting on the above diet, the canine's diet was changed to a mixture of about one pound of boiled carrots, one teaspoon of garlic, one-quarter cup chopped fresh parsley, and one and one-half pounds of dry dog food containing no citric acid. This diet was varied based on the canine's condition with the mouth tumor being measured and recorded by a veterinarian. The mouth tumor exhibited expansion or swelling and reduction cycles. The canine's urine was tested for oxalate count and a result showed about 50 mg per liter of oxalic acid.

After about five months on this diet, the canine produced feces including mucous and intestinal membrane. Upon this happening all oxalic acid or oxalate addition to the canine's diet was stopped. It is believed that a high level of oxalic acid or oxalate intake causes a sloughing off of the interior surface of the small intestine including old bacteria, food, waste, and intestinal cells and membrane. After about a month, urine was drawn from the canine to test for oxalate count the canine's oxalic acid urine count was reduced to 24 mg/L. Three days later, the canine was restarted on a diet having about 1 gram of oxalic acid added to one pound of dry dog food. A canine urine oxalic acid scale was calculated based on a scale of 0–40 mg/L for a 70 kg human, and adjusting this for a 25 kg canine to have a desired range of about 0–14 mg/L. The canine was started on a new diet of approximately one and one-half pounds of dry dog food to 1 gram of oxalic acid dihydrate dissolved in about three ounces of water and mixed together and adding one-half can of Pedigree® brand canned dog food (6½ oz. can) to add protein to the diet. A little more than two weeks later the diet was changed to reduce the oxalic acid dose to 500 mg per day and the canine was given four beef strips (approximately 25 grams) with 27% protein each evening. Thirty days later the dose was dropped to 300 mg oxalic acid/day. Two weeks later the dose was dropped to 50 mg oxalic acid/day. Two weeks later the dose was dropped to 20 mg oxalic acid per day which was maintained till the animal was euthenized. The canine's mouth tumor had reduced in size in an eleven month period. The oxalic acid dihydrate was purchased from Swift Chemical Company, Rogers, Ark., and dissolved in water to use as a food additive to the canine diet.

Much to their surprise, the dog seemed to crave the carrots and parsley. The Setter's activity increased steadily to the point where he actively competed with a four-year-old Doberman and a nine-month-old Rottweiler. The diet was working. What was once a large saggy sack of black tissue visibly hanging from the Setter's mouth changed to a considerably smaller and firmer growth. The reduction in the growth of the oral tumor slowed over time; however, it must be remembered that the tumor took nearly six years to achieve the mass it once was. They continued to monitor the Setter's condition, and felt that the reduction in the size of the tumor was a positive sign that the oxalic acid or oxalate was working. An autopsy of the Irish Setter revealed the malignant melanoma with metastasis, adrenal gland pheochromocytoma, acute cystitis, the urinary bladder mucosa appeared diffusely thickened, granular and hemorrhagic in appearance with the presence of moderate amounts of a turbid reddish-brown urine, a large encapsulated necrotic mass within the omental adipose tissue, with no other significant gross lesions noted within other areas of the oral cavity, larynx, esophagus, trachea, lungs, heart, spleen, kidneys, musculoskeletal system, and gastrointestinal tract. Hence, it appears that the oxalic acid or oxalate diet did not damage any of the dog's organs or kidneys. It is believed that the lesions (scars) in the lungs of the canine, may indicate that oxalic acid or oxalate had eliminated growths in the lungs.

In accordance with another case study, a dog at a pound was given one gram of oxalic acid dihydrate in a gelcap one hour prior to meal time for seven days with no adverse effects. The dog's appetite increased as well as energy and activity.

In accordance with another case study a human adult female subject with possible cervical cancer found multiple growths on her cervix by self-examination. The subject started on an increased oxalic acid or oxalate and reduced oxalic acid or oxalate blocker diet, and in less than one month she reported that the smallest growth was reducing in size. The subject remained very strictly on the diet and a week later reported that the smallest growth was gone with only a rough spot remaining. A few days later the subject reported that the next size growth seemed to be reducing. Less than a month later, the subject reported that the large growth was considerably reduced. This process continued and less than a year after starting on the increased oxalic acid or oxalate diet, the subject reported that one small growth remained which was only noticeable during her menstrual period.

In accordance with another case study, an adult male human subject suffering from a brain tumor, had been through all the different conventional treatments including surgery, chemotherapy, and radiation treatment. The tumor was never totally removed and remained malignant. The subject was told of the possible beneficial effects of oxalic acid or oxalate and began on a treatment regimen of four heaping soup spoons of dried parsley daily and a reduction of oxalic acid or oxalate blockers. This should equate to approximately four grams of oxalic acid per day. Three to four months later, the subject had a CAT scan where the tumor was examined and did not show any growth. The subject also had visible signs of noticeable improvement in health. Approximately six months after starting on the enhanced oxalic acid or oxalate diet, the subject was much more active and friendly towards others. Approximately eight months after starting on the enhanced oxalic acid diet the subject was very excited about the diet, feeling much better. The subject had expected and experienced the toxic effects of indigestion, diarrhea, and the sloughing off of the interior surface of the intestine. The subject also indicated that the tumor was in the inactive stage. Also the subject indicated that his memory and thinking capability had returned and he could now accomplish functions he could not prior to following the diet. He was in the process of rebuilding an engine, replacing a carburetor, changing an oil pan, changing the oil and spark plugs, and other activities that prior to starting on the enhanced oxalic acid or oxalate diet were impossible.

Doctors had not given this patient much time to live, and it is believed that the enhanced oxalic acid or oxalate diet with reduced blockers had treated, controlled, or otherwise beneficially affected his brain tumor and overall health. He was still alive and functioning better after nine months.

An adult female in her sixties was terminally ill with leukemia with tumors in her lymph nodes and she had stopped chemotherapy treatment. She was told about the possible beneficial effect of oxalic acid or oxalate and started on a daily intake of about 1 to 1½ g/day oxalic acid or oxalate and almost no oxalic acid or oxalate blockers. It was hard for her to swallow so she was on a liquid diet because of the swelling of the lymph nodes in and around her mouth and throat. After 5–7 days of administration of oxalic acid or oxalate the dilute solution she was able to eat again due to the shrinkage of tumors in the lymph nodes. This dramatic effect in such a short time indicates that the intake of oxalic acid was treating her condition or disease and benefiting the individual.

In another case study, an adult female was diagnosed with a tumor (endometrial) in the uterus. The tumor was removed by laser and she was to undergo chemotherapy. She heard of the oxalic acid treatment of the present invention, and went on the diet having increased intake of oxalic acid or oxalate and reduced intake of oxalic acid or oxalate blockers. After several months of being on the diet, her blood tests were negative on cancer and she did not have to undergo chemotherapy.

In accordance with another case study, a Doberman pincher was diagnosed with bone cancer (sarcoma) of the left hind leg. The dog had previously been put on medication for arthritis because it would not use or lower its left hind leg. After being diagnosed with cancer confirmed with X-ray, the dog was placed on a diet of oxalic acid enhanced dogfood containing about 2 grams of oxalic acid dihydrate dissolved in water and added to conventional dry dogfood. Within 4 days, the dog had lowered its left hind leg and used it frequently in activity with a companion dog. A few days later, the dog began taking steps on the left hind leg with a slight limp. The dog's condition continued to improve and it's diet was changed to reduce the oxalic acid to about 1 gram of oxalic acid/per day. After a couple of weeks the dog's condition continued to improve so the dosage of oxalic acid was reduced to about 500 mg/per day. The dog appears to be walking with no pain and an X-ray revealed an increase in bone material in the area of the sarcoma and a decrease or reduction in the size of the area affected by the sarcoma. After being on the oxalic acid diet for about 30 days, the dog appeared to have no pain during physical exam and was walking normally.

In another case study, an adult female was diagnosed with stomach cancer and scheduled for surgery. She began the increased oxalic acid or oxalate and reduced oxalic acid or oxalate blocker diet and when she went in to have the surgery done, they discovered that her tumor had turned to liquid. Her diet or treatment regimen included a low intake of red meat or white meat of fowl, a low intake of soda pop or other beverages containing citric acid, a low intake of foods containing citric acid, an intake of about 4 ounces of carrot juice per day with 2 ounces taken in the morning and 2 ounces in the evening, and a low intake of alcohol. Apparently, the oxalic acid may have turned the tumor cells into a liquid and all that was necessary was for the liquid to be drained.

In another case study, an adult female having breast cancer started on a high oxalic acid or oxalate and low oxalic acid or oxalate blocker diet. The growth of the cancer was reduced and in less than 2 months of being on the diet her bloodwork showed a large reduction in the cancer in the blood and that the cancer was in regression. Her condition improved so much so that the doctors stopped chemotherapy treatment.

In another case study an adult female with breast cancer, she went on a diet including an intake of about 4 ounces of carrot juice per day along with chicken broth. In about 8 weeks she was sent home from the hospital, she was walking, went to the mall and was eating potato chips. Previously, she had been hospitalized and on a liquid diet.

In accordance with another case study, an adult female suffering from breast cancer went on an increased oxalic acid diet, stopped using the microwave oven to cook foods, stopped chemotherapy treatments, cut CAT-scans down to once a month, and in a short time her blood was tested and showed that it was clean of cancer cells and the breast cancer appeared to have stopped growing.

Based on this history, it is believed that oxalic acid or oxalate will, at a minimum, reduce the size of tumors; especially if pyridoxine hydrochloride, citric acid, ascorbic acid, calcium and alcohol are eliminated from the diet as much as possible. This dietary procedure needs to be continued until the tumor or growth is eliminated. If the individual experiences backaches due to kidney irritation, urinary tract irritations, and/or severe heartburn, vitamin B6 (pyridoxine hydrochloride) can be taken to help eliminate the discomfort. Since calcium, pyridoxine hydrochloride, citric acid, ascorbic acid and alcohol block oxalic acid or oxalate, the individual should work his/her dietary therapy up to the point of experiencing the discomforts stated and then back off slightly from oxalic acid or oxalate intake. It is also believed that the converse is also true—insufficient oxalic acid or oxalate may allow tumors to grow.

This invention relates generally to methods and compositions containing oxalic acid or oxalate or related compounds for providing therapeutic effects such as the control, prevention, or treatment of cancer, tumors, neoplasia, etc. It was initially discovered that a lack of oxalic acid or oxalate in the diet of a human, allowed or promoted the growth of tumors, growths, or other neoplasia. It was then discovered that the ingestion or administration of a therapeutic quantity of oxalic acid, oxalate or foods containing high levels of oxalic acid or oxalate can deter, reduce, or prevent the growth or spread of cancer, tumors, or other neoplasia.

It has also been discovered that the therapeutic effect of oxalic acid or oxalate can be inhibited by an increased ingestion or administration of oxalic acid or oxalate blockers including, for example, calcium, alcohol, citric acid, ascorbic acid (vitamin C), pyridoxine hydrochloride (vitamin B6), etc. Other oxalic acid or oxalate blockers include binding agents such as clay, resins, and indigestible fibers. Radiation, strong electromagnetic waves or fields, electron bombardment, excessive heat, and bases such as sodium bicarbonate serve to decompose, neutralize or otherwise reduce the beneficial effect of oxalic acid. There may also be pharmaceuticals which interfere with the absorption or beneficial activity of oxalic acid or oxalates. Also, the therapeutic effect of oxalic acid or oxalate can be enhanced by decreasing or eliminating the ingestion or administration of one or more of these blockers and/or increasing the ingestion of oxalic acid or oxalate. Oxalic acid or oxalate enhancers which increase the beneficial effect of oxalic acid or oxalate include longchain fatty acids and the like which bind with or otherwise eliminate oxalic acid blockers such as calcium.

High levels of oxalic acid or oxalate can produce side effects of diarrhea, indigestion, damage to the digestive tract, and kidney damage or renal failure. Hence, prolonged ingestion or administration of high quantities of oxalic acid or oxalate should be avoided so that the beneficial therapeutic effect of the reduction, control, or treatment of tumors, cancers, and neoplasia can be enjoyed without harm to other systems or parts of the body.

Oxalic acid or ethanedioic acid ($C_2H_2O_4$), is a dicarboxylic acid and is present in many plants and vegetables, notably in those of the Oxalis and Rumex families, where it often occurs in the cell sap of the plants as the potassium or calcium salt (oxalate, Tables I–IV). Oxalic acid is also a product of the metabolism of many molds. Several species of Penicillum and Aspergillus convert sugar into calcium oxalate with a 90% yield under optimum conditions. Oxalic acid is also made by passing carbon monoxide into concentrated NaOH or heating sodium formate in the presence of NaOH.

Oxalic acid dihydrate, monoclinic tablets, prisms, and granules are considered poisonous. Anhydrous oxalic acid is crystallized from glacial acetic acid and is orthorhombic with the crystals being pyramidal or elongated octahedra.

Oxalic acid is listed as being caustic and corrosive to the skin and mucous membranes. Ingestion may cause severe gastroenteritis, with vomiting, diarrhea, or melena. Renal damage can occur as a result of formation of excessive calcium oxalate crystals. Convulsions, coma, or death from cardiovascular collapse can also occur.

Common uses of oxalic acid include as an analytical reagent, in calico printing and dying, for bleaching straw and leather, removing paint or varnish, rust or ink stains, cleaning wood, and manufacturing oxalates, blue ink, celluloid, intermediates and dyes, in metal polishes, in purifying methanol, for decolorizing crude glycerol, for stabilizing hydrocyanic acid, as a general reducing agent, in ceramics and pigments, in metallurgy as a cleanser, in the paper industry, in photography, in process engraving, in rubber manufacturing, in making glucose from starch, as a condensing agent in organic chemistry, and as a veterinary hemostatic agent when mixed in 5% solution with 5% malonic acid.

As described in "Oxalic Acid in Biology and Medicine" by A. Hodgkinson, 1977, oxalic acid was formerly used intravenously as a hemostatic agent and topically as an antiseptic in man and other animals but this was discontinued because of its toxicity and the danger of precipitating insoluble calcium oxalate in the tissues. Oxalic acid is a relatively strong acid having a first dissociation constant being exceeded by that of only a few halogen-substituted carboxylic acids. Oxalic acid forms neutral and acid salts with monovalent metals and ammonia. Oxalic acid forms a number of oxalates or salts including calcium oxalate, potassium oxalate, sodium oxalate, strontium oxalate, magnesium oxalate, and the like. Oxalic acid also inhibits the activity of a number of enzymes possibly due to the competition between oxalate and a structurally similar substrate of the enzyme. Precipitation as the calcium salt is the classical method of separating oxalic acid from other substances. Although calcium oxalate is generally considered to be an insoluble salt this is a relative term and its solubility in water is actually 6–7 mg/l at room temperature. Biological fluids contain many substances that affect the solubility or rate of crystallization of calcium oxalate or co-precipitate with the salt. For example, magnesium, polyphosphates and other polyelectrolytes affect the solubility or rate of crystallization of calcium oxalate while phosphate and sulphate ions, uric acid and citric acid co-precipitate with the salt.

Also as described in "Oxalic Acid in Biology and Medicine", oxalic acid and its salts are widely distributed among the higher plants. Oxalic acid is sometimes present in plants as the free acid, but more usually, however, it is present as a soluble or insoluble salt, for example, the acid and neutral sodium and potassium salts and the ammonium salt. Calcium oxalate is the most common insoluble salt but relatively large amounts of magnesium oxalate occur together with calcium oxalate in plants such as beetroot, spinach, and buckwheat. Under conditions of calcium deficiency, strontium, magnesium, or barium oxalate can be substituted for calcium oxalate in a wide variety of plant species depending upon the mineral environment.

Further, as mentioned in "Oxalic Acid in Biology and Medicine", there have been many studies of the oxalate content of individual foodstuffs (see Tables I–IV), but few estimates have been made of the total daily intake of oxalate by animals or man (see Table V). This is surprising in view of the effect of oxalate on calcium availability and the high incidence of calcium oxalate renal stones in many parts of the world. As shown in Table V, the reported numbers for daily oxalate intake range from 70–980 mg/per day of anhydrous acid for healthy adult males. However, this information was based on the study of diets which contain no oxalate-rich foods other than tea which is the largest single source of the acid in typical English diets. If an average serving (60 g) of spinach or rhubarb had been included then the oxalate intake would have risen to between 400 and 600 mg/day but these levels are not typical for this country. Wide variations in oxalate intake may occur in countries such as India where vegetables rather than dairy products provide the main source of minerals and where many of the plants used as vegetables contain high concentrations of oxalate. Some indication of these variations has been provided by a study which found intakes ranging from 78–2045 mg/day depending on the season in the rural population of Udaipur, India. A relatively high intake was also found among upper-income groups in urban areas and was attributed to a high intake of tea and green, leafy vegetables, compared with lower-income groups.

As reported in "Oxalic Acid in Biology and Medicine", when taken with food, ingested oxalate is poorly absorbed from the gastrointestinal tract. Although oxalate absorption appears to be unaffected by metabolic inhibitors it is reduced by the presence of calcium which lowers the concentration of free oxalate ions. It is well known, for example that calcium oxalate is absorbed less readily than sodium oxalate and absorption is also reduced by the oral administration of cholestyramine (anion exchange resin which has a strong affinity for oxalate ions). Conversely, oxalate absorption is increased when the dietary intake of calcium is reduced and this is reflected in an increased urinary excretion of oxalate. In addition to a low calcium diet, the intake of disodium ethylenediamine tetraacetic acid (EDTA) appears to increase the absorption of oxalate by complexing of calcium with EDTA in the intestinal lumen leaving more oxalate free to be absorbed.

Also as reported in "Oxalic Acid in Biology and Medicine", the most important precursors of urinary oxalate in man are ascorbic acid, glycine, and dietary oxalate. Excretion of oxalate is also increased by the ingestion of a variety of substances including glycine, glutamic acid, purines, gelatin, and ascorbic acid. Conversely, excretion has been reported to be reduced by the administration of pyridoxine and magnesium oxide. Less than half of the normal dietary intake of oxalic acid can be accounted for by absorption into the body or excretion in the faeces. The remainder of the normal dietary intake of oxalic acid appears to be destroyed by a bacterial action in the large intestine. With a dietary intake of about 130 mg/day, more than 50 mg/day appears to be destroyed by bacterial action.

Also as reported in "Oxalic Acid in Biology and Medicine", large discrepancies have been reported in the "normal" concentration of oxalic acid in mammalian blood. Early studies obtain values ranging from 2–4 mg/100 ml of blood. Another study indicated that the normal blood concentration is probably less than 1 mg/100 ml of blood. Improved testing methods have given results in normal values within the range of 100 $\mu$g/100 ml to 800 $\mu$g/100 ml. More recent tests of human plasma have produced normal oxalic acid concentration ranging from 11.8–14.3 $\mu$g/100 ml of blood in man and 52.6 to 74.4 $\mu$g/100 ml of blood in sheep (see Table VI).

Feeding experiments and radioisotope studies have indicated that a considerable number of compounds are precursors of oxalic acid in animals and man, for example, glycine, glyoxylic acid, glycollic acid, ethyleneglycoll, ascorbic acid, and tryptophan (Oxalic Acid in Biology and Medicine). Studies with ascorbic acid have shown that the main excretory products of vitamin C in man are oxalate, ascorbic acid, and dehydroascorbic acid. From 17–40% of administered ascorbic acid was excreted as oxalic acid.

As reported in "Oxalic Acid in Biology and Medicine", a high oxalate intake reduces the intestinal absorption of calcium because of the formation of insoluble calcium oxalate and prolonged exposure to such a diet may lead to loss of bone mineral, particularly if the diet is also deficient in calcium or vitamin D. This situation is unlikely to occur very often in western countries where there is a plentiful supply of milk and other dairy products and oxalate-rich foods are relative uncommon. However, in developing countries such as India the situation is often quite different because tropical vegetables frequently with a high oxalate content provide the main source of minerals and the total oxalate intake may well exceed the calcium intake in certain seasons. Dietary oxalate is poorly absorbed on a normal diet containing adequate amounts of calcium.

Further, as reported in a literature including "Oxalic Acid in Biology and Medicine", poisoning from oxalic acid in animals and man has been recognized since the beginning of the 19th Century. The death rate from oxalate poisoning has declined supposedly because of a decreased use of oxalic acid in domestic cleaning fluids. Examples of chronic poisoning by absorption of oxalic acid through the skin and by inhalation have been reported. The range of lethal doses in acute poisoning is wide, varying between 2 and 30 g and depending upon a variety of factors such as the form in which the acid or its salt is taken and the amount of food, particularly calcium, which is present in the stomach and intestine. Death has occurred as early as 3 minutes and as late as 14 days after ingestion. Symptoms of acute oxalic acid toxicity in man can be divided into those caused by a local corrosive action and those resulting from absorption and excretion of the soluble oxalate. If a high concentration or the solid form is taken, the local effects may be predominant and death may result from acute hemorrhagic gastroenteritis without development of symptoms depending on absorption. If death does not result from local corrosive action then symptoms develop from the systemic effects and from renal insufficiency. The cardiovascular, neuromuscular and central nervous systems are markedly affected. The skin is pale, cold and clammy, the pulse is weak and the blood pressure and temperature are low. Numbness and tingling may develop in the extremities and cramp-like muscular and abdominal pain may be extremely severe. Local or generalized muscular twitchings occur and may progress to marked tetany and convulsive seizures. The central nervous system may show evidence of excitation or depression, varying from an acute maniacal state to stupor and coma. Death results from cardiovascular collapse or depression of the central nervous system. Renal involvement is frequent and even if the patient survives the severe local or systemic effects, death may ultimately occur from renal insufficiency, which dominates the picture from the second day. Oliguria develops and may progress to anuria.

Infection with oxalic acid producing fungi of aspergillus may result in massive deposition of calcium oxalate at the sight of infection and also renal oxalosis, leading to renal failure (Oxalic Acid in Biology and Medicine). Patients undergoing treatment with steroids, immunosuppressive drugs or cytotoxic agents are particularly liable to develop fungal infections and the increasing use of these drugs in malignancy and organ transplantation may be expected to lead to an increased incidence of aspergillosis infection.

Oxamide (ethanediamide, oxalamide, oxalic acid diamide, or ethanedioic acid diamide, or $C_2H_4N_2O_2$) is metabolized in the body to form oxalic acid.

In accordance with the present invention, therapeutically effective amounts of at least one therapeutically effective form of oxalate or oxalic acid including, oxalic acid dihydride, anhydrous oxalic acid, potassium oxalate, sodium oxalate, oxamide, plants or vegetables containing oxalic acid or the potassium salt thereof, or combinations thereof are administered periodically to prevent, control, or treat neoplasia, cancers, tumors, and the like. Further, these compounds are administered along with a therapeutically effective reduction in the administration or ingestion of oxalic acid or oxalate blockers such as calcium, potassium, vitamin C, vitamin B6, citric acid, alcohol, or combinations thereof.

Also, in accordance with the present invention, severe gastrointeritus, vomiting, diarrhea, melena, renal disease, renal damage, convulsions, coma, cardiovascular collapse, and the like caused by oxalic acid are treated by reducing oxalic acid or oxalate intake and/or administering therapeutic quantities of oxalic acid or oxalate blockers such as calcium, alcohol, potassium, citric acid, vitamin B6, vitamin C, and combinations thereof.

Oxalic acid dihydrate is commercially available in powdered, granular or crystal form for use as an industrial cleanser or solvent preparation.

In accordance with the present invention, oxalic acid may be present in a free acid, ester, lactone, or salt form. Also, oxalic acid, oxalate or related compound having the desired beneficial effect may be used as a composition, additive, supplement, and the like alone or in combination to prevent, control, or treat cancer, tumors, neoplasia, diseases and the like.

In accordance with the present invention, a therapeutic composition may be formed by adding oxalic acid dihydrate to food or drink to provide for the oral ingestion of a therapeutically effective quantity of oxalic acid.

A therapeutic composition of oxalic acid or oxalate compound of the present invention may be prepared by forming a food or drink including plants or vegetables high in oxalic acid or oxalate, for example carrots, chives, parsley, beets, spinach, or combinations thereof (see Tables I–IV).

A therapeutic composition of the present invention in the form of a daily supplement, pill, gelcap, pharmaceutical, or the like is prepared by placing a therapeutically effective amount of oxalic acid or oxalate compound in pill form for oral ingestion as directed.

A therapeutic composition of the present invention in cream or ointment form for topical administration of oxalic acid is prepared by mixing a dilute concentration of oxalic acid in a solvent such as distilled water, ethanol, acetone, propylene glycol or polysorbate to form a solution which is then mixed in a conventional manner with a commonly available cream or ointment base such as hydrophilic ointment or petrolatum. Therapeutic compositions of the instant invention may also be formulated in gel, lotion, spray, stick or powder form.

It is believed that the therapeutic effect of the oxalic acid or oxalate in treating tumors, cancers, neoplasia, and other disorders affecting humans involves the administration whether it be oral, by injection, suppository or the like of a therapeutic and beneficial quantity of oxalic acid in one of its free acid, salt, or other forms to elevate the blood oxalic acid level to between 350 $\mu$g/100 mL and 450 $\mu$g/100 mL, preferably 425 $\mu$g/100 mL and/or the urine oxalate level to between 40 mg/L and 80 mg/L, preferably 60 mg/L for a 70K human.

Also in accordance with the present invention in the treatment of canines, an oxalic acid or oxalate level chart for canines and felines differs from that for humans in that the desired therapeutic effect can be produced from 14 mg/L to 50 mg/L, preferably 22 mg/L oxalate level in the urine of a 25 K animal as compared with 40 mg/L to 80 mg/L, preferably 60 mg/L in the human urine. Likewise, the normal blood oxalic acid level of an animal such as canine or feline differs from that of humans.

Along this line, it has been determined that about 1 gram per day intake of oxalic acid provides about a 22 mg/L level of oxalate in the urine of a 25 Kilogram (K) canine.

In accordance with one embodiment of the present invention a multiple vitamin formula having oil and water soluble vitamins with minerals in tablet form with a suggested use to take one tablet daily with a full glass of distilled water preferably within an hour of a meal or as directed by a physician, includes about 100 mg oxalic acid together with 5,000 IU vitamin A, 60 mg vitamin C, 400 IU vitamin D, 30 IU vitamin E, 25 mcg vitamin K, 1.5 mg thiamin (vitamin B1), 1.7 mg riboflavin (vitamin B2), 20 mg niacin, 2 mg vitamin B6, 400 mcg folate, 6 mcg vitamin B12, 30 mcg biotin, 10 mg pantothenic acid, 162 mg calcium, 18 mg iron, 109 mg phosphorus, 150 mcg iodine, 100 mg magnesium, 15 mg zinc, 20 mcg selenium, 2 mg copper, 2.5 mg manganese, 25 mcg chromium, 25 mcg molybdenum, 36.3 mg chloride, 40 mg potassium, 5 mcg nickel, 10 mcg tin, 2 mg silicon, 10 mcg vanadium, and 150 mcg boron. Such a multiple vitamin formula with added minerals provides a 100% daily value of at least vitamin A, vitamin C, vitamin D, vitamin E, vitamin B1, vitamin B2, niacin, vitamin B6, pholate, vitamin B12, pantothenic acid, iron, iodine, zinc, and copper. A daily value has not been established for oxalic acid. Each tablet would contain the following ingredients: oxalic acid or oxalate, oxalic acid dihydrate, anhydrous oxalic acid, or other form of oxalic acid or oxalate, or combinations thereof together with dicalcium phosphate, magnesium oxide, potassium chloride, ascorbic acid, ferrous fumarate, calcium carbonate, gelatin, starch, cellulose, dl-alpha, tocopheryl acetate, hydroxypropyl methylcellulose, croscarmellose sodium, sodium starch glycolate, niacinamide, zinc oxide, silicon dioxide, D-calcium pantothenate, sodium metasilicates and oxides, titanium dioxide, hydroxypropyl cellulose, polyethylene glycol 3350, manganese sulfate, magnesium stearate, pharmaceutical glaze, polysorbate 80, pyridoxin hydrochloride, copper oxide, povidone, sodium and potassium borates, riboflavin, vitamin A, acetate, thiamin mononitrate, beta carotene, resin, folic acid, potassium iodide, chromium chloride, ergocalciferol, sodium molybdate, sodium selenate, yellow 6 lake, sodium metavanadate, stannous chloride, nickelous sulfate, phytonadione, biotin (U.S.P. method 2), and cyanocobalamin (U.S.P. method 2). This product would be formulated per official U.S.P. standards to meet disintegration or dissolution, weight, purity, and potency requirements.

An alternative embodiment of the present invention would include a multiple vitamin and mineral tablet or daily supplement including oxalic acid in one of its forms or oxalate together with all the above mentioned vitamins and minerals except those which serve as oxalic acid or oxalate blockers. For example, the inclusion of oxalic acid or oxalate blockers would be eliminated or greatly reduced so as to prevent blocking the beneficial effect of the oxalic acid or oxalate. Such blockers include calcium, potassium, vitamin B6, vitamin C, citric acid, alcohol, magnesium, etc.

In accordance with at least one embodiment of the present invention, oxalic acid or oxalate is used for the treatment of viral, bacterial, or chemical diseases of warm blooded animals including humans, dogs, and the like.

In accordance with a particular embodiment of the present invention, oxalic acid or oxalate is used in a method of therapeutically treating a human including administering a therapeutically effective dosage of oxalic acid, oxalic acid salt, oxalic acid ester, or other therapeutically effective form thereof, in an amount and for a period of time sufficient to provide the desired effect.

The method as described above wherein the oxalic acid is in the form of a free acid.

The method as described above wherein the acid is in salt form.

The method described above wherein the oxalic acid, oxalate or other therapeutically effective form thereof is administered periodically for a period of time sufficient to achieve at least a clinically discernible effect, for example, a reduction in the size of a tumor.

The method as described above wherein the oxalic acid, oxalate or other therapeutically effective form thereof is administered periodically for a period of time sufficient to achieve at least a substantial therapeutic effect, for example the eradication of a tumor.

The method as described above wherein the oxalic acid or oxalate is administered daily.

The method as described above wherein the period of time is at least one month.

The method as described above wherein after one month the oxalic acid is administered on a weekly basis.

The method as described above wherein the oxalic acid, oxalate or other therapeutically effective form thereof is present in a therapeutically acceptable composition including a carrier.

The method as described above wherein the composition is a powder, tablet, gelcap, lotion, cream, gel, ointment, solution, mixture, food, nutritional supplement, formulation, transdermal patch, drops, or combination thereof.

In accordance with one embodiment of the present invention, a therapeutically effective dosage of oxalic acid or oxalate is administered on a periodic basis by the ingestion of one or more foods including oxalic acid in one of its therapeutically effective forms including free acid, salt, ester, lactone, anhydride, dihydrate, diamide, or the like.

In accordance with a particular example, a four pound sourdough bread loaf is made from conventional bread ingredients including flour, water, yeast, and sourdough and has added thereto two rounded tablespoons of dried, chopped parsley which is mixed with the other ingredients to be disbursed throughout the loaf. These two rounded tablespoons of dried parsley provide approximately 2 grams of oxalic acid or oxalate in the loaf of bread. Hence, half of the loaf contains about 1 gram, ¼ of the loaf contains about ½ gram, ⅛ of the loaf contains ¼ of a gram, and 1/16 of the loaf contains about ⅛ of a gram of oxalic acid.

In accordance with one embodiment of the present invention, the above described loaf of oxalic acid or oxalate containing sourdough bread is used in a method of therapeutically treating a warm blooded animal by having the animal periodically ingest a portion of the loaf. For example, in the treatment of an adult male human, he could ingest daily up to about ½ of a loaf of this bread to achieve a dosage of oxalic acid of up to about 1 gram oxalic acid per day. This dosage may be reduced after a period of time and given a certain health condition to ½ gram or less oxalic acid per day, and, as such, ¼ loaf or less of the bread per day.

The above described oxalic acid or oxalate containing sourdough bread does not include any salt, sugar or preservatives since the oxalic acid serves as a preservative.

In using oxalic acid or oxalate as a therapeutic agent, one must be careful to administer the proper dosage given certain health conditions or in order just to maintain a healthy condition since an overdose of oxalic acid or oxalate can cause severe problems such as renal failure, heart failure, diarrhea, vomiting, convulsions, melena, and the like. It is believed that a proper balance should be maintained between oxalic acid, oxalate and their blocking agents such as potassium, barium, calcium, copper, magnesium, silver, strontium, alcohol, citric acid, vitamin B6, vitamin C, and the like. If a high dosage of oxalic acid or oxalate would reduce calcium levels, potassium levels, magnesium levels, and the like necessary for proper heart functioning, it is necessary to limit the administration of oxalic acid or oxalate to the minimum dosage necessary to provide the desired therapeutic effect without causing undesired side effects or health problems.

In accordance with the present invention, the dosage of oxalic acid or oxalate is monitored and altered as necessary by monitoring the oxalic acid or oxalate levels in the urine and/or blood in the patient, whether that patient be a human, canine, or the like. Also in accordance with the present invention, the amount of blockers such as calcium, vitamin 26, vitamin C, citric acid, alcohol, or combinations thereof are monitored in the urine and/or blood of the patient.

It has been discovered that the body of an animal such as human or canine is a complex chemical factory which requires a particular balance of compounds, chemicals, vitamins, minerals, nutrients, and the like to provide for and maintain optimum health of the animal. It is believed that too little oxalic acid or oxalate in the animal may allow for the advent of neoplasia, tumors, cancers, growths, and the like while too much oxalic acid or oxalate may cause back pain (due to kidney trouble), heartburn, indigestion, heart trouble, nerve trouble, and the like. Thus, it is recommended that each individual case be studied and that the proper dosage of a therapeutically effective amount of oxalic acid, oxalate, enhancers, and/or blockers be administered on a periodic basis at one level to maintain proper health by preventing neoplasia, tumors, growths, and the like, at a different level to treat, combat, control, or eradicate tumors, growths, cancers, neoplasia, or to cleanse the blood, and at a third intermediate level once the blood is clean and relatively free of cancer, tumor or neoplasia cells, to combat, reduce the size of, or treat an existing tumor, cancer, growth, or the like. Since each person or animal is different, and their body chemistries operate in at least some small fashion differently than other persons or animals, the administration of a therapeutically effective dosage of oxalic acid, oxalate, enhancers, and/or blocking agents should be reevaluated and monitored on a regular basis by, for example, physical examination, x-ray, CAT scan, MRI imaging, sonogram, biopsy, blood analysis, urine analysis, fecal analysis, as well as other conventional diagnostic techniques.

It is believed that a proper balanced diet including foods containing oxalic acid in one of its forms including oxalate which may be metabolized by a human or other warm blooded animal can serve to maintain proper health, extend life, increase the quality of life, increase energy, increase cranial activity, prevent neoplasia, tumors, cancers, etc., help to combat viruses, bacteria, improve the immune system, and provide other beneficial short term and long term health effects.

Some forms of oxalic acid or oxalate which may prove beneficial to humans and other warm blooded animals, include ethanedioic acid (free acid), ethanedioic acid anhydride, ethanedioic acid tripotassium salt, ethanedioic acid barium salt, ethanedioic acid copper salt, ethanedioic acid diamide, ethanedioic acid diamonium salt, ethanedioic acid diethyl ester, ethanedioic acid dimethyl ester, ethanedioic acid disodium salt, ethanedioic acid magnesium salt, ethanedioic acid silver salt, ethanedioic acid strontium salt, ethaneaioic acid dihydrate, dicarboxylic acid, as well as other forms of oxalic acid or oxalate which may be metabolized by the body, injected into the circulatory system, administered by transdermal patch, administered by suppository, or administered by topical application, and the like, to provide the desired therapeutic effect. Although one or more of the above may be considered poisons to humans or other warm blooded animals, the proper administration of a selected dosage is believed to be therapeutically effective and instrumental in the treatment, prevention, control, and maintenance of health. It is not uncommon for an agent which is a poison to provide a beneficial effect. Aspirin is one of the myriad of hundreds or thousands of poisons which provide a beneficial effect to warm blooded animals when administered in a proper dosage.

It is believed that oxalic acid or oxalate may be one of the primary causes of the onset of osteoporosis. Too much oxalic acid or oxalate in the diet may reduce the calcium in the body to a point of causing or aggravating osteoporosis. Hence, the treatment and prevention of osteoporosis is the control of the oxalic acid, oxalate and calcium levels. Women in a high risk group for osteoporosis should be careful to increase calcium intake and decrease oxalic acid or oxalate intake to prevent, treat, or control osteoporosis.

It is believed that oxalic acid or oxalate may be a blood purifying agent which in addition to controlling, treating, or eradicating abnormal cells, oxalic acid in the blood may control cholesterol and plaque or fat buildup. Thus, the periodic or daily administration of a certain quantity of oxalic acid in one of its therapeutically effective forms including oxalate may serve to not only purify the blood, but also control, treat, or effect cholesterol, plaque, and fat buildup in the cardiovascular system or in the brain, and in so doing improve and maintain good cardiovascular health and operation.

It is believed that oxalic acid or oxalate may also be an effective treatment for parve. Also, oxalic acid or oxalate may be used as a hemostatic and antiseptic agent in animals.

It is believed that oxalic acid or oxalate should be administered following exposure to X-ray radiation, X-rays, mammograms, radiation therapy, CAT-scans, nuclear or atomic exposure, radiation therapy, chemotherapy, radioactive pellet treatment, and the like, to prevent the formation of tumors, cancers, neoplasia by counteracting the destruction of oxalic acid or oxalate caused by the exposure or treatment.

It is believed that a dosage of oxalic acid or oxalate may also provide a reserve of energy or nutrients. Hence, a food or beverage containing oxalic acid or oxalate could be ingested prior to strenuous activity in order to increase energy, stamina, strength and/or mental activity.

It is also believed that oxalic acid or oxalate may prevent or relieve muscle soreness by helping eliminate lactic acid.

It is also believed that oxalic acid or oxalate should be administered after exposure to specific oxalic acid or oxalate decomposing bacteria to prevent the onset of tumors. For example, workers at poultry houses may take oxalic acid or oxalate to maintain a normal level of oxalic acid or oxalate to prevent tumor development and counteract exposure to bacteria.

In addition to the administration or ingestion of oxalic acid or oxalate, it is believed that one should limit the intake of dairy products since these tend to counteract the beneficial effect of the oxalic acid or oxalate.

It is believed that oxalic acid or oxalate should be administered prior to a transplant operation to purify the blood and improve the immune system. However, it is also possible that just prior to a transplant operation the body should be purged of oxalic acid to prevent aspergillus fungi infection.

It is believed that strong magnetic fields, MRI imaging, computer terminals, power lines, cellular telephones, electronic equipment, microwave ovens, etc. may decompose oxalic acid or oxalate in the body and blood and allow the formation of tumors, growths, cancers, etc. Hence, those subjected to strong magnet fields and the like should increase their oxalic acid or oxalate intake to counteract such decomposition.

It is also believed that the administration of oxalic acid or oxalate may delay, prevent, control, or treat the onset of Alzheimer's Disease, lessen the effects of the disease, or improve the quality of life of a person suffering from Alzheimer's Disease.

It is also believed that oxalic acid or oxalate may be a control, treatment, or preventative, for autoimmune related diseases such as AIDS, HIV, SLE, BSE, CFS and the like by preventing, lessening, or controlling the destruction of the bodies immune system. Hence, the administration, ingestion, injection, etc. of oxalic acid in one of its therapeutically effective forms including oxalate may serve to treat, prevent, or control the debilitating effects of autoimmune related diseases, viral diseases, bacterial infections, and the like.

One publication mentioned that human blood typically has a mean value of about 288 $\mu$g of anhydrous oxalic acid per 100 ml of blood. If a subject's blood is tested and their oxalic acid level is below this mean value, it is believed that they should be administered oxalic acid in one of its forms including oxalate, easily metabolized by the body to increase their blood oxalic acid level. Also it is believed that if someone is suffering from cancer, tumors, AIDS, bacterial infection, etc. that they should be administered oxalic acid or oxalate in order to increase their blood oxalic acid level to a higher value than the typical mean value.

In accordance with one embodiment of the present invention, a new scale is developed for canine and feline urine oxalate level. Since a typical human scale will not work for a canine or feline due to their different body structures and metabolism, a need exists for a canine and/or feline scale which will provide a quick-ready reference for a veterinarian or pet owner to test urine oxalate levels and adjust the oxalic acid intake in the diet accordingly.

Oxalic acid is a reducing agent, bacteriostatic agent, and may be an antioxidant.

In accordance with the present invention, it is believed that five or more items unnaturally constantly consumed are responsible for tumors or cancers and the like. These items, calcium, vitamin B6, vitamin C, citric acid, and alcohol are believed to be oxalic acid or oxalate blockers. It is interesting to note that a variety of prepared foods eaten every day including cookies, cakes, canned foods, salad dressings, and the like contain these items. Further, it is interesting to note that certain articles have proposed that persons on a low-fat diet showed less tumors or showed tumor reduction. Since red meat such as beef or liver contains vitamin B6 (pyridoxine hydrochloride) it follows that reduction or elimination from the diet also serves as a reduction or elimination of a blocker of oxalic acid or oxalate. Tables VII–XI list the pyridoxine hydrochloride content of meats and other foods.

Although others have indicated that vegetables are cancer fighters, they have listed the cancer fighting agents as antioxidants, beta carotene, or citric acid. The literature is void of a reference to oxalic acid as being a cancer fighter or preventer.

The literature suggests that tumors occur when the immune system fails to eliminate abnormal cells not consumed as a normal biological function of the body systems. In accordance with the present invention, it is believed that a low intake of oxalic acid or oxalate or a high intake of oxalic acid or oxalate blockers including alcohol, citric acid, ascorbic acid, and pyridoxine hydrochloride weakens the immune system or the body's natural cancer fighting ability to the point where the body cannot control abnormal cell growth, tumors, cancer, and the like. Changing the diet to include an increase in the intake of oxalic acid or oxalate and eliminating or drastically reducing the intake of oxalic acid or oxalate blockers, allows the body's immune system or natural cancer fighting systems to function and eliminate abnormal cells.

It is believed that carrots, spinach, parsley, chives, beet leaves, garlic, collards, radishes, and the like are relatively high in oxalic acid or oxalate and should be eaten in order to build a high concentration of oxalic acid or oxalate in the body. It is believed that if one can maintain a balanced diet and assure an adequate level of oxalic acid or oxalate in the system then the body's natural protection mechanisms, immune system, and the like can prevent, treat, and control tumors, growths, cancers, viral or bacterial diseases, chemical toxins, and the like.

Over the years, many claims have been made regarding the beneficial health effects of many fruits, vegetables, plants, molds, etc. For example, garlic is believed to fight infection, cancer, bacteria, virus, and heart disease. Strawberries are also believed to help prevent prostate cancer. Tomatoes or spaghetti sauce are believed to prevent cancer and heart attacks. A recent study indicated that two cups of coffee a day can prevent suicide in women who work.

On the other hand, plants, vegetables and chemicals which contain high levels of oxalic acid or oxalate are according to conventional wisdom thought to be poisons and to be eliminated from the diet or use. For example, those suffering from kidney stones are told to stay away from rhubarb leaves, spinach, Swiss chard, lambsquarter, and beet leaves which contain high amounts of oxalates. Also, they are told to stay away from black and green teas and coffee which also contain oxalic acid. Further, nuts, chocolate and strawberries are cited by some as containing high-oxalate.

Opposite conventional thinking, in accordance with the present invention, it is believed that oxalic acid or oxalate is the "silver bullet", "hall monitor", or "brevet boule" that treats, kills, controls, manages, or prevents abnormal, tumor, cancer or unspecialized cells and, thereby, treats diseases and maintains good health. Further, it has been discovered that a high oxalic acid or oxalate intake causes a cancer patient to be more talkative, verbal, have increased dexterity, physical ability, mental ability, and appear invigorated, happier and more outgoing.

The conventional treatments for cancer, tumors, growths and the like can themselves cause cancer, tumors, growths and the like. For example, X-rays can trigger malignant growths in certain people. Further, in accordance with the present invention, decomposition or reduction of oxalic acid or oxalate in the body caused by exposure or treatment of X-rays, CAT-scans, strong electromagnetic waves or fields, electron bombardment, microwaves, and the like reduce the level of oxalic acid or oxalate in the body and further increase the chance of growths, tumors, cancers, and disease. Hence, it is believed that one should not only increase the intake of oxalic acid or oxalate, but also avoids exposure to or treatment of radiation, X-rays, electromagnetic fields and the like which tend to decompose or reduce the amount of oxalic acid or oxalate in the body.

Along this same line, it is believed that conventional testing techniques, such as the testing of carcinogens on mice may provide faulty results in that the first step typically in such testing is to irradiate the mice with radiation to weaken their immune system so that they are more susceptible to carcinogens. The radiation to weaken the immune system also causes a reduction or elimination of the oxalic acid or oxalate in the mice. In accordance with the present invention, it is believed that a normal level of oxalic acid or oxalate is required in the body to prevent cancers, growths, tumors, and the like. Hence, the researchers unknowingly introduced an additional cancer causing factor into the testing.

In accordance with the present invention, an improved testing method would involve determining the normal oxalic acid or oxalate level of the test animal, weakening the immune system of the animal using radiation, and then administering or feeding to the animal a sufficient quantity of oxalic acid or oxalate to bring their oxalic acid or oxalate levels back up to normal prior to further testing.

Also, in accordance with the present invention, it is believed that testing, research, and examinations which include X-rays or electronic scans to insure no cancer is present or to check on the size or location of the cancer can themselves bring on cancer by decomposing oxalic acid or oxalate and irritating the skin or tissue. Further, if test animals are fed a diet high in oxalic acid or oxalate blockers such as calcium, vitamin B6, vitamin C, citric acid, and the like the effective level of oxalic acid or oxalate in the animal is reduced and the test results may be skewed and possibly not representative of the natural normal animal biochemistry or system. Hence, it is believed that improved human examination and animal testing involves a reduction in the use of X-ray or electronic scans, in the incorporation of a balanced diet containing oxalic acid or oxalate and a reduction in oxalic acid or oxalate blockers.

In accordance with another embodiment of the present invention, an improved method of testing for cancer includes the elimination of the use of X-rays or electronic scans during the testing process.

In accordance with another embodiment of the present invention, an improved method of testing for cancer allows for the use of X-rays or electronic scans to detect the presence or absence of cancer, but requires that the oxalic acid or oxalate decomposed or reduced by the X-ray or electronic scan be replaced.

In accordance with another embodiment of the present invention, an improved method of testing for cancer employs the use of an improved animal feed which includes at least one form of oxalic acid or oxalate and with a reduced amount of oxalic acid or oxalate blockers from that of conventional feed.

If one is to administer and ingest oxalic acid in one of its harsher forms such as oxalic acid dihydrate, for example, a gel cap filled with 500 milligrams to 2 grams of oxalic acid dihydrate, this should be taken one hour before or after a meal and with a sufficient quantity of water such as 10 or more ounces of distilled water. In order to further reduce the possibility of harm or irritation to the digestive system, one can line the stomach before taking such an oxalic acid pill or gel cap using Pepto Bismol, Tagamet, or Zyntec.

In accordance with another aspect of the present invention, workers exposed to X-rays, CAT-scans, electromagnetic fields or waves, microwaves, radar, high voltage power lines, electronic equipment and the like are given sufficient quantities of foods, beverages, supplements, treats or the like containing at least one beneficial form of oxalic acid or oxalate to compensate for the decomposition or reduction caused by their working environment and thereby prevent the development of tumors, cancers, diseases, poor health, etc. which may otherwise be caused by their work environment.

In recent history, there has been an increase in breast cancer in women in the United States. In accordance with the present invention, it is believed that this increase in breast cancer may be due in part to the use of microwave ovens which emit microwaves, which when used in cooking or heating decompose the oxalic acid or oxalate in the food or beverage, use of a myriad of electronic equipment including radios, televisions, computers, etc. and the consumption of processed foods which contain oxalic acid or oxalate blockers such as calcium, citric acid, vitamin C, vitamin B6 and the like.

In accordance with another embodiment of the present invention, a person who believes they have been subjected to radiation, strong electromagnetic waves or fields, microwaves, radar, strong tv or radio waves, or work in a dangerous environment where they may be subjected to X-rays or other elements which can decompose or reduce the oxalic acid or oxalate in the body, can test their blood, plasma or urine oxalic acid or oxalate level and if they find it is below normal, treat themselves with food, beverages, supplements, pills, capsules, and the like containing oxalic acid or oxalate to bring their level back up to a normal healthy level. Further, such a person can pre-treat themselves prior to exposure with oxalic acid or oxalate to reduce the chance that their levels will drop below normal levels. This should prevent or reduce the increased risk to developing cancers, tumors, viral or bacterial diseases and the like caused by having below normal oxalic acid or oxalate levels in the body.

As shown in FIG. 1 of the drawings, solutions of oxalic acid are decomposed by radiation. This has been the basis of a method for measuring radiation dosage in the sterilization of food and medical products. The absorbed dose is determined from the decrease in oxalic acid concentration which occurs during irradiation.

In addition to the information provided in Table IV, nuts contain high concentrations of calcium, magnesium, iron and relatively high concentrations of oxalate. For example, almond, cashew, peanut, pecan and walnut all contain oxalic acid concentrations ranging from 200 mg/100 g–600 mg/100 g. Forage grasses and other pasture plants frequently contain high concentrations of minerals but many of them also contain high concentrations of oxalate. Further, many beverages including beers, wines, and fruit drinks contain low concentrations of oxalate but tea, coffee, cocoa, and chocolate contain relatively high concentrations of oxalate. Tea, in fact, is listed as being the largest single source of oxalate in English diets.

According to Occupational Health Services, Inc. (OHS), oxalic acid has a CAS number: 144-62-7A a RTECS number: R0245000, trade names or synonyms ethanadoic acid, aktisal, aquisal, dicarboxylic acid, phosphotex 760 grain refiner, $C_2H_2O_4$, and OHS17360. Oxalic acid is in the chemical family carboxylic acid, aliphatic and is listed as a poison with a level three out of a scale 0–3 for health, and a level 1 fire rating.

In accordance with the present invention it is believed that conventional wisdom that the cause of acorn poisoning is tannic acid is wrong and that it is instead the oxalic acid which is extremely damaging to renal tissues. It is believed that the oxalic acid or oxalate level in oak trees is very high, especially in mold that grows on the bark.

Also, it is believed that the treatment for oxalic acid or oak poisoning is to increase oxalic acid or oxalate blockers, such as pyridoxine hydrochloride, citric acid, calcium, magnesium, and alcohol such as ethanol to eliminate or carry the oxalic acid through the renal system.

Oxalate nephrosis is probably the most common cause of toxic death in dogs. Typically, the source of oxalate poisoning is ethylene glycol (antifreeze). The ethylene glycol is metabolized to oxalate and oxalic acid by an enzyme called alcohol dehydrogenase. Ethylene glycol by itself is not toxic, but when the enzyme, alcohol dehydrogenase, works on it to produce a toxic material (oxalate), then it becomes toxic. Antifreeze poisoning is treated with alcohol (ethanol) to keep the alcohol dehydrogenase enzyme busy so that the antifreeze can be eliminated, unaltered, and in a non-toxic state. A major contributor to death is also metabolic acidosis caused by oxalic acid accumulation. It is almost as important to control the acid-based status as it is worrying about the accumulation of oxalate.

There are several other causes of oxalate nephrosis which are extremely rare. Overdoses of vitamin C have been shown to cause oxalate nephrosis in humans, and in at least one goat. Vitamin B6 (pyridoxine hydrochloride) deficiency and methoxyflurane anesthesia may also induce the condition. Aspergillus sp. fungi also produces high levels of oxalate and these fungi are almost ubiquitous and grow on many feed stuffs. There are a variety of plants other than oak, for example halogenten, greasewood, sorrel, dock, setaria grass, sugar beets, and several others that contain oxalic acid.

Oxalate nephrosis produces a very specific lesion in the kidney when viewed under the microscope. You can actually see the oxalate crystals. A pathologist who is unaware of primary hyperoxaluria would obviously draw the conclusion that the kidney lesions were the result of oxalate nephrosis.

Typically, cancer, tumors, growths, and the like are treated by invasive unnatural techniques, such as surgery, biopsy, x-ray radiation, chemotherapy, and the like. In accordance with the present invention, it is believed that the primary treatment for cancer should be the all natural, non-invasive, use, administration, and the like of oxalic acid in one of its therapeutically effective forms including oxalate in a sufficient quantity and on a periodic basis to provide the desired therapeutic effect.

Essiac tea was tested and found to have a pH of about 4.79 when the powder was added to boiling distilled water.

The following are illustrative examples of methods, formulations and compositions according to the present invention. Although the examples utilize only selected compounds and formulations, it should be understood that the following examples are illustrative and not limiting. Therefore, any of the aforementioned oxalic acids, oxalates, or related compounds may be substituted according to the teachings of the present invention in the following examples.

EXAMPLE 1

A therapeutic composition for the treatment of tumors is made up of freeze-dried parsley with a rounded tablespoon of freeze-dried parsley providing about 1 gram of oxalic acid.

EXAMPLE 2

A sufficient quantity of dried parsley is administered daily to provide the desired therapeutic effect and produce or maintain a desired blood oxalic acid or oxalate level for preventing, controlling, or treating tumors.

EXAMPLE 3

A relatively large adult male human having an inoperable brain tumor is administered 4 tablespoonfuls of dried parsley daily, providing approximately 4 grams of oxalic acid per day, until the growth of the tumor is checked. Thereafter, he is administered 1 tablespoonful of dried parsley daily, or approximately 1 gram of oxalic acid per day.

In addition to the administration of the dried parsley, his intake of oxalic acid blockers including calcium, pyridoxines, citric acid, ascorbic acid, alcohol, or combinations thereof is reduced.

EXAMPLE 4

A therapeutic composition for treating tumors, cancer, neoplasia, and the like, is made up of carrot juice which is administered orally in 2 ounce servings to provide between 4 and 6 ounces of carrot juice daily to provide the desired therapeutic effect and desired oxalic acid or oxalate blood or urine level.

EXAMPLE 5

Carrot juice containing oxalic acid or oxalate is administered orally and mixed with other juices and flavoring agents such as tomato juice, salt, pepper, parsley, and/or celery to enhance the flavor thereof.

EXAMPLE 6

A therapeutic composition in the form of a nutritional supplement or multi-vitamin, multi-mineral tablet containing a small quantity of oxalic acid, preferably 500 milligrams or less of oxalic acid, together with conventional ingredients such as vitamins and minerals.

EXAMPLE 7

A treatment regimen or method including the oral administration of one such tablet, pill, multi-vitamin, or supplement of Example 6 daily.

EXAMPLE 8

The therapeutic composition of Example 6 including 1 gram or less, preferably 500 milligrams or less oxalic acid, together with conventional quantities of other vitamins and minerals except that one or more of the oxalic acid blockers, including vitamin C, vitamin B6, calcium, citric acid, and the like, are reduced or eliminated altogether from the pill, vitamin, multi-mineral, supplement, etc.

EXAMPLE 9

Another therapeutic composition contains oxalic acid together with conventional pet foods.

EXAMPLE 10

A conventional pet food mixture is mixed with oxalic acid in sufficient quantity to provide the desired therapeutic effect. For example, 1 gram or less, preferably 500 milligrams or less of oxalic acid dihydrate is mixed with a single serving quantity or portion of dog food or cat food to provide a daily dosage of one gram or less, preferably 500 milligrams or less of oxalic acid (see Table XII).

EXAMPLE 11

The therapeutic composition of the above example except that one or more ingredients in pet food which are oxalic acid blockers are eliminated or reduced in quantity from that of conventional pet food. For example, the quantity of vitamin B6, vitamin C, calcium, citric acid, or combinations thereof are reduced or eliminated from conventional pet food in addition to the admixture of oxalic acid dihydrate.

EXAMPLE 12

A therapeutic composition in the form of a pet food that includes a conventional pet food mixed with a source of oxalic acid or oxalate such as carrots, parsley, chives, or combinations thereof to provide a pet food having an oxalic acid content of 1 gram or less, preferably 500 milligrams or less of oxalic acid per daily serving of pet food.

EXAMPLE 13

A therapeutic composition containing oxalic acid as a topical skin treatment includes a mixture of 5 grams or less of oxalic acid, 40 milliliters distilled water, and 12 milliliters propylene glycol.

EXAMPLE 14

The topical skin treatment composition of Example 13 serves as an exfoliant, acne treatment, skin cancer treatment, growth treatment, or combinations thereof.

EXAMPLE 15

A therapeutic composition for the treatment of tumors, cancer, growths, neoplasia, and the like is made up of dried chives.

EXAMPLE 16

A sufficient quantity of dried chives is administered on a periodic basis to provide the desired therapeutic effect.

EXAMPLE 17

A therapeutic composition for the maintenance of good health, prevention, treatment, or control of tumors, growths, or cancer, and the like is made up of a food item such as bread, cereal, or other prepared food including oxalic acid or plant or vegetable containing oxalic acid like parsley or chives, in a quantity to provide the desired therapeutic effect.

EXAMPLE 18

A composition for improving and maintaining good health in warm-blooded animals including humans and pets and having a composition selected from oxalic acid, oxalate, oxalic acid dihydrate, a nutritional supplement containing oxalic acid, a nutritional supplement containing oxalate, a nutritional supplement containing oxalic acid dihydrate, or combinations thereof.

EXAMPLE 19

A flavor-enhancer including at least one form of oxalic acid.

EXAMPLE 20

A preservative including at least one form of oxalic acid.

EXAMPLE 21

In a prepared food product, the improvement including at least one form of oxalic acid.

EXAMPLE 22

In a prepared food product, the improvement including the elimination of citric acid and the addition of at least one form of oxalic acid.

EXAMPLE 23

A method of enhancing or promoting the growth or the spread of tumors, growths, neoplasia and the like in warm-blooded animals such as test animals including the steps of reducing the intake of oxalic acid or oxalate in the diet, destroying the oxalic acid or oxalate in the animal, and/or increasing the intake of oxalic acid or oxalate blockers.

EXAMPLE 24

In a diet for promoting good health in warm-blooded animals including humans, the improvement including increasing the quantity of oxalic acid or oxalate-containing foods, and reducing the intake of oxalic acid or oxalate blockers.

EXAMPLE 25

A method of inhibiting the therapeutic effect of oxalic acid or oxalate in warm-blooded animals such as test animals including the steps of increasing the ingestion of oxalic acid blockers such as calcium, alcohol, red meat, citric acid, vitamin B6, vitamin C, potassium, dairy products, and the like, administering oxalic acid blockers, such as calcium, alcohol, citric acid, vitamin C, vitamin B6, and the like, and/or destroying or decomposing some or all of the oxalic acid or oxalate in the animal.

EXAMPLE 26

A method for inhibiting, preventing, treating, or controlling the deleterious effects of diarrhea, indigestion, damage to digestive tract, kidney damage, or renal failure caused by high levels of oxalic acid including the steps of at least one of reducing the ingestion or administration of oxalic acid, oxalate, oxalic acid dihydrate, a nutritional supplement containing oxalic acid, a nutritional supplement containing oxalate, a nutritional supplement containing oxalic acid dihydrate, foods containing oxalic acid, foods containing oxalate, foods containing oxalic acid dihydrate and combinations thereof, increasing the ingestion or administration of oxalic acid or oxalate blockers, monitoring the levels of oxalic acid or oxalate in the blood or urine, adjusting the ingestion or administration of oxalic acid or oxalate-containing compounds and the ingestion or administration of oxalic acid or oxalate blockers to achieve the desired oxalic acid or oxalate levels.

EXAMPLE 27

A method of counteracting, inhibiting, treating, controlling, or reducing the deleterious effects of high levels of oxalic acid including the steps of administering or ingesting a therapeutically effective amount of vitamin B6, vitamin B6-containing nutritional supplements, foods containing vitamin B6, or combinations thereof.

EXAMPLE 28

A method of treating a warm-blooded animal including the steps of determining the oxalic acid blood level or oxalate urine level of the animal, comparing this level with a scale indicating below normal, normal, and above normal oxalic acid or oxalate levels, increasing the administration or ingestion of oxalic acid or oxalate if the level is below normal, reducing the ingestion or administration of oxalic acid or oxalate blockers if the level is below normal, maintaining current ingestion or administration of oxalic acid or oxalate if the oxalic acid or the oxalate level is normal, reducing the ingestion or administration of oxalic acid or oxalate if the level is above normal, or increasing the ingestion or administration of oxalic acid or oxalate blockers if the level is above normal.

EXAMPLE 29

The method as described in Example 28 wherein the oxalic acid or oxalate level scale has differing below normal, normal, and above normal level categories for different health conditions.

EXAMPLE 30

In a multivitamin and mineral supplement, the improvement including the addition of at least one therapeutically effective form of oxalic acid.

EXAMPLE 31

The multivitamin and mineral supplement as described in Example 30 further including the improvement of the reduction or elimination of oxalic acid or oxalate blockers therein.

EXAMPLE 32

An oxalic acid treatment method including the step of mixing carrot juice with other juices and flavoring agents such as tomato juice, salt, pepper, parsley, celery, and the like to enhance the flavor thereof.

EXAMPLE 33

A therapeutic composition for the maintenance of good health and the prevention, treatment, or control of tumors, growths, cancer, neoplasia and the like of a food or beverage including a therapeutically effective amount of at least one therapeutically effective form of oxalic acid such as a plant or vegetable containing oxalic acid or oxalate like parsley or chives.

EXAMPLE 34

A therapeutic composition of sourdough bread made from flour, water, yeast, sourdough starter, and an additional oxalic acid ingredient selected from the group of dried, chopped parsley, freeze-dried chives, oxalic acid, oxalate, foods containing oxalic acid, foods containing oxalate, or combinations thereof to provide approximately 2 g. of oxalic acid per 4 lb. loaf of sourdough bread.

EXAMPLE 35

A method of therapeutically treating a warm-blooded animal including humans having the steps of periodically administering a portion of the sourdough bread of Example 34 to provide a dosage of oxalic acid of up to about 1 g. oxalic acid per day.

EXAMPLE 36

A method of delaying, preventing, controlling or treating the onset of Alzheimer's Disease, Hodgkin's Disease, Parkinson's Disease, and the like lessening the effects of the disease, or improving the quality of life of a person suffering from the disease having the steps of periodically administering a therapeutically effective amount of at least one therapeutically effective form of oxalic acid or oxalate.

EXAMPLE 37

A canine and feline urine oxalate level scale having above normal, normal, and below normal levels by weight of the animal and providing a quick-ready reference for a veterinarian or a pet owner to test urine oxalate levels and adjust the oxalic acid or oxalate intake of the canine or feline accordingly.

EXAMPLE 38

A method for causing the sloughing off of the inner surface of the intestinal membrane in a warm-blooded animal including humans having the steps of administering daily doses of a therapeutically effective amount of at least one therapeutically effective form of oxalic acid or oxalate such as dried parsley for a period of weeks or months thereby causing the sloughing off of the interior surface of the intestinal membrane and removing old bacteria, food, waste, and intestinal cells and membrane.

EXAMPLE 39

A method of treating or preventing oxalate nephrosis in animals including dogs, goats, humans, cattle and the like including periodically administering a therapeutically effective amount of at least one oxalic acid or oxalate blocker.

EXAMPLE 40

A composition for cleaning oral or dental bridgework made of a dilute solution of oxalic acid.

EXAMPLE 41

A composition for cleaning a toothbrush made of a dilute solution of oxalic acid.

EXAMPLE 42

A composition for cleaning and rinsing the interior surfaces of the mouth and teeth made of a dilute solution of oxalic acid and distilled water.

EXAMPLE 43

In a mouthwash, the improvement including the addition of a low concentration of oxalic acid.

EXAMPLE 44

In a tartar control rinse, the improvement being the addition of a small amount of oxalic acid.

EXAMPLE 45

A test kit for detecting the oxalate level in urine of warm-blooded animals including humans having a sample holder and a liquid reagent which upon addition of a selected quantity of reagent to a sample of urine in the sample holder provides a colormetric indication of the presence or absence of oxalate.

EXAMPLE 46

A meat tenderizer composition of a dilute solution of oxalic acid.

EXAMPLE 47

A dietary supplement for everyday optimum nutritional balance having between 0.5 to 1.5 g. of oxalic acid.

EXAMPLE 48

A test kit for detecting the presence and quantity of oxalic acid in a blood sample of a warm-blooded animal including humans having a sample support surface, a reagent, and a mixing container for mixing together the blood sample and reagent to allow the reagent to undergo a color change and provide a colormetric determination of the presence and quantity of oxalic acid in the sample.

EXAMPLE 49

A method of treating warm-blooded animals including the steps of testing the blood or urine oxalic acid or oxalate levels, administering oxalic acid, oxalate or blockers thereof, and monitoring the levels to determine if adjustments are necessary to achieve a desired level.

EXAMPLE 50

A composition for controlling, treating or managing neoplasia, tumors, brain tumors, cancer, growths, and the like, for preventing the new growth of different or abnormal cells or tissues, or for otherwise therapeutically treating warm-blooded animals including pets and humans and including at least one therapeutically effective form of oxalic acid or oxalate.

EXAMPLE 51

The composition as described in Example 50 wherein the therapeutically effective form of oxalic acid or oxalate is selected from the group of oxalic acid in a free acid, ester, lactone or salt form, oxalates including sodium oxalate, a nutritional supplement containing at least one form of oxalic acid or oxalate, oxalic acid dihydrate, anhydrous oxalic acid, oxamide, oxalate salts, natural or processed foods including molds, plants or vegetables including parsley, chives, garlic, beets, carrots, spinach, and the like containing at least one form of oxalic acid or oxalate, beverages, liquids or juices containing at least one form of oxalic acid or oxalate, additives containing at least one form of oxalic acid or oxalate, and combinations thereof.

EXAMPLE 52

The composition as described in Example 50 wherein the composition is oxalic acid dihydrate.

EXAMPLE 53

The composition as described in Example 50 wherein the composition is dried parsley.

EXAMPLE 54

The composition as described in Example 50 further having a pharmaceutically acceptable carrier or diluent for the therapeutically effective form of oxalic acid or oxalate.

EXAMPLE 55

The composition as described in Example 54 wherein the carrier or diluent is at least one of a gel cap and distilled water.

EXAMPLE 56

A method for controlling, treating or managing neoplasia, tumors, growths, cancers, abnormal cells or tissues and the like in warm-blooded animals including pets and humans having the steps of periodically administering a therapeutically effective dosage of the composition of Example 50.

EXAMPLE 57

The method as described in Example 56 wherein the composition is administered orally or sublingually in at least one of gel cap, tablet, powder, food additive, food, drops, liquid, beverage, pill and capsule form.

EXAMPLE 58

The method as described in Example 56 wherein the composition is administered by injection including venous injection, injection into the tumor, neoplasia, cancer, or growth, or injection adjacent the tumor, neoplasia, cancer, or growth.

EXAMPLE 59

The method as described in Example 56 wherein the composition is administered topically by at least one of transdermal patch, ointment, salve, cream, lotion, gel, solution, and the like.

EXAMPLE 60

The method as described in Example 56 wherein the composition is administered internally by at least one of inhalation, suppository, and subcutaneous deposit.

EXAMPLE 61

The method as described in Example 56 wherein the composition is administered at least once a day at a dosage of 50 mg to 6 g for humans or 1 mg to 3 g for pets.

EXAMPLE 62

The method as described in Example 56 further having the steps of reducing the intake of oxalic acid or oxalate blockers and/or increasing the intake of oxalic acid or oxalate enhancers.

EXAMPLE 63

The method as described in Example 62 wherein the blockers are selected from the group of citric acid, ascorbic acid, pyridoxine hydrochloride, calcium, alcohol, resins, clays, and combinations thereof.

EXAMPLE 64

The method as described in Example 62 wherein the blockers are selected from the group of dairy products including calcium, fruits, coconut, beverages containing alcohol, ascorbic acid or citric acid including adult beverages such as beer, wine, vodka, gin, and the like, fruit juice based beverages, soda pop or soft drinks containing ascorbic acid or citric acid, other sports drinks, beverages or refreshments containing ascorbic acid or citric acid, red meat or white meat of fowl including chicken, turkey, pheasant and the like containing pyridoxines, or other foods or beverages containing alcohol, citric acid, ascorbic acid or pyridoxine hydrochloride including breads or grains, and combinations thereof.

EXAMPLE 65

A composition for controlling, treating or managing hyperplasia including swollen or enlarged prostate, and the like, for preventing new swelling or enlargement of tissues, or for otherwise therapeutically treating warm-blooded animals including pets and humans and including at least one therapeutically effective form of oxalic acid or oxalate.

EXAMPLE 66

The composition as described in Example 65 wherein the therapeutically effective form of oxalic acid or oxalate is selected from the group of oxalic acid in a free acid, ester, lactone or salt form, oxalates including sodium oxalate, a nutritional supplement containing at least one form of oxalic acid or oxalate, oxalic acid dihydrate, anhydrous oxalic acid, oxamide, oxalate salts, natural or processed foods including molds, plants or vegetables including parsley, chives, garlic, beets, carrots, spinach, and the like containing at least one form of oxalic acid or oxalate, beverages, liquids or juices containing at least one form of oxalic acid or oxalate, additives containing at least one form of oxalic acid or oxalate, and combinations thereof.

EXAMPLE 67

A method for controlling, treating or managing hyperplasia including swollen or enlarged prostate, and the like, for preventing new swelling or enlargement of tissues, or for otherwise therapeutically treating warm-blooded animals including pets and humans having the steps of periodically administering a therapeutically effective dosage of the composition of Example 65.

EXAMPLE 68

The method as described in Example 67 further having the steps of reducing the intake of oxalic acid or oxalate blockers.

EXAMPLE 69

A diet for treating, controlling, and preventing cancer, tumors, neoplasia, and the like in warm-blooded animals including pets and humans having the steps of adding to the regular diet a dietary supplement of at least one therapeutically effective form of oxalic acid or oxalate.

EXAMPLE 70

The diet as described in Example 69 wherein the therapeutically effective form of oxalic acid or oxalate is selected from the group of oxalic acid in a free acid, ester, lactone or salt form, oxalates including sodium oxalate, a nutritional supplement containing at least one form of oxalic acid or oxalate, oxalic acid dihydrate, anhydrous oxalic acid, oxamide, oxalate salts, natural or processed foods including molds, plants or vegetables including parsley, chives, garlic, beets, carrots, spinach, and the like containing at least one form of oxalic acid or oxalate, beverages, liquids or juices containing at least one form of oxalic acid or oxalate, additives containing at least one form of oxalic acid or oxalate, and combinations thereof.

EXAMPLE 71

The diet as described in Example 69 further having the steps of reducing the intake of oxalic acid or oxalate blockers.

EXAMPLE 72

The diet as described in Example 71 wherein the blockers are selected from the group of citric acid, ascorbic acid, pyridoxine hydrochloride, calcium, alcohol, resins, clays, and combinations thereof.

EXAMPLE 73

The diet as described in Example 71 wherein the blockers are selected from the group of dairy products including calcium, fruits, coconut, beverages containing alcohol, ascorbic acid or citric acid including adult beverages such as beer, wine, vodka, gin, and the like, fruit juice based beverages, soda pop or soft drinks containing ascorbic acid or citric acid, other sports drinks, beverages or refreshments containing ascorbic acid or citric acid, red meat or white meat of fowl including chicken, turkey, pheasant, and the like containing pyridoxine, or other foods or beverages containing alcohol, citric acid, ascorbic acid or pyridoxine hydrochloride including breads or grains, and combinations thereof.

EXAMPLE 74

A veterinary composition for controlling, treating or managing neoplasia, tumors, brain tumors, cancer, growths, and the like, for preventing the new growth of different or abnormal cells or tissues, or for otherwise therapeutically treating warm-blooded animals including dogs and cats of a composition including at least one therapeutically effective form of oxalic acid or oxalate.

EXAMPLE 75

The veterinary composition as described in Example 74 wherein the therapeutically effective form of oxalic acid or oxalate is selected from the group of oxalic acid in a free acid, ester, lactone or salt form, oxalates including sodium oxalate, a nutritional supplement containing at least one form of oxalic acid or oxalate, oxalic acid dihydrate, anhydrous oxalic acid, oxamide, oxalate salts, natural or processed foods including molds, plants or vegetables including parsley, chives, garlic, beets, carrots, spinach, and the like containing at least one form of oxalic acid or oxalate, beverages, liquids or juices containing at least one form of oxalic acid or oxalate, additives containing at least one form of oxalic acid or oxalate, and combinations thereof.

EXAMPLE 76

The veterinary composition as described in Example 75 wherein the composition is oxalic acid dihydrate.

EXAMPLE 77

The veterinary composition as described in Example 75 wherein the composition is at least one of carrots, boiled carrots, and dried parsley.

EXAMPLE 78

The veterinary composition as described in Example 75 further having a pharmaceutically acceptable carrier or diluent for the therapeutically effective form of oxalic acid or oxalate.

EXAMPLE 79

The veterinary composition as described in Example 78 wherein the carrier or diluent is a gel cap or distilled water.

EXAMPLE 80

A veterinary method for controlling, treating or managing neoplasia, tumors, growths, cancers or abnormal tissues in warm-blooded animals including dogs and cats having the steps of periodically administering a therapeutically effective dosage of the veterinary composition of Example 75.

EXAMPLE 81

The veterinary method as described in Example 80 wherein the composition is administered orally or sublingually in at least one of gel cap, tablet, powder, food additive, food, beverage, pill and capsule form, by injection including venous injection, injection into the tumor, neoplasia, cancer, or growth, or injection adjacent the tumor, neoplasia, cancer, or growth, topically by at least one of transdermal patch, ointment, salve, cream, lotion, gel, solution, and the like, internally by inhalation, suppository or subcutaneous deposit, or combinations thereof.

EXAMPLE 82

The veterinary method as described in Example 80 wherein the composition is administered at least once a day at a dosage of about 1 mg to 3 g for dogs and cats.

EXAMPLE 83

The veterinary method as described in Example 80 further having the steps of reducing the intake of oxalic acid or oxalate blockers.

EXAMPLE 84

The veterinary method as described in Example 83 wherein the blockers are selected from the group of citric acid, ascorbic acid, pyridoxine hydrochloride, calcium, alcohol, resins, clays, and combinations thereof.

EXAMPLE 85

A method of treating warm-blooded animals including pets and humans afflicted with tumor cells sensitive to an oxalic acid compound including the steps of periodically administering to the animal an oncolytic amount of at least one therapeutically effective oxalic acid or oxalate compound.

EXAMPLE 86

A process for preparing an anti-tumor agent including the steps of mixing at least one therapeutically effective form of oxalic acid or oxalate with a pharmaceutically acceptable carrier or diluent.

EXAMPLE 87

The process as described in Example 86 wherein the therapeutically effective form of oxalic acid or oxalate is selected from the group of oxalic acid in a free acid, ester, lactone or salt form, oxalates including sodium oxalate, a nutritional supplement containing at least one form of oxalic acid or oxalate, oxalic acid dihydrate, anhydrous oxalic acid, oxamide, oxalate salts, natural or processed foods including molds, plants or vegetables including parsley, chives, garlic, beets, carrots, spinach, and the like containing at least one form of oxalic acid or oxalate, beverages, liquids or juices containing at least one form of oxalic acid or oxalate, additives containing at least one form of oxalic acid or oxalate, and combinations thereof.

EXAMPLE 88

The process as described in Example 86 wherein the pharmaceutically acceptable carrier or diluent is selected from the group of distilled water, heated water, pharmaceutically acceptable liquids, nutritional supplements, natural or processed foods, and the like.

EXAMPLE 89

A composition for treating autoimmune related diseases such as HIV, SLE, AIDS, BSE, CFS and the like having a therapeutically effective amount of at least one therapeutically effective form of oxalic acid or oxalate.

EXAMPLE 90

A method of treating, preventing or controlling autoimmune-related diseases such as AIDS, HIV, SLE, BSE, CFS and the like, preventing, lessening or controlling the destruction of the body's immune system, or purifying the blood including the steps of periodically administering a therapeutically effective amount of the composition of Example 89.

EXAMPLE 91

A composition for counteracting the decomposition or reduction of oxalic acid or oxalate caused by radiation exposure, radiation treatment, X-rays, strong electromagnetic waves or fields, and the like or for returning the body's oxalic acid or oxalate level to at least a normal level following radiation treatment, X-rays, CAT-scans, MRI-scans, and the like including a therapeutically effective amount of at least one therapeutically effective form of oxalic acid or oxalate.

EXAMPLE 92

A method for counteracting the decomposition or reduction of oxalic acid or oxalate caused by radiation exposure, radiation treatment, X-rays, strong electromagnetic waves or fields, and the like or for returning the body's oxalic acid or oxalate level to at least a normal level following radiation treatment, X-rays, CAT-scans, MRI-scans, and the like having the steps of administering a therapeutically effective amount of the composition of Example 91 following the treatment or exposure.

EXAMPLE 93

The method as described in Example 92 further including the steps of administering a therapeutically effective amount of the composition of Example 91 prior to the treatment or exposure.

EXAMPLE 94

A method of enhancing the therapeutic effect of oxalic acid or oxalate including the steps of decreasing or eliminating the ingestion or administration of one or more of oxalic acid or oxalate blockers.

EXAMPLE 95

The method as described in Example 94 wherein the blockers are selected from the group of calcium, alcohol, citric acid, ascorbic acid, pyridoxine hydrochloride, and combinations thereof.

EXAMPLE 96

A method of treating brain tumors including the steps of ingesting or administering a therapeutically effective amount of at least one therapeutically effective form of oxalic acid or oxalate.

EXAMPLE 97

The method as described in Example 96 wherein the therapeutically effective form of oxalic acid or oxalate is dried chopped parsley.

EXAMPLE 98

A treatment regimen for treating tumors, cancers, growths, neoplasia and the like including brain tumors, breast cancer, cervical cancer, and others including the steps of reducing or eliminating the ingestion or administration of oxalic acid or oxalate blockers, administering or ingesting high dosages of oxalic acid or oxalate to raise the blood or urine oxalic acid or oxalate level above normal, and, after cleansing the blood of tumor, cancer or abnormal cells, administering or ingesting a more moderate level of oxalic acid or oxalate to maintain a normal blood or urine oxalic acid or oxalate level.

EXAMPLE 99

The regimen as described in Example 98 further including the steps of increasing the administration or ingestion of oxalic acid or oxalate enhancers.

EXAMPLE 100

A therapeutic composition in cream or ointment form for topical administration of oxalic acid or oxalate having at least one therapeutically effective form of oxalic acid or oxalate, a solvent, and a cream or ointment base.

EXAMPLE 101

The therapeutic composition as described in Example 100 wherein the solvent is distilled water, acetone, propylene glycol, or polysorbate, and the base is a cream, ointment, gel, lotion, spray, stick, or powder base.

EXAMPLE 102

A method of producing the therapeutic composition as described in Example 100 having the steps of mixing a dilute concentration of at least one therapeutically effective form of oxalic acid or oxalate with a solvent such as distilled water, acetone, propylene glycol, polysorbate or the like to form a solution, mixing the solution with a base such as a hydrophilic petrolatum, cream, ointment, gel, lotion, spray, stick, powder or other base.

EXAMPLE 103

In pet food, the improvement of the addition of a therapeutically effective quantity of at least one therapeutically effective form of oxalic acid or oxalate.

EXAMPLE 104

In pet food, the improvement of the elimination or reduction of oxalic acid or oxalate blockers.

EXAMPLE 105

A method of treating tumors, cancers, growths, neoplasia and the like including brain tumors, breast cancer, cervical cancer, and others in a person suffering from osteoporosis including the steps of reducing or eliminating the ingestion or administration of oxalic acid or oxalate blockers, administering or ingesting high dosages of oxalic acid or oxalate to raise the blood or urine oxalic acid or oxalate level above normal, and, after cleansing the blood of tumor, cancer or abnormal cells, reducing or eliminating the administration or ingestion of oxalic acid or oxalate to maintain a below normal blood or urine oxalic acid or oxalate level.

EXAMPLE 106

A method of treating osteoporosis including the steps of increasing calcium intake and decreasing oxalic acid or oxalate intake.

EXAMPLE 107

A therapeutic composition for purifying the blood, controlling, treating or eradicating abnormal cells, controlling, treating or affecting cholesterol plaque and fat buildup in the cardiovascular system or in the brain, and maintaining good cardiovascular health and operation having a therapeutically effective amount of at least one therapeutically effective form of oxalic acid or oxalate.

EXAMPLE 108

An oral rinse or wash for smokers or snuff users for controlling, treating or managing neoplasia, tumors, cancers, growths, and the like, for preventing the new growth of different or abnormal tissues, or for otherwise therapeutically treating the mouth area of a dilute solution of at least one therapeutically effective form of oxalic acid or oxalate.

EXAMPLE 109

A method of manufacturing a dry processed dog food containing at least one form of oxalic acid or oxalate including the steps of mixing a slurry of conventional dog food ingredients together with a dilute solution of oxalic acid or oxalate in heated water to form an oxalic acid or oxalate containing slurry, forming the slurry into pellets and drying the pellets.

EXAMPLE 110

The method as described in Example 109 wherein the oxalic acid is oxalic acid dihydrate and each pellet contains approximately 1 mg of oxalic acid so that one pound of dry dog food contains about 1 g of oxalic acid.

EXAMPLE 111

A dietary supplement for treating a patient diagnosed with an active cancer, tumor, growth, or neoplasia having about 1 g to 6 g, preferably 2 g to 4 g of oxalic acid per day based on 70 kilograms of body weight and a pharmaceutically acceptable carrier or diluent.

EXAMPLE 112

A composition for treating parvo virus in animals including canines of a therapeutically effective amount of at least one therapeutically effective form of oxalic acid or oxalate.

EXAMPLE 113

A pharmaceutical composition to be administered orally to humans of a mixture of a non-toxic ingestible carrier and a therapeutically effective form of oxalic acid or oxalate.

EXAMPLE 114

The pharmaceutical composition as described in Example 113 wherein the composition is provided in a form selected from the group of pills, powders, granules, tablets, microcapsules, gel capsules, nutritional supplements, processed foods, liquids, drops, beverages, additives and solutions.

EXAMPLE 115

In a pet treat such as a jerky strip, dog bone, chew, rawhide, and the like, the improvement of the addition of microgram amounts of at least one therapeutically effective form of oxalic acid or oxalate, whereby the treats provide for the maintenance of good pet health.

EXAMPLE 116

Treatment For Tumor Reduction

Our research indicates the following as a treatment for the reduction of tumors:

Carrots, spinach, parsley, chives, beets and beet leaves, garlic, collards and radishes are high among vegetables containing Oxalic Acid and should be eaten in order to build a high concentration of acid in the body fluids. Almonds, cashews, peanuts, and, especially walnuts which are high in oleic and linoleic fatty acids and increase oxalic acid absorption may be eaten.

Red meats, chicken and turkey breasts, (generally white meat) are considered high in Pyridoxine (vitamin B6), and should be avoided during the treatment, alcohol and products containing Citric Acid (soda pop, other soft drinks and thirst quenchers are generally high in citric acid), and Ascorbic Acid (vitamin C) are considered blockers of Oxalic Acid and should be avoided since they retard the build up of Oxalic Acid in the system. It is absolutely necessary to read the ingredients on all food and drinks consumed while on the diet. Citric and Ascorbic acids are widely used as a preservative in many products, including frozen and bakery goods.

All dairy products should also be avoided while following the treatment. Calcium inhibits Oxalic Acid and when combined can form calcium oxalate stones (kidney).

Coffee, cocoa, regular tea, made with distilled water, and natural fruit juices are acceptable for drinking. All beverages should be free of citric acid.

As Oxalic Acid is built up in the system one may experience indigestion known as heart burn or a nagging backache. These indicate that the acid is being ingested in too large a quantity or the system is digesting the acid at a rate faster than it can be absorbed. Indigestion can be relieved by taking 2 or 3 teaspoonful of crushed pineapple. Relief for the backache can be accomplished by taking one 100 mg vitamin B6 pill. A slight reduction of the intake of Oxalic Acid will avoid either of the above conditions. Maximum effect of Oxalic Acid on tumor reduction would be accomplished if a acid level can be maintained just below the discomfort level.

Our research shows that five to seven days after start of the treatment, an increase in energy will be experienced. Some people notice a body weight loss. Improvement in condition of the tumor should be noticed after 10 to 12 days.

If there are multiple tumors, the newest tumors will regress first, while older (core) tumors will require a longer time. Once tumors begin to shrink and disappear and when finally all trace of cancer has been cleared in the blood system a balanced diet of all foods may be resumed while being sure to maintain an adequate level of Oxalic Acid in the system to prevent resumption of tumor growth.

The microwave should not be used for cooking or heating any foods or beverage in the diet because it reduces the strength or amount of the Oxalic Acid.

EXAMPLE 117

Oxalic Acid Dietary Plan

Our research indicates the following as a diet for the reduction of tumors:

Carrots, spinach, parsley, chives, beets and beet leaves, garlic, collards and radishes are high among vegetables containing oxalic acid or oxalate and should be eaten in order to build a high concentration of oxalic acid in the body fluids. Almonds, cashews, peanuts, and, especially walnuts which are high in oleic and linoleic fatty acids and increase oxalic acid absorption may be eaten.

Red meats, chicken and turkey breasts, (generally white meat) are considered high in Pyridoxine (vitamin B6), and should be avoided during the treatment, alcohol and products containing Citric Acid (soda pop, other soft drinks and thirst quenchers are generally high in citric acid), and Ascorbic Acid (vitamin C) are considered blockers of oxalic acid or oxalate and should be avoided since they retard the build up of oxalic acid in the system. It is absolutely necessary to read the ingredients on all food and drinks consumed while on the diet. Citric and Ascorbic acids are widely used as a preservative in many products, including frozen and bakery goods.

All dairy products should also be avoided while following the treatment. Calcium inhibits oxalic acid and when combined can form calcium oxalate stones (kidney).

Coffee, cocoa, regular tea, made with distilled water, and limited amounts of natural fruit juices are acceptable for drinking. All beverages should be free of citric acid.

As oxalic acid is built up in the system one may experience indigestion known as heart burn or a nagging backache. These are indicators that the oxalic acid is being ingested in too large a quantity or the system is digesting the acid at a rate faster than it can be absorbed. Indigestion can be relieved by taking 2 or 3 teaspoonful of crushed pineapple. Relief for the backache can be accomplished by taking one 100 mg vitamin B6 pill. A slight reduction or moderation of the intake of oxalic acid or oxalate will avoid either of the above conditions. Maximum effect of Oxalic Acid on tumor reduction would be accomplished if an oxalic acid level can be maintained just below the discomfort level.

Our research shows that five to seven days after start of the treatment, an increase in energy will be experienced. Some people notice a body weight loss. Improvement in condition of the tumor should be noticed after 10 to 12 days.

If there are multiple tumors, the newest tumors will regress first, while older (core) tumors will require a longer time. Once tumors begin to shrink and disappear and when finally all trace of cancer has been cleared in the blood system a balanced diet of all foods may be resumed while being sure to maintain an adequate level of oxalic acid or oxalate in the system to prevent resumption of tumor growth.

The microwave oven should not be used for cooking or heating any foods or beverage in the diet because it reduces the strength or amount of the oxalic acid.

EXAMPLE 118

Protocol for Treatment of Canine, Equine, Feline Species for the Control of Neoplasia (tumors)

Research and Development Phase

Prior to the commencement of protocol a complete examination should be accomplished by the attending veterinarian.

The examiner should complete and record the following:

History since the onset of the neoplasia based on owners description.

Specific diet, to include all treats, and liquid intake.

General activity level during previous period.

Age.

Weight.

General examination.

Physical examination to determine the location, type, and size of the tumor(s). MRI, CAT-scan, or X-ray should be used if procedure is available.

Blood analysis, including (CBC) liver and kidney profiles.

Urine analysis, including analysis for oxalates.

Based on veterinarian's diagnosis of the animal's condition, the maximum amount of Oxalic Acid or Oxalate Neoplasia Control Formula will be recommended for the first 14 days. At the completion of 14 days, a blood and urine analysis will be completed and if results are satisfactory, the animal will be placed on a diet, based on the animal's weight, of regular dry dog food, supplemented by Oxalic Acid or Oxalate Neoplasia Control Formula. Dosage will be at the maximum computed on the above blood and urine analysis. Repeat urine checks will be completed, as determined by the veterinarian, and the amount of Oxalic Acid or Oxalate Neoplasia Formula will be adjusted as required.

After initiation of the protocol the veterinarian will observe the level of oxalates in the urine. The urine oxalate level will be maintained at the desired level, based on the weight of the animal, using Urine Oxalate Scales of the present invention.

EXAMPLE 119

Animal Feed Supplement Mixes

The supplement is to be added to the normal feed/food, by weight, to add the amount of oxalic acid desired.

Equine Mix

Ingredients

Ground oats, ground corn, ground barley, wheat middlings, soybean meal, cane molasses, dried hydrolyzed whey, dried whey, soy flour, animal fat, vegetable fat, dehydrated alfalfa meal, dicalcium phosphate, calciumcarbonate, salt, magnesium sulfate, potassium sulfate, smectite, vermiculite, ferrous sulfate, ferric choline citrate, zinc oxide, manganous oxide, copper oxide, copper sulfate, cobalt carbonate, ethylene diamine dihydroiodide, sodium selenite, oxalic acid.

Feline Mix

Ingredients

Ground corn, poultry by-product meal, corn gluten meal animal fat, (preserved with BHA propyl gallate), brewers rice, chicken liver digest, potassium chloride, choline chloride, calcium sulfate, taurine, ethoxyquin, (a preservative), ferrous sulfate, zinc oxide, copper chloride, manganous oxide, cobalt carbonate, calcium iodate, sodium selenite, oxalic acid.

Canine Mix

Ingredients

Ground corn, soybean meal, meat and bone meal, soy whole, beet pulp, salt, corn gluten meal, soy oil, dicalcium phosphate, poultry fat, oxalic acid.

In each of the above feed supplements oxalic acid is added at one gram of oxalic acid to one pound of dried food. Crude protein, crude fat, crude fiber, and moisture will be blended at different formula for the life stage of the animals.

Oxalic acid feed supplement will be added to the daily diet as determined by the attending veterinarian for each of the above mixes.

EXAMPLE 120

Supplement Mixes

The supplement is to be added to the normal feed/food, by weight, to add the amount of oxalic acid or oxalate desired.

Equine Mix

Ingredients

Ground oats, ground corn, ground barley, wheat middlings, soybean meal, cane molasses, dried hydrolyzed whey, dried whey, soy flour, animal fat, vegetable fat, dehydrated alfalfa meal, dicalcium phosphate, calciumcarbonate, salt, magnesium sulfate, potassium sulfate, smectite, vermiculite, ferrous sulfate, ferric choline citrate, zinc oxide, manganous oxide, copper oxide, copper sulfate, cobalt carbonate, ethylene diamine dihydroiodide, sodium selenite, oxalic acid or oxalate.

Feline Mix

Ingredients

Ground corn, poultry by-product meal, corn gluten meal animal fat, (preserved with BHA propyl gallate), brewers rice, chicken liver digest, potassium chloride, choline chloride, calcium sulfate, taurine, ethoxyquin, (a preservative), ferrous sulfate, zinc oxide, copper chloride, manganous oxide, cobalt carbonate, calcium iodate, sodium selenite, oxalic acid or oxalate.

Canine Mix

Ingredients

Ground corn, soybean meal, meat and bone meal, soy whole, beet pulp, salt, corn gluten meal, soy oil, dicalcium phosphate, poultry fat, oxalic acid or oxalate.

In each of the above feed supplements oxalic acid or oxalate is added at one gram of oxalic acid or oxalate to one pound of dried food. Crude protein, crude fat, crude fiber, and moisture will be blended at different formula for the life stage of the animals.

The feed supplement will be added to the daily diet as determined by the attending veterinarian for each of the above mixes.

EXAMPLE 121

Canine Supplement Mix

The supplement is to be added to the normal feed/food, by weight, to add the amount of oxalic acid or oxalate desired.

Ingredients

Ground corn about 55.99%, soybean meal 8.53%, meat and bone meal 15.85%, soy whole 2.54%, beet pulp 1.9%, salt 0.45%, corn gluten meal 9.35%, soy oil 1.87%, dicalcium phosphate 0.47%, poultry fat 3.00%, oxalic acid 0.0023% with moisture about 0–10%.

In the above feed supplement oxalic acid or oxalate is added at about one gram of oxalic acid or oxalate to one pound of dried food. Crude protein, crude fat, crude fiber, and moisture will be blended at different formula for the life stage of the animals.

The feed supplement will be added to the daily diet as recommended by the attending veterinarian.

EXAMPLE 122

A method of counteracting the deleterious effects of a mammogram, CAT-scan, X-ray and the like exposure or treatment including the steps of about 3 weeks prior to the exposure increasing the intake of oxalic acid or oxalate, continuing the increased oxalic acid or oxalate during the treatment and for 3 weeks following treatment. Thereafter, checking the blood or urine oxalic acid or oxalate levels of the patient and if they are normal, continuing with that level of intake of oxalic acid or oxalate, if they are above normal, reducing the intake of oxalic acid or oxalate, and if they are below normal, increasing the intake of oxalic acid or oxalate. Thereafter, monitoring the levels and adjusting the intake on a periodic basis.

EXAMPLE 123

An oxalic acid or oxalate containing bread including about 1 gram of oxalic acid or oxalate per loaf of bread.

EXAMPLE 124

The bread of Example 123 wherein the oxalic acid is oxalic acid dihydrate dissolved in distilled water prior to being added to the bread during manufacturing of the loaf.

EXAMPLE 125

The bread of Example 124 further containing about 2 cups of trail mix including nuts, dried fruits, and the like per loaf of bread with the trail mix being added during the manufacture of the loaf.

EXAMPLE 126

A dry dogfood is prepared with 300 lbs. of dry dogfood having added thereto 10½ ounces of oxalic acid dihydrate to provide about 1 gram of oxalic acid per pound of dry dogfood. The oxalic acid dihydrate powder is added to 90° C. distilled water and mixed into the conventional dogfood slurry.

EXAMPLE 127

The dogfood of Example 126 with the exception that any vitamin B6 is removed from the conventional dry mix.

EXAMPLE 128

An oxalic acid intake adult management control plan includes four phases. In the first phase, the adult is administered about 1¾ to 2 grams of oxalic acid or oxalate per day for 5–7 days to eliminate abnormal cells or otherwise clean the blood of the patient for a 70 kilogram weight adult. For larger adults, the dosage would have to be increased. Also, oxalic acid and oxalate levels are checked in the blood, plasma and/or urine to determine the exact amount of oxalic acid or oxalate required for the individual subject. In the second phase of the treatment, the subject is given about ¾ gram of oxalic acid or oxalate for an additional 15–20 days until the growth or expansion of the tumor or malignancy has stopped and the tumor is in regression or inert. In the third phase the subject is given about ½ gram of oxalic acid or oxalate per day to continue tumor reduction or until the body is clean. In the fourth phase or maintenance phase, the subject is given about 50 mg of oxalic acid or oxalate per day for maintenance of good health and to keep all cancers in remission or in check. Again, these dosages are provided for an average 70 kilogram adult and the individual's oxalic acid or oxalate levels need to be checked periodically and the dosages adjusted as necessary.

EXAMPLE 129

The control plan of Example 128 wherein a computer model of the chemical balance of the human body is used in addition to the oxalic acid and oxalate level information to determine the proper dosage for that individual.

EXAMPLE 130

An animal testing method for testing for example the carcinogenic effect of one or more agents or irritants on an animal such as a mouse or rat, including the steps of determining the normal oxalic acid or oxalate blood or urine level of the animal, irradiating the animal to weaken its natural immune system, and administering a dosage of oxalic acid or oxalate to the animal as necessary to bring its oxalic acid or oxalate blood or urine level back up to a normal level prior to further testing of the animal.

EXAMPLE 131

A method of treating an animal suffering from bovine spongiform encephalopathy (BSE) by feeding the animal a feed high in oxalic acid or oxalate, for example Halogeton or Setavia plants or grass.

EXAMPLE 132

The method of Example 131 including the step of treating the animal directly by an intraveneous administration of oxalic acid.

EXAMPLE 133

A method of treating humans having Creutzfeldt-Jakob Disease (CFS) by administering a therapeutic quantity of at least one therapeutically effective form of oxalic acid or oxalate.

EXAMPLE 134

The method of Example 133 including the step of administering oxalic acid directly by intravenous administration.

EXAMPLE 135

A method of preventing BSE or CFS in warm blooded animals including cattle and humans including the steps of increasing the intake of at least one form of oxalic acid or oxalate.

EXAMPLE 136

A method of treating animals using oxalic acid or oxalate in place of chemotherapy and administering at least one therapeutically effective form of oxalic acid or oxalate continuously to the patient in decreasing amounts to treat, control, or prevent cancer, tumors, growths, bacterial disease, viral disease, chemical disease and the like without deleteriously affecting normal cells.

EXAMPLE 137

A method of enhancing the beneficial effects of oxalic acid or oxalate in animals including humans and pets including the steps of eliminating the use of microwave cooking for heating food or drink of the animal to prevent the decomposition or reduction in the amount of oxalic acid or oxalate in their food or drink.

EXAMPLE 138

The method of Example 137 further including the step of eliminating the use of the microwave oven for cooking or heating to prevent exposure to microwaves and thereby prevent decomposition or reduction in oxalic acid or oxalate in the animal being exposed.

EXAMPLE 139

The method of Example 138 further including the steps of eliminating the use of radiation, X-ray, CAT-scan, mammogram, strong electromagnetic waves, excessive heat, or other exposures or treatments which would decompose or reduce the amount of oxalic acid or oxalate in the animal.

EXAMPLE 140

A mouthwash containing a dilute solution of oxalic acid and having a pH of about 2.67.

EXAMPLE 141

An oxalic acid or oxalate containing drink including carrot juice having a pH of about 6.41.

EXAMPLE 142

A mouthwash or oral rinse containing a dilute solution of 500 milligrams of oxalic acid dihydrate per 500 milliliters of distilled water.

EXAMPLE 143

A method of treating terminally ill animals including adult humans including the steps of administering a high dosage of oxalic acid or oxalate to cleanse the blood and treat the condition or disease.

EXAMPLE 144

The method of Example 143 further including the steps of stopping chemotherapy treatments to prevent the weakening of the body and prevent the decomposition or reduction of oxalic acid or oxalate in the body.

EXAMPLE 145

The method of Example 143 further including the steps of reducing the dosage of oxalic acid or oxalate after the blood has been cleansed and the condition or disease has improved.

EXAMPLE 146

The method of Examples, 143, 144, or 145 further including the step of reducing the intake of oxalic acid or oxalate blockers and increasing the intake of oxalic acid or oxalate enhancers.

TABLE I

Oxalic Acid Content of Selected Vegetables

| Vegetable | Oxalic Acid (g/100 g) |
|---|---|
| Amaranth . . . | 1.09 |
| Asparagus . . . | .13 |
| Beans, snap . . . | .36 |
| Beet leaves . . . | .61 |
| Broccoli . . . | .19 |
| Brussels sprouts . . . | .36 |
| Cabbage . . . | .10 |
| Carrot . . . | .50 |
| Cassava . . . | 1.26 |
| Cauliflower . . . | .15 |
| Celery . . . | .19 |
| Chicory . . . | .21 |
| Chives . . . | 1.48 |
| Collards . . . | .45 |
| Coriander . . . | .01 |
| Corn, sweet . . . | .01 |
| Cucumbers . . . | .02 |
| Eggplant . . . | .19 |
| Endive . . . | .11 |
| Garlic . . . | .36 |
| Kale . . . | .02 |
| Lettuce . . . | .33 |
| Okra . . . | .05 |
| Onion . . . | .05 |
| Parsley . . . | 1.70 |
| Parsnip . . . | .04 |
| Pea . . . | .05 |
| Pepper . . . | .04 |
| Potato . . . | .05 |
| Purslane . . . | 1.31 |
| Radish . . . | .48 |
| Rutabaga . . . | .03 |
| Spinach . . . | .97 |
| Squash . . . | .02 |
| Sweetpotato . . . | .24 |
| Tomato . . . | .05 |
| Turnip . . . | .21 |
| Turnip greens . . . | .05 |
| Watercress . . . | .31 |

TABLE II

Oxalic Acid Contents of Foods

| Food | Method of Preparation | Oxalic acid[a] (mg/100 g of fresh material) |
|---|---|---|
| Vegetables | | |
| Asparagus | Fresh | 1.7 |
| Bean, runner | Boiled | 7.2–61.8 |
| Beetroot | Boiled | 96.8–121.0 |
| Brussels sprouts | Boiled | 2.1–3.6 |
| Cabbage | Boiled | 0.6–2.0 |
| Carrot | Boiled | 7.4–22.7 |
| Cauliflower | Boiled | 1.1 |
| Celery | Fresh | 13.0–17.5 |
| Chive | Fresh | 1.1 |
| Lettuce | Fresh | 1.7–2.7 |
| Marrow | Fresh | 0.5 |
| Mushroom | Fresh | 2.0 |
| Onion | Boiled | 3.0 |
| Parsley | Fresh | 166.0 |
| Pea, green | Boiled | 0.8–1.3 |
| Potato | Boiled | 2.3–7.1 |
| Radish | Fresh | 0.3 |
| Rhubarb | Stewed | 260–620 |
| Spinach | Boiled | 356–780 |
| Tomato | Fresh | 5.3 |
| Turnip | Boiled | 0.8 |
| Fruit | | |
| Apple | Fresh | 1.5 |
| Apricot | Fresh | 2.8 |
| Banana, ripe | Fresh | 0.7 |
| Gooseberry | Stewed | 2.6 |
| Grapefruit | Fresh | 0.0–6.6 |
| Melon | Fresh | 2.7 |
| Orange | Fresh | 6.2 |
| Peach | Canned | 1.2–3.7 |
| Pear | Canned | 1.3–1.7 |
| Pineapple | Canned | 0.0–3.7 |
| Plum | Stewed | 1.1–3.4 |
| Raspberry | Fresh | 2.2 |
| Strawberry | Fresh | 1.9–11.5 |
| Preserves | | |
| Jam, red plum | — | 0.5 |
| Jam, strawberry | — | 9.4 |
| Marmalade | — | 4.5–10.8 |
| Meat | | |
| Bacon, streaky | Fried | 0.6–3.3 |
| Beef | Roasted | 0.2 |
| Beef, corned | Fresh | 0.2 |
| Chicken | Roasted | 0.3–1.9 |
| Ham | Steamed | 0.4–1.6 |
| Kidney | Braised | 1.6–5.1 |
| Liver | Braised | 3.6–7.1 |
| Mutton | Roasted | 1.6 |
| Pork | Roasted | 1.7 |
| Soups | | |
| Chicken (Fray Bentos) | Heated | 3.0 |
| Oxtail (Fray Bentos) | Heated | 1.0 |
| Dairy products | | |
| Butter | Fresh | 0.0 |
| Cheese, Cheshire | Fresh | 0.0 |
| Eggs, whole | Boiled | 0.0–0.9 |
| Margarine | Fresh | 0.0 |
| Milk, cow | Fresh | 0.5–0.9 |
| Fish | | |
| Haddock | Boiled | 0.2 |
| Plaice | Boiled | 0.3 |
| Sardines | Canned | 1.6–4.8 |
| Cereals | | |
| Biscuits (Marie) | — | 4.5–13.8 |
| Bread, white | Fresh | 4.9–8.6 |
| Bread, Allinson's | Fresh | 15.8–26.3 |
| Cake, fruit | — | 11.8 |
| Cake, sponge | — | 7.4 |
| Cornflakes | — | 4.4–5.6 |
| Corn cob | Fresh | 9.1 |
| Oatmeal porridge | Cooked | 1.0 |
| Rice pudding | Cooked | 0.0 |
| Chocolate | | |
| Cadbury's plain | — | 123.5 |
| Cadbury's milk | — | 56.2 |
| Beverages | | |
| Beer, mild | Draught | 0.9–1.6 |
| Beer, bitter | Draught | 0.9–1.9 |
| Beer (Double Diamond) | Draught | 0.8 |
| Beer (Double Diamond) | Bottled | 1.9–2.0 |
| Beer (Guinness) | Draught | 1.4 |
| Beer (Guinness) | Bottled | 2.8–3.9 |
| Cocoa (Rowntree's) | Powder | 623.0 |

TABLE II-continued

Oxalic Acid Contents of Foods

| Food | Method of Preparation | Oxalic acid[a] (mg/100 g of fresh material) |
|---|---|---|
| Coca Cola | Canned | 1.12 |
| Coffee, infusion | 2 g per 100 ml, infused 5 min. | 1.0 |
|  | 4.4 g per 100 ml, infused 13 min. | 7.3 |
| Coffee essence (Camp) | Undiluted | 9.0 |
| Coffee (Nescafe) | Powder | 57.0–230.0 |
| Dandelion coffee | Powder | 25.0 |
| Horlicks | Powder | 4.1 |
| Lager (Skol) | Draught | 0.6 |
| Lemon squash (Robertson's) | — | 1.5 |
| Lucozade | — | 0.1 |
| Orange squash (Robertson's) | — | 1.2 |
| Ovaltine | Powder | 45.9 |
| Oxo cubes | — | 1.6 |
| Tea, leaves | Fresh, dried | 375–1,450 |
| Tea, infusion | 1 g per 100 ml, infused 2 min. | 4.6 |
|  | 2.0 g per 100 ml, infused 2 min. | 7.0–10.8 |
|  | 2.0 g per 100 ml, infused 5 min. | 10.1–14.5 |
|  | 2.0 g per 100 ml, infused 10 min. | 11.5–16.1 |
|  | 2.0 g per 100 ml, infused 15 min. | 12.6–17.2 |
| Wine, Beaujolais | — | 3.1 |

[a]Expressed as the anhydrous acid $(COOH)_2$.
From Oxalic Acid in Biology and Medicine, Pgs. 196–199.

TABLE III

Oxalate Content of Foods per 100 GM. EDIBLE PORTION

| FOOD | OXALATE mg. |
|---|---|
| Cereal and Cereal Products |  |
| Bread, white | 4.9 |
| Cake, fruit | 11.8 |
| Cake, sponge | 7.4 |
| Cornflakes | 2.0 |
| Crackers, soybean | 207.0 |
| Egg noodle (chow mein) | 1.0 |
| Grits (white corn) | 41.0 |
| Macaroni, boiled | 1.0 |
| Oatmeal, porridge | 1.0 |
| Spaghetti, boiled | 1.5 |
| Spaghetti in tomato sauce | 4.0 |
| Wheat germ | 269.0 |
| Milk and Milk Products |  |
| Butter | 0.0 |
| Cheese, cheddar | 0.0 |
| Margarine | 0.0 |
| Milk | 0.15 |
| Meats and Eggs |  |
| Bacon, streaky fried | 3.3 |
| Beef, canned corned | 0.0 |
| Beef, topside roast | 0.0 |
| Chicken, roast | 0.0 |
| Eggs, boiled | 0.0 |
| Fish: |  |
| Haddock | 0.2 |
| Plaice | 0.3 |
| Sardines | 4.8 |
| Ham | 1.6 |
| Hamburger, grilled | 0.0 |
| Lamb, roast | trace |
| Liver | 7.1 |
| Pork, roast | 1.7 |
| Vegetables |  |
| Asparagus | 5.2 |
| Beans, green boiled | 15.0 |
| Beans in tomato sauce | 19.0 |
| Beetroot, boiled | 675.0 |
| Beetroot, pickled | 500.0 |
| Broccoli, boiled | trace |
| Brussels sprouts, boiled | 0.0 |
| Cabbage, boiled | 0.0 |
| Carrots, canned | 4.0 |
| Cauliflower, boiled | 1.0 |
| Celery | 20.0 |
| Chard, Swiss | 645.0 |
| Chive | 1.1 |
| Collards | 74.0 |
| Corn, yellow | 5.2 |
| Cucumber, raw | 1.0 |
| Dandelion greens | 24.6 |
| Eggplant | 18.0 |
| Escarole | 31.0 |
| Kale | 13.0 |
| Leek | 89.0 |
| Lettuce | 3.0 |
| Lima beans | 4.3 |
| Mushrooms | 2.0 |
| Mustard greens | 7.7 |
| Okra | 146.0 |
| Onion, boiled | 3.0 |
| Parsley, raw | 100.0 |
| Parsnips | 10.0 |
| Peas, canned | 1.0 |
| Pepper, green | 16.0 |
| Pokeweed | 476.0 |
| Potatoes, white boiled | 0.0 |
| Potatoes, sweet | 56.0 |
| Radishes | 0.3 |
| Rice, boiled | 0.0 |
| Rutabagas | 19.0 |
| Spinach, boiled | 750.0 |
| Spinach, frozen | 600.0 |
| Squash, summer | 22.0 |
| Tomatoes, raw | 2.0 |
| Turnips, boiled | 1.0 |
| Watercress, early fine curled | 10.0 |
| Fruits |  |
| Apples, raw | 3.0 |
| Apricots | 2.8 |
| Avocado | 0.0 |
| Banana, raw | trace |
| Berries: |  |
| Black | 18.0 |
| Blue | 15.0 |
| Dew | 14.0 |
| Green goose | 88.0 |
| Raspberries, black | 53.0 |
| Raspberries, red | 15.0 |
| Strawberries, canned | 15.0 |
| Strawberries, raw | 10.0 |
| Cherries: |  |
| Bing | 0.0 |
| Sour | 1.1 |
| Currants: |  |
| Black | 4.3 |
| Red | 19.0 |
| Fruit salad, canned | 12.0 |

TABLE III-continued

Oxalate Content of Foods per 100 GM. EDIBLE PORTION

| FOOD | OXALATE mg. |
|---|---|
| Grapes: | |
| Concord | 25.0 |
| Thompson, seedless | 0.0 |
| Lemon Peel | 83.0 |
| Lime Peel | 110.0 |
| Mangoes | 0.0 |
| Melons: | |
| Cantaloupe | 0.0 |
| Casaba | 0.0 |
| Honeydew | 0.0 |
| Watermelon | 0.0 |
| Nectarines | 0.0 |
| Orange, raw | 4.0 |
| Peaches: | |
| Alberta | 5.0 |
| canned | 1.2 |
| Hiley | 0.0 |
| Stokes | 1.2 |
| Pears: | 3.0 |
| Bartlett, canned | 1.7 |
| Pineapple, canned | 1.0 |
| Plums: | |
| Damson | 10.0 |
| Golden gage | 1.1 |
| Green gage | 0.0 |
| Preserves: | |
| Red plum jam | 0.5 |
| Strawberry jam | 9.4 |
| Prunes, Italian | 5.8 |
| Rhubarb: | |
| canned | 800.0 |
| stewed, no sugar | 860.0 |
| Nuts | |
| Peanuts, roasted | 187.0 |
| Pecans | 202.0 |
| Confectionery | |
| Chocolate, plain | 117.0 |
| Jelly, with allowed fruit | 0.0 |
| Marmalade | 10.8 |
| Sweets, boiled (plain candies) | 0.0 |
| Beverages, Non-alcoholic | |
| Barley water, bottled | 0.0 |
| Coca-Cola | trace |
| Coffee (0.5 g Nescafe/100 ml) | 3.2 |
| Lemon Squash drink (lemonade) | 1.0 |
| Lucozade, bottled (soda) | 0.0 |
| Orange Squash drink (orangeade) | 2.5 |
| Ovaltine drink, 2 gm in 100 ml | 10.0 |
| Pepsi-Cola | trace |
| Ribena, concentrate (black currant drink) | 2.0 |
| Tea, Indian: | |
| 2 min. infusion | 55.0 |
| 4 min. infusion | 72.0 |
| 6 min. infusion | 78.0 |
| Tea, rosehip | 4.0 |
| Juices | |
| Apple juice | trace |
| Cranberry juice | 6.6 |
| Grape juice | 5.8 |
| Grapefruit juice | 0.0 |
| Orange juice | 0.5 |
| Pineapple juice | 0.0 |
| Tomato juice | 5.0 |
| Beverages, alcoholic | |
| Beer: | |
| bottled | 0.0 |
| draft | 1.0 |
| Lager draft, Tuborg Pilsner | 4.0 |
| Stout, Guiness Draft | 2.0 |
| Cider | 0.0 |
| Sherry, dry | trace |
| Wine: | |
| Port | trace |
| Rose | 1.5 |
| White | 0.0 |
| Miscellaneous | |
| Cocoa, dry powder | 623.0 |
| Coffee powder (Nescafe) | 33.0 |
| Chicken noodle soup | 1.0 |
| Lemon juice | 1.0 |
| Lime juice | 0.0 |
| Ovaltine, powder canned | 35.0 |
| Oxtail soup | 1.0 |
| Pepper | 419.0 |
| Tomato soup | 3.0 |
| Vegetable soup | 5.0 |

From: Krause & Mahen, Food, Nutritient Diet Therapy, 7th ed., 1984, W. B. Saunders, Phila.

TABLE IV

Concentrations of oxalic acid, calcium and magnesium in foods

| Food | Oxalic Acid (mmol/kg fresh wt) | Calcium (mmol/kg fresh wt) | Magnesium (mmol/kg fresh wt) |
|---|---|---|---|
| Vegetables | | | |
| Cabbage | 0.11 | 16.2 | 8.5 |
| Cauliflower | 0.12 | 5.9 | 6.4 |
| Onion | 0.33 | 7.1 | 4.8 |
| Potato | 0.25 | 2.2 | — |
| Lettuce | 0.19 | 6.5 | 4.1 |
| Rhubarb | 28.9 | 3.1 | 4.0 |
| Beetroot | 13.5 | 4.7 | 15.5 |
| Spinach | 86.6 | 27.7 | 31.6 |
| Fruit | | | |
| Apple | 0.17 | 0.85 | 2.05 |
| Orange | 0.69 | 0.87 | 5.70 |
| Pear | 0.19 | 1.0 | 1.85 |
| Plum | 0.38 | 3.57 | 3.33 |
| Strawberry | 0.21 | 4.10 | 4.73 |
| Tomato | 0.59 | 2.50 | 4.11 |
| Meat, fish and dairy products | | | |
| Beef, roasted | 0.04 | 1.92 | 11.7 |
| Fish (haddock) | 0.02 | 4.22 | 11.6 |
| Milk (cow) | 0.005 | 28.7 | 4.3 |
| Cereals | | | |
| Bread, white | 0.54 | 27.0 | 10.0 |
| Cornflakes | 0.62 | 2.2 | 14.8 |

TABLE IV-continued

Concentrations of oxalic acid, calcium and magnesium in foods

| Food | Oxalic Acid (mmol/kg fresh wt) | Calcium (mmol/kg fresh wt) | Magnesium (mmol/kg fresh wt) |
|---|---|---|---|
| Beverages | | | |
| Ovaltine, powder | 5.1 | 31.5 | 13.6 |
| Tea (1 g/100 ml, infused for 2 min) | 0.51 | 0.07 | 0.25 |
| Tea (1.5 g/100 ml, infused for 6 min) | 0.92 | 0.13 | 1.03 |

Zarembski and Hodgkinson (1962b).

TABLE V

Dietary intake of oxalate by man and animals

| Description mg/kg day | Oxalic acid (anhydrous) Mean | Range | Mean | Range | Reference |
|---|---|---|---|---|---|
| Man | | | | | |
| British | 920 | 850–980 | 12.3 | 10.1–13.6 | Archer et al. (1957a) |
| British | 97 | 70–150 | 1.4 | 1.0–2.1 | Zarembski and Hodgkinson (1962b) |
| British | — | 145–175 | — | — | Anderson et al. (1971) |
| Indian on hospital diet | 139.4 | — | — | — | Singh et al. (1972) |
| Indian on common rural diet | 77.8 | — | — | — | Singh et al. (1972) |
| Indian on seasonal rural diet | 2045.0 | — | — | — | Singh et al. (1972) |
| Indian on urban diet, lower income group | 168.5 | — | — | — | Singh et al. (1972) |
| Indian on urban diet, upper income group | 606.4 | — | — | — | Singh et al. (1972) |
| Indian from Kashmir | — | 260–450 | — | — | Dhar and Kaul (1973) |
| Sheep | — | 2160–5000 | — | 31.7–73.5 | Brune (1955) |
| Cow (Heifer) | — | 60700 | — | 243–286 | Talapatra et al. (1942) |
| | — | 71500 | — | — | Talapatra et al. (1942) |
| Rat | | | | | |
| Wistar (300 g) | — | 14–28 | — | 46–92 | Hodgkinson (unpublished results) |
| Sand rat (200 g) | — | 300–500 | — | 1500–2500 | Shirley and Schmidt-Nielsen (1967). |

*Oxalic Acid in Biology and Medicine, pg. 160.

TABLE VI

Some recent estimates of the concentration of oxalic acid in human and animal blood

| Analytical method | Oxalic acid ($\mu$g anhydrous acid/100 ml) Mean | Range | Reference |
|---|---|---|---|
| Man | | | |
| Fluorimetry | 146.0 | 100–235[a] | Hodgkinson and Zarembski |
| | 169.0 | 127–254[c] | (1968) |
| Fluorimetry | 256.0 | 150–480[a] | Endo (1969) |
| Chemical kinetics | 124.0[b] | — | Eswara-Dutt and Mottola (1974) |
| Enzymic Decarboxylation | 118.0 | 80–140[b] | Knowles and Hodgkinson (1972) |
| Enzymic decarboxylation | 130.4 | 73–199[b,d] | Hatch et al. (1977) |
| | 261.1 | 136–465[b,e] | |
| Ion exchange and colorimetry | — | 117–250[a] | Krugers Dagneaux et al. (1976) |
| [$^{14}$C] oxalic acid | 16.5 | — | Williams et al. (1971) |
| [$^{14}$C] oxalic acid | 13.0 | 11.8–14.3[a] | Hodgkinson and Wilkinson (1974) |
| Sheep | | | |
| [$^{14}$C] oxalic acid | — | 52.6–74.4[a] | McIntosh and Belling (1975) |

*Oxalic Acid In Biology and Medicine, pg. 174.

TABLE VI-continued

Some recent estimates of the concentration of oxalic acid in human and animal blood

| Analytical method | Oxalic acid ($\mu$g anhydrous acid/100 ml) | | Reference |
|---|---|---|---|
| | Mean | Range | |

[a]Plasma
[b]Serum
[c]Whole blood
[d]Male
[e]Female

TABLE VII

Vitamin B-6 (Pyridoxine) Content of Pork and Pork Products

| Pork | Raw | Cooked Broiled/Braised | Cooked Roasted | Cooked Pan Fried |
|---|---|---|---|---|
| Composite of Retail Cuts All Lean and Fat | .445 | .394 | | |
| Leg, Loin & Shoulder Composite of Retail Cuts All Lean and Fat | .508 | .434 | | |
| Leg (Ham) Whole Lean and Fat | .401 | .402 | | |
| Leg (Ham) Whole Lean Only | .500 | .400 | | |
| Loin Whole Lean and Fat | .472 | .460 | .382 | |
| Loin Whole Lean Only | .527 | .492 | .404 | |
| Back Ribs Lean and Fat | .395 | | .307 | |
| Loin Chops Lean and Fat | .370 | .297 (braised) .381 (broiled) | | .337 |
| Bacon Cured | .14 | .27 | | |
| Canadian Style, Bacon Unheated | .38 | .45 (unheated) | | |
| Ham, Boneless Extra Lean & Regular | .38 (unheated) | | | .35 |
| Ham, Boneless (11% Fat) Extra Lean and Regular | .34 (unheated) | | | .31 |

Source: U.S. Department of Agriculture
Agriculture Handbook 8–10 Rev. 1992

TABLE VIII

Vitamin B-6 (Pyridoxine) Content of Beef and Beef Products

| Beef | All Grades | | Good | | Choice | | Prime | |
|---|---|---|---|---|---|---|---|---|
| | Raw | Cooked | Raw | Cooked | Raw | Cooked | Raw | Choice |
| Composite Retail Cuts Lean and Fat | .36 | .31 | .37 | .32 | .36 | .31 | .34 | .29 |
| Composite Retail Cuts Lean Only | .43 | .38 | .44 | .38 | .43 | .38 | .43 | .38 |

| Beef | Raw | Roasted | Broiled |
|---|---|---|---|
| Large Ribs Lean and Fat | | .28 | .22 | .26 |
| Rib-Eye Small Ribs Lean and Fat | .38 | .32 | .36 |
| Whole Prime Ribs Lean and Fat | .30 | .25 | .29 |

| Beef | Mg/100 Grams |
|---|---|
| Beef Cured Frankfurter | .12 |
| Lebanon Bologna | .24 |
| Pastrami | .18 |
| Sausage Cooked and Smoked | .11 |
| Beef Cured and Corned | .13 |
| Liver Pan Fried | 1.43 |
| Kidney Cooked | .52 |
| Ground Lean Fried | .28 |
| Ground Lean Baked | .20 |

Source: U.S. Department of Agriculture
Agriculture Handbook 8–13 1986

TABLE IX

Vitamin B-6 (Pyridoxine) Content of Veal and Lamb

| Meat | Raw | Cooked |
|---|---|---|
| Veal All Retail Cuts Lean and Fat | .41 | 31 |
| Lamb All Retail Cuts Lean and Fat | .13 | .13 |
| Lamb All Retail Cuts Lean | .16 | .16 |

Source: USDA Department of Agriculture
Agriculture Handbook 8-17-1989

TABLE X

| Chicken | Raw | Fried Batter-Dipped | Fried Flour Dipped | Roasted | Stewed |
|---|---|---|---|---|---|
| Broilers or Fryers All Meat with Skin | .34 | .32 | .42 | .38 | .22 |
| Broilers or Fryers All Meat Flesh Only | .43 | .48 | .53 | .47 | .26 |
| Broilers or Fryers Light Meat with Skin | .48 | .39 | .54 | .52 | .27 |
| Broilers or Fryers Light Meat Flesh Only | .54 | .63 | .65 | .60 | .26 |
| Broilers and Fryers Dark Meat with Skin | .25 | .25 | .32 | .31 | .17 |
| Broiler and Fryers Thigh with Skin | .26 | .26 | .33 | .31 | .17 |
| Broiler and Fryers Leg with Skin | .29 | .27 | .34 | .33 | .18 |
| Ground Turkey | .35 | .39 (Cooked) | | | |

Source: U.S. Department of Agriculture
Agriculture Handbook 8-5-1978

TABLE XI

VITAMIN B-6 (PYRIDOXINE) CONTENT OF SELECTED BAKED GOODS

| Breads | Mg/100 G |
|---|---|
| Bagels: Plain, Onion, Poppy Seed, Sesame | .051 |
| Bagels, Date Bran | .000 |
| Bagels, Egg | .084 |
| Bagels, Cinnamon Raisin | .000 |
| Biscuits, Commercially Baked Plain or Buttermilk | .047 |
| Cornbread | .113 |
| Cracked Wheat Bread | .304 |
| French and Vienna Bread | .043 |
| Italian Bread | .048 |
| Mixed Grains 7 Bread | .333 |
| Oat Bran Bread | .000 |
| Pumpernickel | .126 |
| Rye Bread | .075 |
| Wheat Bran Bread | .064 |
| Whole Wheat Commercial Bread | .179 |

Source: U.S. Deptartment of Agriculture
Agriculture Handbook 8–18 Rev. 1992

TABLE XII

Dry Dog Food Test Run Data

| E325 Processing Conditions: | Run #1 | Comment |
|---|---|---|
| Product | Dry Dog Food | |
| Feeder Speed (RPM) | 11 rpm (420 lbs/hr) | |
| Feeder Speed (Hertz) | 34.7 | |
| Cond. Cyl. Temp (° F.) | 206 | |
| Cond. Cyl. Water (% gauge) | 10 | |
| Extruder Speed (RPM) | 421 | |
| Extruder Current (Amps) | 24 | |
| Extruder Water (% gauge) | 0 | |
| Extruder Steam Injection | 0 | |
| #2 Head Temp. (CW or ST) | CW | |
| #3 Head Temp. (CW or ST) | CW | |
| #4 Head Temp. (CW or ST) | CW | |
| #5 Head Temp. (° F.) | CW 79 deg F. | |
| #6 Head Temp. (° F.) | CW 129 deg F. | |
| Die Pressure (PSI) | 350 | |
| Knife Speed (Hertz) | 55.9 | |
| Dryer Temperature (° F.) | 223 | |
| Dryer Retention (minutes) | 17.9 | |
| Formula: | See Dry Feed formula 2.2% Oxalic acid solution added at 0.7 lbs/min | 2.7# OA to 100# water |
| Comments: | The oxalic acid solution was made up in hot water (160° F.) and pumped into the conditioning cylinder | |
| Screw Configuration: | | |
| #1 Screw | Single Flight Tapered Inlet | Straight Rib Head |
| #1 Steamlock | Spacer | |
| #2 Screw | Single Flight Uncut | Spiral Rib Head |
| #2 Steamlock | Spacer | |
| #3 Screw | Single Flight Uncut | Spiral Rib Head |
| #3 Steamlock | Spacer | |
| #4 Screw | Single to Double Flight Uncut | Straight Rib Head |
| #4 Steamlock | Small | |
| #5 Screw | 2 Flight cut flight | Straight Rib Head |
| #5 Steamlock | Large | |
| #6 Screw | 2 Flight cut flight cone | Spiral Rib Cone Head |
| Die Configuration: | | |
| Spacer | 1" thick | |
| Backup Die | No | |
| Dieplate | 1 1/4" central insert die | #825440-3 |
| Insert | 1/4" round hole | #101-509 |

Thus, it will be appreciated that as a result of the present invention, a highly effective oxalic acid or oxalate composition and method is provided by which the principal object, among others, is completely fulfilled. It is contemplated, and will be apparent to those skilled in the art from the preceding description that modifications and/or changes may be made in the prescribed embodiments without departure from the present invention. Accordingly, it is expressly intended that the foregoing description is illustrative of preferred embodiments only, and not limiting with respect to the true spirit and scope of the present invention.

What is claimed is:

1. A chemopreventive composition for treating at least one of tumors, brain tumors, cancers, and growths in warm blooded animals sensitive to treatment comprising a composition having an effective amount of at least one therapeutically effective form of at least one of oxalic acid and oxalate and at least one of a carrier and diluent for said at least one of oxalic acid and oxalate, wherein said effective amount is less than a lethal dosage of oxalic acid and wherein said composition is adapted to be administered to warm-blooded animals on a periodic basis in less than a lethal dosage.

2. The composition as recited in claim 1 wherein said therapeutically effective form of at least one of oxalic acid and oxalate is oxalic acid in a free acid form.

3. The composition as recited in claim 1 wherein said therapeutically effective form of at least one of oxalic acid and oxalate is oxalic acid dihydrate.

4. The composition as recited in claim 1 wherein said therapeutically effective form of at least one of oxalic acid and oxalate is dried parsley.

5. The composition as recited in claim 1 further comprising a pharmaceutically acceptable carrier or diluent.

6. The composition as recited in claim 1 wherein said carrier or diluent is distilled water.

7. The composition as recited in claim 1 wherein said therapeutically effective form of at least one of oxalic acid and oxalate is a nutritional supplement containing an effective amount of at least one therapeutically effective form of at least one of oxalic acid and oxalate.

8. The composition as recited in claim 1 wherein said therapeutically effective form of at least one of oxalic acid and oxalate is selected from the group of natural foods, processed foods, molds, plants, and vegetables containing an effective amount of at least one therapeutically effective form of at least one of oxalic acid and oxalate.

9. The composition as recited in claim 1 wherein said therapeutically effective form of at least one of oxalic acid and oxalate is selected from the group of beverages, liquids, and juices containing an effective amount of at least one therapeutically effective form of at least one of oxalic acid and oxalate.

10. The composition as recited in claim 1 wherein said therapeutically effective form of at least one of oxalic acid and oxalate is selected from the group of additives containing at least one therapeutically effective form of at least one of oxalic acid and oxalate.

11. The composition as recited in claim 5, wherein said at least one carrier and diluent is a gel cap.

12. The composition as recited in claim 5, wherein said at least one carrier and diluent is at least one of a gel cap, distilled water, tablet, powder, food additive, drops, liquid, beverage, rinse, mouthwash, gargle, pill, capsule, lozenge, cough drop, transdermal patch, ointment, salve, cream, lotion, and gel, adapted for periodically administering a therapeutically effective dosage by at least one of topical, oral, nasal, parenteral, intravenous, and subcutaneous application.

13. The composition as recited in claim 1, wherein said effective amount is at least one of about 50 mg to 6 g for humans and about 1 mg to 3 g for warm blooded animals other than humans.

14. An anti-tumor agent to be used in a method for treating at least one of tumors, growths, and cancers in warm blooded animals sensitive to treatment comprising a mixture of an effective amount of at least one therapeutically effective form of at least one of oxalic acid and oxalate with at least one of a pharmaceutically acceptable carrier and diluent.

15. The agent as recited in claim 14 wherein said therapeutically effective form of at least one of oxalic acid and oxalate is oxalic acid dihydrate.

16. The agent as recited in claim 14 wherein said pharmaceutically acceptable carrier or diluent is selected from the group of distilled water, heated water, pharmaceutically acceptable liquids, nutritional supplements, natural foods and processed foods.

17. The anti-tumor agent as recited in claim 14, wherein said at least one carrier and diluent is at least one of a gel cap, distilled water, tablet, powder, food additive, drops, liquid, beverage, rinse, mouthwash, gargle, pill, capsule, lozenge, cough drop, transdermal patch, ointment, salve, cream, lotion, and gel, adapted for periodically administering a therapeutically effective dosage by at least one of topical, oral, nasal, parenteral, intravenous, and subcutaneous application.

18. The agent as recited in 14, wherein said effective amount is at least one of about 50 mg to 6 g for humans and about 1 mg to 3 g for warm blooded animals other than humans.

19. A therapeutic composition in cream or ointment form for topical administration of an effective amount of at least one therapeutically effective form of at least one of oxalic acid and oxalate for treating at least one of tumors, growths, and cancers in warm blooded animals sensitive to treatment comprising an effective amount of at least one therapeutically effective form of at least one of oxalic acid and oxalate, a solvent, and a base.

20. The therapeutic composition as recited in claim 19 wherein said solvent is at least one of distilled water, acetone, propylene glycol, and polysorbate, and said base is at least one of a cream, ointment, gel, lotion, spray, stick, and powder.

21. The therapeutic composition as recited in claim 19 wherein said solvent is at least one of distilled water, acetone, propylene glycol, and polysorbate and said base is at least one of a hydrophilic petrolatum, cream, ointment, gel, lotion, spray, stick, and powder.

22. The composition as recited in claim 19, wherein said effective amount is at least one of about 50 mg to 6 g for humans and about 1 mg to 3 g for warm blooded animals other than humans.

23. In a pet food containing at least one of protein, carbohydrates, oils, vitamins, and minerals, to be used in a method for treating at least one of tumors, growths, and cancers in warm blooded animals sensitive to treatment, the improvement comprising the addition of a therapeutically effective quantity of at least one therapeutically effective form of at least one of oxalic acid and oxalate.

24. The pet food as recited in claim 23, wherein the effective quantity is about 1 mg to 3 g per pet.

25. In a method of manufacturing a dry process dog food to be used in a method for treating at least one of tumors, growths, and cancers in warm blooded animals sensitive to treatment, the improvement comprising the steps of mixing a slurry of conventional dog food ingredients together with a dilute solution of an effective amount of at least one therapeutically effective form of at least one of oxalic acid and oxalate in heated water to form at least one of an oxalic acid and oxalate containing slurry, forming the slurry into pellets and drying the pellets.

26. The method as recited in claim 25 wherein said oxalic acid is oxalic acid dihydrate and each pellet contains approximately 1 mg of oxalic acid so that one pound of dry dog food contains about 1 g of oxalic acid.

27. The method as recited in claim 25, further comprising the steps of reducing the intake of oxalic acid or oxalate blockers selected from at least one of citric acid, ascorbic acid, (vitamin C), pyridoxine hydrochloride (vitamin B6), calcium, alcohol, resins, clays, foods containing calcium, beverages containing alcohol, citric acid, or ascorbic acid, red meat or white meat of fowl containing pyridoxine hydrochloride, and foods, nutritional supplements, or beverages containing oxalic acid or oxalate blockers.

28. An oral rinse or wash for treating at least one of tumors, cancers, and growths in warm blooded animals sensitive to treatment in the mouth area comprising a dilute solution of an effective amount of at least one therapeutically effective form of at least one of oxalic acid and oxalate, wherein said effective amount is less than a lethal dosage of oxalic acid and wherein said solution is adapted to be administered periodically in less than a lethal dosage.

29. The oral rinse or wash as recited in claim 28 comprising a dilute solution of oxalic acid dihydrate in distilled water.

30. The oral rinse as recited in claim 29, wherein said rinse contains a solution ratio of about 150 mg oxalic acid dihydrate in about 300 ml distilled water.

31. The oral rinse as recited in claim 28, wherein said rinse contains a solution ratio of about 150 mg oxalic acid dihydrate in about 300 ml distilled water.

32. A dietary supplement for treating a patient diagnosed with at least one of an active cancer, tumor, and growth sensitive to treatment comprising about 1 g to 6 g of at least one therapeutically effective form of at least one of oxalic acid and oxalate per day based on 70 kilograms of body weight and at least one of a pharmaceutically acceptable carrier and diluent.

33. The dietary supplement as recited in claim 32, wherein said at least one carrier and diluent is at least one of a gel cap, distilled water, tablet, powder, food additive, drops, liquid, beverage, rinse, mouthwash, gargle, pill, capsule, lozenge, cough drop, transdermal patch, ointment, salve, cream, lotion, and gel, adapted for periodically administering a therapeutically effective dosage by at least one of topical, oral, nasal, parenteral, intravenous, and subcutaneous application.

34. The dietary supplement as recited in claim 32, wherein said effective amount is at least one of about 50 mg to 6 g for humans and about 1 mg to 3 g for warm blooded animals other than humans.

35. A pharmaceutical composition to be administered orally to humans for treating at least one of tumors, growths, and cancers in warm blooded animals sensitive to treatment comprising a mixture of a non-toxic ingestible carrier and an effective amount of a therapeutically effective form of at least one of oxalic acid and oxalate.

36. The pharmaceutical composition as recited in claim 35, wherein said at least one carrier and diluent is at least one of a gel cap, distilled water, tablet, powder, food additive, drops, liquid, beverage, rinse, mouthwash, gargle, pill, capsule, lozenge, cough drop, transdermal patch, ointment, salve, cream, lotion, and gel, adapted for periodically administering a therapeutically effective dosage by at least one of topical, oral, nasal, parenteral, intravenous, and subcutaneous application.

37. The composition as recited in claim 35, wherein said effective amount is about 50 mg to 6 g.

38. The pharmaceutical composition as recited in claim 35 wherein said composition is provided in a form selected from the group of pills, powders, granules, tablets, microcapsules, gel capsules, nutritional supplements, processed foods, liquids, drops, beverages, additives, and solutions.

39. In a pet treat containing at least one of protein, carbohydrates, and flavorings, to be used in a method for treating at least one of tumors, growths, and cancers in warm blooded animals sensitive to treatment w, the improvement comprising the addition of microgram amounts of at least one therapeutically effective form of at least one of oxalic acid and oxalate, whereby the treats provide for the maintenance of good pet health.

40. The pet treat as recited in claim 39, wherein the microgram amount provides for about 1 mg to 3 g per pet per day.

41. A chemopreventive composition for treating at least one tumor in a warm blooded animal sensitive to treatment comprising a composition including an effective amount of at least one therapeutically effective form of at least one of oxalic acid and oxalate and at least one of a carrier and diluent for said at least one of oxalic acid and oxalate, wherein said effective amount is less than a lethal dosage of oxalic acid and wherein said composition is adapted to be administered to warm-blooded animals on a periodic basis in less than a lethal dosage.

42. The chemopreventive composition as recited in claim 41, wherein the effective amount is at least one of about 50 mg to 6 g for humans and about 1 mg to 3 g for warm blooded animals other than humans.

43. A chemopreventive composition for treating at least one cancer in a warm blooded animal sensitive to treatment comprising a composition including an effective amount of at least one therapeutically effective form of at least one of oxalic acid and oxalate and at least one of a carrier and diluent for said at least one of oxalic acid and oxalate, wherein said effective amount is less than a lethal dosage of oxalic acid and wherein said composition is adapted to be administered to warm-blooded animals on a periodic basis in less than a lethal dosage.

44. The chemopreventive composition as recited in claim 43, wherein the effective amount is at least one of about 50 mg to 6 g for humans and about 1 mg to 3 g for warm blooded animals other than humans.

45. In a gel cap, the improvement comprising a therapeutically effective dosage of oxalic acid less than a lethal dosage.

46. The gel cap as recited in claim 45, wherein the effective dosage is at least one of about 50 mg to 6 g for humans and about 1 mg to 3 g for warm blooded animals other than humans.

47. In a pill, the improvement comprising a therapeutically effective dosage of oxalic acid less than a lethal dosage.

48. The pill as recited in claim 47, wherein the effective dosage is at least one of about 50 mg to 6 g for humans and about 1 mg to 3 g for warm blooded animals other than humans.

49. In a drug delivery system, the improvement comprising a therapeutically effective dosage of oxalic acid less than a lethal dosage.

50. The drug delivery system as recited in claim 49, wherein the therapeutically effective dosage is at least one of about 50 mg to 6 g for humans and about 1 mg to 3 g for warm blooded animals other than humans.

51. A method for treating at least one of tumors, growths, and cancers in warm blooded animals sensitive to treatment comprising the steps of periodically administering a therapeutically effective dosage of at least one composition of a therapeutically effective form of at least one of oxalic acid and oxalate to said animal, wherein said dosage is less than a lethal dosage of oxalic acid and wherein said composition is adapted to be administered periodically in less than a lethal dosage.

52. The method as recited in claim 51 wherein said composition is administered at least one of orally and sublingually.

53. The method as recited in claim 51 wherein said composition is administered by injection.

54. The method as recited in claim 51 wherein said composition is administered topically.

55. The method as recited in claim 51 wherein said composition is administered internally.

56. The method as recited in claim 51 wherein said composition is administered at least once a day at a dosage of at least one of 50 mg to 6 g for humans and 1 mg to 3 g for warm blooded animals other than humans.

57. The method as recited in claim 51 wherein said composition is administered at least once a day at a dosage of about 1 mg to 3 g for dogs and cats.

58. The method as recited in claim 51, wherein said composition is administered by injection.

59. The method as recited in claim 51, further comprising the steps of reducing the intake of oxalic acid or oxalate blockers selected from at least one of citric acid, ascorbic acid, (vitamin C), pyridoxine hydrochloride (vitamin B6), calcium, alcohol, resins, clays, foods containing calcium, beverages containing alcohol, citric acid, or ascorbic acid, red meat or white meat of fowl containing pyridoxine hydrochloride, and foods, nutritional supplements, or beverages containing oxalic acid or oxalate blockers.

60. The method as recited in claim 51 further comprising the steps of reducing the intake of oxalic acid or oxalate blockers.

61. The method as recited in claim 60 wherein said blockers are selected from the group of citric acid, ascorbic acid, pyridoxine hydrochloride, calcium, alcohol, resins, clays, and combinations thereof.

62. The method as recited in claim 60 wherein said blockers are selected from the group of dairy products containing calcium, fruits, coconut, beverages containing alcohol, ascorbic acid or citric acid including adult beverages such as beer, wine, vodka, gin, and the like, fruit juice based beverages, soda pop or soft drinks containing ascorbic acid or citric acid, other sports drinks, beverages or refreshments containing calcium, ascorbic acid or citric acid, red meat or white meat of fowl including chicken, turkey, pheasant and the like containing pyridoxine hydrochloride, or other foods or beverages containing alcohol, citric acid, ascorbic acid, calcium or pyridoxine hydrochloride including breads or grains, and combinations thereof.

63. A method for treating at least one of cancers, tumors, and growths in warm blooded animals sensitive to treatment comprising the steps of adding to the regular diet a dietary supplement of an effective amount of at least one therapeutically effective form of at least one of oxalic acid and oxalate.

64. The method as recited in claim 63 wherein said therapeutically effective form of at least one of oxalic acid and oxalate is oxalic acid in a free acid form.

65. The method as recited in claim 63 wherein said therapeutically effective form of at least one of oxalic acid and oxalate is a nutritional supplement containing at least one form of at least one of oxalic acid and oxalate.

66. The method as recited in claim 63 wherein said therapeutically effective form of at least one of oxalic acid and oxalate is oxalic acid dihydrate.

67. The method as recited in claim 63 wherein said therapeutically effective form of at least one of oxalic acid and oxalate is processed foods containing at least one form of at least one of oxalic acid and oxalate.

68. The method as recited in claim 63 wherein said therapeutically effective form of at least one of oxalic acid and oxalate is at least one of plants and vegetables containing at least one form of at least one of oxalic acid and oxalate.

69. The method as recited in claim 63 wherein said therapeutically effective form of at least one of oxalic acid and oxalate is at least one of beverages, liquids, and juices containing at least one form of at least one of oxalic acid and oxalate.

70. The method as recited in claim 63 wherein said therapeutically effective form of at least one of oxalic acid and oxalate is additives containing at least one form of at least one of oxalic acid and oxalate.

71. The method as recited in claim 63, wherein said effective amount is a daily dosage of at least one of about 50 mg to 6 g for humans and about 1 mg to 3 g for warm blooded animals other than humans.

72. The method as recited in claim 63, further comprising the steps of reducing the intake of oxalic acid or oxalate blockers selected from at least one of citric acid, ascorbic acid, (vitamin C), pyridoxine hydrochloride (vitamin B6), calcium, alcohol, resins, clays, foods containing calcium, beverages containing alcohol, citric acid, or ascorbic acid, red meat or white meat of fowl containing pyridoxine hydrochloride, and foods, nutritional supplements, or beverages containing oxalic acid or oxalate blockers.

73. The diet as recited in claim 63 further comprising the steps of reducing the intake of oxalic acid or oxalate blockers.

74. The diet as recited in claim 73 wherein said blockers are selected from the group of citric acid, ascorbic acid, pyridoxine hydrochloride, calcium, alcohol, resins, clays, and combinations thereof.

75. The diet as recited in claim 73 wherein said blockers are selected from the group of dairy products containing calcium, fruits, coconut, beverages containing alcohol, ascorbic acid, or citric acid including adult beverages such as beer, wine, vodka, gin, and the like, fruit juice based beverages, soda pop or soft drinks containing ascorbic acid or citric acid, other sports drinks, beverages or refreshments containing calcium, ascorbic acid or citric acid, red meat or white meat of fowl including chicken, turkey, pheasant, and the like containing pyridoxine hydrochloride, or other foods or beverages containing alcohol, ascorbic acid, citric acid, calcium or pyridoxine hydrochloride including breads or grains, and combinations thereof.

76. A method of treating warm-blooded animals afflicted with tumor cells sensitive to an effective amount of at least one of an oxalic acid and oxalate compound comprising the steps of periodically administering to the animal an oncolytic amount of at least one therapeutically effective oxalic acid and oxalate compound.

77. The method as recited in claim 76, further comprising the steps of reducing the intake of oxalic acid or oxalate blockers selected from at least one of citric acid, ascorbic acid, (vitamin C), pyridoxine hydrochloride (vitamin B6), calcium, alcohol, resins, clays, foods containing calcium, beverages containing alcohol, citric acid, or ascorbic acid, red meat or white meat of fowl containing pyridoxine hydrochloride, and foods, nutritional supplements, or beverages containing oxalic acid or oxalate blockers.

78. The method as recited in claim 76, wherein said compound is administered at daily dosage of at least one of about 50 mg to 6 g for humans and about 1 mg to 3 g for warm blooded animals other than humans.

79. A method of treating brain tumors in warm blooded animals sensitive to treatment comprising the steps of ingesting or administering a therapeutically effective amount of at least one therapeutically effective form of at least one of oxalic acid and oxalate.

80. The method as recited in claim 79 wherein the therapeutically effective form of at least one of oxalic acid and oxalate is dried chopped parsley.

81. The method as recited in claim 79, further comprising the steps of reducing the intake of oxalic acid or oxalate blockers selected from at least one of citric acid, ascorbic acid, (vitamin C), pyridoxine hydrochloride (vitamin B6), calcium, alcohol, resins, clays, foods containing calcium, beverages containing alcohol, citric acid, or ascorbic acid, red meat or white meat of fowl containing pyridoxine hydrochloride, and foods, nutritional supplements, or beverages containing oxalic acid or oxalate blockers.

82. The method as recited in claim 79, wherein said effective form of at least one of oxalic acid and oxalate is administered at daily dosage of at least one of about 50 mg to 6 g for humans and about 1 mg to 3 g for warm blooded animals other than humans.

83. A method for treating at least one of tumors, growths, and cancers in warm-blooded animals sensitive to treatment comprising the steps of periodically administering a therapeutically effective dosage of the composition of claim 1 and adding to the regular diet a dietary supplement of an effective amount of at least one therapeutically effective form of at least one of oxalic acid and oxalate.

84. The method as recited in claim 83, further comprising the steps of reducing the intake of oxalic acid or oxalate blockers selected from at least one of citric acid, ascorbic acid, (vitamin C), pyridoxine hydrochloride (vitamin B6), calcium, alcohol, resins, clays, foods containing calcium, beverages containing alcohol, citric acid, or ascorbic acid, red meat or white meat of fowl containing pyridoxine hydrochloride, and foods, nutritional supplements, or beverages containing oxalic acid or oxalate blockers.

85. The method as recited in claim 83, wherein said composition is administered at daily dosage of at least one of about 50 mg to 6 g for humans and about 1 mg to 3 g for warm blooded animals other than humans.

86. A method for treating cancer in warm blooded animals sensitive to treatment, comprising the steps of:

periodically administering a therapeutically effective dosage of at least one therapeutically effective form of at least one of oxalic acid and oxalate to said animal, wherein said effective amount is less than a lethal dosage of oxalic acid and wherein said solution is adapted to be administered periodically in less than a lethal dosage.

87. The method as recited in claim 86, wherein said composition is administered at least one of orally and sublingually.

88. The method as recited in claim 86, wherein said composition is administered by injection.

89. The method as recited in claim 86, wherein said composition is administered topically.

90. The method as recited in claim 86, wherein said composition is administered internally.

91. The method as recited in claim 86, wherein said composition is administered at least once a day at a dosage of at least one of 50 mg to 6 g for humans and 1 mg to 3 g for warm blooded animals other than humans.

92. The method as recited in claim 86, further comprising the steps of reducing the intake of oxalic acid or oxalate blockers selected from at least one of citric acid, ascorbic acid, (vitamin C), pyridoxine hydrochloride (vitamin B6), calcium, alcohol, resins, clays, foods containing calcium, beverages containing alcohol, citric acid, or ascorbic acid, red meat or white meat of fowl containing pyridoxine hydrochloride, and foods, nutritional supplements, or beverages containing oxalic acid or oxalate blockers.

93. A method for treating at least one tumor in a warm blooded animal sensitive to treatment comprising the steps of periodically administering a therapeutically effective dosage of at least one composition of a therapeutically effective form of at least one of oxalic acid and oxalate and at least one of a carrier and diluent for said at least one of oxalic acid and oxalate, wherein said effective amount is less than a lethal dosage of oxalic acid and wherein said composition is adapted to be administered to warm-blooded animals on a periodic basis in less than a lethal dosage to said animal.

94. The method as recited in claim 93, further comprising the steps of reducing the intake of oxalic acid or oxalate blockers selected from at least one of citric acid, ascorbic acid, (vitamin C), pyridoxine hydrochloride (vitamin B6), calcium, alcohol, resins, clays, foods containing calcium, beverages containing alcohol, citric acid, or ascorbic acid, red meat or white meat of fowl containing pyridoxine hydrochloride, and foods, nutritional supplements, or beverages containing oxalic acid or oxalate blockers.

95. The method as recited in claim 93, wherein said composition is administered at daily dosage of at least one of about 50 mg to 6 g for humans and about 1 mg to 3 g for warm blooded animals other than humans.

96. A method for treating at least one cancer in a warm blooded animals sensitive to treatment comprising the steps of periodically administering a therapeutically effective dosage of at least one composition of a therapeutically effective form of at least one of oxalic acid and oxalate and at least one of a carrier and diluent for said at least one of oxalic acid and oxalate, wherein said effective amount is less than a lethal dosage of oxalic acid and wherein said composition is adapted to be administered to warm-blooded animals on a periodic basis in less than a lethal dosage to said animal.

97. The method as recited in claim 96, further comprising the steps of reducing the intake of oxalic acid or oxalate blockers selected from at least one of citric acid, ascorbic acid, (vitamin C), pyridoxine hydrochloride (vitamin B6), calcium, alcohol, resins, clays, foods containing calcium, beverages containing alcohol, citric acid, or ascorbic acid, red meat or white meat of fowl containing pyridoxine hydrochloride, and foods, nutritional supplements, or beverages containing oxalic acid or oxalate blockers.

98. The method as recited in claim 96, wherein said composition is administered at daily dosage of at least one of about 50 mg to 6 g for humans and about 1 mg to 3 g for warm blooded animals other than humans.

99. A treatment regimen for treating tumors, cancers, growths, and neoplasia in warm blooded animals sensitive to treatment comprising the steps of reducing or eliminating the ingestion or administration of oxalic acid or oxalate blockers, administering or ingesting high dosages of at least one of oxalic acid and oxalate to raise the blood or urine oxalic acid or oxalate level above normal, and, after cleansing the blood of tumor, cancer or abnormal cells, administering or ingesting a more moderate level of at least one of oxalic acid and oxalate to maintain a normal blood or urine oxalic acid or oxalate level.

100. The regimen as recited in claim 99 further comprising the steps of increasing the administration or ingestion of oxalic acid or oxalate enhancers.

101. A chemopreventive composition for treating at least one of tumors, brain tumors, cancers, and growths in humans sensitive to treatment comprising a composition having an effective amount of at least one therapeutically effective form of at least one of oxalic acid and oxalate and at least one of a carrier and diluent for said at least one of oxalic acid and oxalate, wherein said effective amount is less than a lethal dosage of oxalic acid and wherein said composition is adapted to be administered on a periodic basis in less than a lethal dosage.

102. A method for treating at least one of tumors, growths, and cancers in humans sensitive to treatment comprising the steps of periodically administering at therapeutically effective dosage of at least one composition of a therapeutically effective form of at least one of oxalic acid and oxalate, wherein said dosage is less than a lethal dosage of oxalic acid and wherein said composition is adapted to be administered periodically in less than a lethal dosage.

103. The method as recited in claim 102 wherein said composition is administered at least one a day at a dosage of about 50 mg to 6 g.

104. A method for treating at least one of cancers, tumors, and growths in humans sensitive to treatment comprising the steps of adding to the regular diet a dietary supplement of an effective amount of at least one therapeutically effective form of at least one of oxalic acid and oxalate.

* * * * *